(12) United States Patent
Zipory et al.

(10) Patent No.: US 10,299,793 B2
(45) Date of Patent: May 28, 2019

(54) ANCHOR MAGAZINE

(71) Applicant: VALTECH CARDIO, LTD., Or Yehuda (IL)

(72) Inventors: Yuval Zipory, Modi'in (IL); Alexei Koifman, Tel Aviv (IL); Ehud Iflah, Tel Aviv (IL); Tal Reich, Moshav Moledet (IL)

(73) Assignee: Valtech Cardio, Ltd. (IL)

( * ) Notice: Subject to any disclaimer, the term of this patent is extended or adjusted under 35 U.S.C. 154(b) by 381 days.

(21) Appl. No.: 15/030,731

(22) PCT Filed: Oct. 21, 2014

(86) PCT No.: PCT/IL2014/050914
§ 371 (c)(1),
(2) Date: Apr. 20, 2016

(87) PCT Pub. No.: WO2015/059699
PCT Pub. Date: Apr. 30, 2015

(65) Prior Publication Data
US 2016/0262755 A1    Sep. 15, 2016

Related U.S. Application Data

(60) Provisional application No. 61/894,486, filed on Oct. 23, 2013.

(51) Int. Cl.
*A61B 17/10* (2006.01)
*A61B 17/068* (2006.01)
(Continued)

(52) U.S. Cl.
CPC .......... *A61B 17/105* (2013.01); *A61B 17/068* (2013.01); *A61B 50/20* (2016.02);
(Continued)

(58) Field of Classification Search
CPC ................ A61B 17/068; A61B 17/105; A61B 2017/0416; A61B 2017/0649;
(Continued)

(56) References Cited

U.S. PATENT DOCUMENTS

| 3,604,488 A | 9/1971 | Wishart |
| 3,656,185 A | 4/1972 | Carpentier |

(Continued)

FOREIGN PATENT DOCUMENTS

| CA | 2671966 | 6/2008 |
| CN | 101653365 | 2/2010 |

(Continued)

OTHER PUBLICATIONS

O'Reilly S et al., "Heart valve surgery pushes the envelope," Medtech Insight 8(3): 73, 99-108 (2006).

(Continued)

*Primary Examiner* — Katrina Stransky
*Assistant Examiner* — Martin T Ton
(74) *Attorney, Agent, or Firm* — Sanford T. Colb & Co.; Thomas Richardson

(57) ABSTRACT

Apparatus is provided, the apparatus comprising (i) a housing (22, 222), shaped to define a channel (24, 224) having an anchor-storage zone (26, 226) and an opening (28, 228) configured to provide access for an anchor driver (60) to the anchor-storage zone; (ii) a tissue anchor (40), stored in the anchor-storage zone and slidable through the channel; and (iii) a retaining member (30, 230). The retaining member (a) has a retaining state in which the retaining member is configured to retain the tissue anchor in the anchor-storage zone, and (b) is configured, by moving in response to a proximally-directed force applied to the tissue anchor, to allow the tissue anchor to leave the anchor-storage zone in response to the proximally-directed force. The proximally- (Continued)

directed force is greater than a pre-determined threshold force. Other embodiments are described.

30 Claims, 18 Drawing Sheets

(51) Int. Cl.
| | | |
|---|---|---|
| *A61B 50/20* | (2016.01) | |
| *A61B 50/30* | (2016.01) | |
| *A61B 17/00* | (2006.01) | |
| *A61B 17/04* | (2006.01) | |
| *A61B 17/064* | (2006.01) | |

(52) U.S. Cl.
CPC ...... *A61B 50/30* (2016.02); *A61B 2017/0053* (2013.01); *A61B 2017/00243* (2013.01); *A61B 2017/0416* (2013.01); *A61B 2017/0649* (2013.01); *A61B 2017/0688* (2013.01)

(58) Field of Classification Search
CPC . A61B 2017/0688; A61B 50/20; A61B 50/22; A61B 2050/3008; A61B 2050/3009
See application file for complete search history.

(56) References Cited

U.S. PATENT DOCUMENTS

| | | |
|---|---|---|
| 3,840,018 A | 10/1974 | Heifetz |
| 3,881,366 A | 5/1975 | Bradley et al. |
| 3,898,701 A | 8/1975 | La Russa |
| 4,042,979 A | 8/1977 | Angell |
| 4,118,805 A | 10/1978 | Reimels |
| 4,214,349 A | 7/1980 | Munch |
| 4,261,342 A | 4/1981 | Aranguren Duo |
| 4,290,151 A | 9/1981 | Massana |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,917,698 A | 4/1990 | Carpenter et al. |
| 4,961,738 A | 10/1990 | Mackin |
| 5,061,277 A | 10/1991 | Carpentier et al. |
| 5,064,431 A | 11/1991 | Gilbertson et al. |
| 5,104,407 A | 4/1992 | Lam et al. |
| 5,108,420 A | 4/1992 | Marks |
| 5,201,880 A | 4/1993 | Wright |
| 5,258,008 A | 11/1993 | Wilk |
| 5,300,034 A | 4/1994 | Behnke |
| 5,306,296 A | 4/1994 | Wright et al. |
| 5,325,845 A | 7/1994 | Adair |
| 5,346,498 A | 9/1994 | Greelis et al. |
| 5,450,860 A | 9/1995 | O'Connor |
| 5,477,856 A | 12/1995 | Lundquist |
| 5,593,424 A | 1/1997 | Northrup, III |
| 5,601,572 A | 2/1997 | Middleman |
| 5,626,609 A | 5/1997 | Zvenyatsky et al. |
| 5,669,919 A | 9/1997 | Sanders et al. |
| 5,674,279 A | 10/1997 | Wright et al. |
| 5,683,402 A | 11/1997 | Cosgrove et al. |
| 5,702,397 A | 12/1997 | Goble et al. |
| 5,702,398 A | 12/1997 | Tarabishy |
| 5,709,695 A | 1/1998 | Northrup, III |
| 5,716,370 A | 2/1998 | Williamson et al. |
| 5,716,397 A | 2/1998 | Myers |
| 5,728,116 A | 3/1998 | Rosenman |
| 5,730,150 A | 3/1998 | Peppel et al. |
| 5,749,371 A | 5/1998 | Zadini et al. |
| 5,810,882 A | 9/1998 | Bolduc |
| 5,824,066 A | 10/1998 | Gross |
| 5,830,221 A | 11/1998 | Stein et al. |
| 5,843,120 A | 12/1998 | Israel et al. |
| 5,855,614 A | 1/1999 | Stevens et al. |
| 5,876,373 A | 3/1999 | Giba et al. |
| 5,935,098 A | 8/1999 | Blaisdell |
| 5,957,953 A | 9/1999 | DiPoto |
| 5,961,440 A | 10/1999 | Schweich et al. |
| 5,961,539 A | 10/1999 | Northrup, III et al. |
| 5,984,959 A | 11/1999 | Robertson |
| 6,042,554 A | 3/2000 | Rosenman |
| 6,045,497 A | 4/2000 | Schweich et al. |
| 6,050,936 A | 4/2000 | Schweich et al. |
| 6,059,715 A | 5/2000 | Schweich et al. |
| 6,074,401 A | 6/2000 | Gardiner et al. |
| 6,074,417 A | 6/2000 | Peredo |
| 6,102,945 A | 8/2000 | Campbell |
| 6,106,550 A | 8/2000 | Magovern |
| 6,110,200 A | 8/2000 | Hinnenkamp |
| 6,143,024 A | 11/2000 | Campbell |
| 6,159,240 A | 12/2000 | Sparer |
| 6,165,119 A | 12/2000 | Schweich et al. |
| 6,174,332 B1 | 1/2001 | Loch |
| 6,183,411 B1 | 2/2001 | Mortier |
| 6,187,040 B1 | 2/2001 | Wright |
| 6,315,784 B1 | 2/2001 | Djurovic |
| 6,217,610 B1 | 4/2001 | Carpentier |
| 6,231,602 B1 | 5/2001 | Carpentier |
| 6,251,092 B1 | 6/2001 | Qin et al. |
| 6,296,656 B1 | 10/2001 | Bodluc et al. |
| 6,319,281 B1 | 11/2001 | Patel |
| 6,332,893 B1 | 12/2001 | Mortier et al. |
| 6,355,030 B1 | 3/2002 | Aldrich et al. |
| 6,368,348 B1 | 4/2002 | Gabbay |
| 6,402,780 B2 | 6/2002 | Williamson, IV |
| 6,406,420 B1 | 6/2002 | McCarthy et al. |
| 6,406,493 B1 | 6/2002 | Tu |
| 6,419,696 B1 | 7/2002 | Ortiz et al. |
| 6,451,054 B1 | 9/2002 | Stevens |
| 6,461,366 B1 | 10/2002 | Seguin |
| 6,470,892 B1 | 10/2002 | Forsell |
| 6,503,274 B1 | 1/2003 | Howanec |
| 6,524,338 B1 | 2/2003 | Gundry |
| 6,533,772 B1 | 3/2003 | Sherts et al. |
| 6,537,314 B2 | 3/2003 | Langberg et al. |
| 6,547,801 B1 | 4/2003 | Dargent |
| 6,554,845 B1 | 4/2003 | Fleenor |
| 6,564,805 B2 | 5/2003 | Garrison et al. |
| 6,565,603 B2 | 5/2003 | Cox |
| 6,569,198 B1 | 5/2003 | Wilson et al. |
| 6,579,297 B2 | 6/2003 | Bicek et al. |
| 6,589,160 B2 | 7/2003 | Schweich et al. |
| 6,602,288 B1 | 8/2003 | Cosgrove |
| 6,602,289 B1 | 8/2003 | Colvin et al. |
| 6,613,078 B1 | 9/2003 | Barone |
| 6,613,079 B1 | 9/2003 | Wolinsky et al. |
| 6,619,291 B2 | 9/2003 | Hlavka et al. |
| 6,626,899 B2 | 9/2003 | Houser et al. |
| 6,626,917 B1 | 9/2003 | Craig |
| 6,626,930 B1 | 9/2003 | Allen et al. |
| 6,629,534 B1 | 10/2003 | St. Goar et al. |
| 6,629,921 B1 | 10/2003 | Schweich et al. |
| 6,651,671 B1 | 11/2003 | Donlon et al. |
| 6,652,556 B1 | 11/2003 | VanTasel |
| 6,682,558 B2 | 1/2004 | Tu et al. |
| 6,689,125 B1 | 2/2004 | Keith et al. |
| 6,689,164 B1 | 2/2004 | Seguin |
| 6,695,866 B1 | 2/2004 | Kuehn et al. |
| 6,702,826 B2 | 3/2004 | Liddicoat et al. |
| 6,702,846 B2 | 3/2004 | Mikus et al. |
| 6,706,065 B2 | 3/2004 | Langberg |
| 6,709,385 B2 | 3/2004 | Forsell |
| 6,709,456 B2 | 3/2004 | Langberg et al. |
| 6,711,444 B2 | 3/2004 | Koblish |
| 6,718,985 B2 | 4/2004 | Hlavka et al. |
| 6,719,786 B2 | 4/2004 | Ryan |
| 6,723,038 B1 | 4/2004 | Schroeder et al. |
| 6,726,716 B2 | 4/2004 | Marquez |
| 6,726,717 B2 | 4/2004 | Alfieri et al. |
| 6,730,121 B2 | 5/2004 | Ortiz et al. |
| 6,749,630 B2 | 6/2004 | McCarthy et al. |
| 6,752,813 B2 | 6/2004 | Goldfarb et al. |
| 6,764,310 B1 | 7/2004 | Ichihashi et al. |

(56) References Cited

U.S. PATENT DOCUMENTS

| | | |
|---|---|---|
| 6,764,510 B2 | 7/2004 | Vidlund et al. |
| 6,764,810 B2 | 7/2004 | Ma et al. |
| 6,770,083 B2 | 8/2004 | Seguin |
| 6,786,924 B2 | 9/2004 | Ryan et al. |
| 6,786,925 B1 | 9/2004 | Schoon |
| 6,790,231 B2 | 9/2004 | Liddicoat |
| 6,797,001 B2 | 9/2004 | Mathis |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |
| 6,855,126 B2 | 2/2005 | Flinchbaugh |
| 6,858,039 B2 | 2/2005 | McCarthy |
| 6,880,699 B2 * | 4/2005 | Gallagher .......... A61B 17/1222 206/339 |
| 6,884,250 B2 | 4/2005 | Monassevitch et al. |
| 6,893,459 B1 | 5/2005 | Macoviak |
| 6,908,482 B2 | 6/2005 | McCarthy et al. |
| 6,918,917 B1 | 7/2005 | Nguyen et al. |
| 6,926,730 B1 | 8/2005 | Nguyen et al. |
| 6,960,217 B2 | 11/2005 | Bolduc |
| 6,964,684 B2 | 11/2005 | Ortiz |
| 6,964,686 B2 | 11/2005 | Gordon |
| 6,976,995 B2 | 12/2005 | Mathis |
| 6,986,775 B2 | 1/2006 | Morales et al. |
| 6,989,028 B2 | 1/2006 | Lashinski et al. |
| 6,997,951 B2 | 2/2006 | Solem |
| 7,004,176 B2 | 2/2006 | Lau |
| 7,011,669 B2 | 3/2006 | Kimblad |
| 7,011,682 B2 | 3/2006 | Lashinski et al. |
| 7,037,334 B1 | 5/2006 | Hlavka et al. |
| 7,077,850 B2 | 7/2006 | Kortenbach |
| 7,077,862 B2 | 7/2006 | Vidlund |
| 7,087,064 B1 | 8/2006 | Hyde |
| 7,101,395 B2 | 9/2006 | Tremulis |
| 7,101,396 B2 | 9/2006 | Artof et al. |
| 7,112,207 B2 | 9/2006 | Allen et al. |
| 7,118,595 B2 | 10/2006 | Ryan |
| 7,125,421 B2 | 10/2006 | Tremulis et al. |
| 7,150,737 B2 | 12/2006 | Purdy et al. |
| 7,159,593 B2 | 1/2007 | McCarthy |
| 7,166,127 B2 | 1/2007 | Spence |
| 7,169,187 B2 | 1/2007 | Datta et al. |
| 7,172,625 B2 | 2/2007 | Shu et al. |
| 7,175,660 B2 | 2/2007 | Cartledge et al. |
| 7,186,262 B2 | 3/2007 | Saadat |
| 7,186,264 B2 | 3/2007 | Liddicoat |
| 7,189,199 B2 | 3/2007 | McCarthy et al. |
| 7,192,443 B2 | 3/2007 | Solem |
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,288,097 B2 | 10/2007 | Seguin |
| 7,294,148 B2 | 11/2007 | McCarthy |
| 7,297,150 B2 | 11/2007 | Cartledge et al. |
| 7,311,728 B2 | 12/2007 | Solem et al. |
| 7,311,729 B2 | 12/2007 | Mathis |
| 5,474,518 A1 | 1/2008 | Farrer Velazquez |
| 7,314,485 B2 | 1/2008 | Mathis |
| 7,316,710 B1 | 1/2008 | Cheng et al. |
| 7,329,279 B2 | 2/2008 | Haug et al. |
| 7,329,280 B2 | 2/2008 | Bolling et al. |
| 7,335,213 B1 | 2/2008 | Hyde et al. |
| 7,361,190 B2 | 4/2008 | Shoulian |
| 7,364,588 B2 | 4/2008 | Mathis |
| 7,377,941 B2 | 5/2008 | Rhee |
| 7,390,329 B2 | 6/2008 | Westra et al. |
| 7,404,824 B1 | 7/2008 | Webler et al. |
| 7,431,692 B2 | 10/2008 | Zollinger et al. |
| 7,442,207 B2 | 10/2008 | Rafiee |
| 7,452,376 B2 | 11/2008 | Lim et al. |
| 7,455,690 B2 | 11/2008 | Cartledge et al. |
| 7,485,142 B2 | 2/2009 | Milo |
| 7,485,143 B2 | 2/2009 | Webler et al. |
| 7,500,989 B2 | 3/2009 | Solem et al. |
| 7,507,252 B2 | 3/2009 | Lashinski et al. |
| 7,510,575 B2 | 3/2009 | Spenser et al. |
| 7,510,577 B2 | 3/2009 | Moaddeb |
| 7,527,647 B2 | 5/2009 | Spence |
| 7,530,995 B2 | 5/2009 | Quijano |
| 7,549,983 B2 | 6/2009 | Roue et al. |
| 7,559,936 B2 | 7/2009 | Levine |
| 7,562,660 B2 | 7/2009 | Saadat |
| 7,563,267 B2 | 7/2009 | Goldfarb et al. |
| 7,563,273 B2 | 7/2009 | Goldfarb et al. |
| 7,569,062 B1 | 8/2009 | Kuehn |
| 7,588,582 B2 | 9/2009 | Starksen et al. |
| 7,591,826 B2 | 9/2009 | Alferness |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,618,449 B2 | 11/2009 | Tremulis et al. |
| 7,625,403 B2 | 12/2009 | Krivoruchko |
| 7,632,303 B1 | 12/2009 | Stalker et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,666,204 B2 | 2/2010 | Thornton |
| 7,682,319 B2 | 3/2010 | Martin |
| 7,682,369 B2 | 3/2010 | Seguin |
| 7,686,822 B2 | 3/2010 | Shayani |
| 7,699,892 B2 | 4/2010 | Rafiee |
| 7,704,269 B2 | 4/2010 | Goar |
| 7,704,277 B2 | 4/2010 | Zakay et al. |
| 7,722,666 B2 | 5/2010 | Lafontaine |
| 7,736,388 B2 | 6/2010 | Goldfarb et al. |
| 7,748,389 B2 | 7/2010 | Salahieh et al. |
| 7,753,924 B2 | 7/2010 | Starksen et al. |
| 7,758,632 B2 | 7/2010 | Hojeibane et al. |
| 7,780,726 B2 | 8/2010 | Seguin |
| 7,871,368 B2 | 1/2011 | Zollinger et al. |
| 7,871,433 B2 | 1/2011 | Lattouf |
| 7,883,475 B2 | 2/2011 | Dupont et al. |
| 7,883,538 B2 | 2/2011 | To et al. |
| 7,927,370 B2 | 4/2011 | Webler et al. |
| 7,927,371 B2 | 4/2011 | Navia |
| 7,942,927 B2 | 5/2011 | Kaye et al. |
| 7,947,056 B2 | 5/2011 | Griego et al. |
| 7,955,377 B2 | 6/2011 | Melsheimer |
| 7,988,725 B2 | 8/2011 | Gross |
| 7,992,567 B2 | 8/2011 | Hirotsuka |
| 7,993,368 B2 | 8/2011 | Gambale et al. |
| 7,993,397 B2 | 8/2011 | Lashinski |
| 8,012,201 B2 | 9/2011 | Lashinski et al. |
| 8,034,103 B2 | 10/2011 | Burriesci |
| 8,052,592 B2 | 11/2011 | Goldfarb et al. |
| 8,057,493 B2 | 11/2011 | Goldfarb et al. |
| 8,062,355 B2 | 11/2011 | Figulla et al. |
| 8,070,804 B2 | 12/2011 | Hyde |
| 8,070,805 B2 | 12/2011 | Vidlund |
| 8,075,616 B2 | 12/2011 | Solem |
| 8,100,964 B2 | 1/2012 | Spence |
| 8,123,800 B2 | 2/2012 | McCarthy |
| 8,123,801 B2 | 2/2012 | Milo |
| 8,323,334 B2 | 2/2012 | Deem |
| 8,142,493 B2 | 3/2012 | Spence et al. |
| 8,142,495 B2 | 3/2012 | Hasenkam |
| 8,142,496 B2 | 3/2012 | Berreklouw |
| 8,147,542 B2 | 4/2012 | Maisano et al. |
| 8,152,844 B2 | 4/2012 | Rao |
| 8,163,013 B2 | 4/2012 | Machold |
| 8,187,299 B2 | 5/2012 | Goldfarb et al. |
| 8,187,324 B2 | 5/2012 | Webler |
| 8,202,315 B2 | 6/2012 | Hlavka |
| 8,206,439 B2 | 6/2012 | Gomez-Duran |
| 8,216,302 B2 | 7/2012 | Wilson et al. |
| 8,226,711 B2 | 7/2012 | Mortier |
| 8,231,671 B2 | 7/2012 | Kim |
| 8,241,351 B2 | 8/2012 | Cabiri |
| 8,252,050 B2 | 8/2012 | Maisano et al. |
| 8,262,725 B2 | 9/2012 | Subramanian |

(56) References Cited

U.S. PATENT DOCUMENTS

| | | |
|---|---|---|
| 8,277,502 B2 | 10/2012 | Miller |
| 8,287,584 B2 | 10/2012 | Salahieh |
| 8,287,591 B2 | 10/2012 | Keidar |
| 8,303,608 B2 | 11/2012 | Goldfarb et al. |
| 8,328,868 B2 | 12/2012 | Paul |
| 8,333,777 B2 | 12/2012 | Schaller |
| 8,343,173 B2 | 1/2013 | Starksen et al. |
| 8,343,174 B2 | 1/2013 | Goldfarb |
| 8,343,213 B2 | 1/2013 | Salahieh et al. |
| 8,349,002 B2 | 1/2013 | Milo |
| 8,353,956 B2 | 1/2013 | Miller et al. |
| 8,357,195 B2 | 1/2013 | Kuehn |
| 8,382,829 B1 | 2/2013 | Call et al. |
| 8,388,680 B2 | 3/2013 | Starksen et al. |
| 8,393,517 B2 | 3/2013 | Milo |
| 8,430,926 B2 | 4/2013 | Kirson |
| 8,449,599 B2 | 5/2013 | Chau et al. |
| 8,454,686 B2 | 6/2013 | Alkhatib |
| 8,460,370 B2 | 6/2013 | Zakay et al. |
| 8,460,371 B2 | 6/2013 | Hlavka et al. |
| 8,475,491 B2 | 7/2013 | Milo |
| 8,480,732 B2 | 7/2013 | Subramanian |
| 8,500,800 B2 | 8/2013 | Maisano et al. |
| 8,518,107 B2 | 8/2013 | Tsukashima et al. |
| 8,523,881 B2 | 9/2013 | Cabiri |
| 8,523,940 B2 | 9/2013 | Richardson |
| 8,545,553 B2 | 10/2013 | Zipory |
| 8,551,161 B2 | 10/2013 | Dolan |
| 8,585,755 B2 | 11/2013 | Chau et al. |
| 8,591,576 B2 | 11/2013 | Hasenkam |
| 8,608,797 B2 | 12/2013 | Gross |
| 8,628,569 B2 | 1/2014 | Benichou et al. |
| 8,628,571 B1 | 1/2014 | Hacohen et al. |
| 8,641,727 B2 | 2/2014 | Starksen et al. |
| 8,652,202 B2 | 2/2014 | Alon et al. |
| 8,652,203 B2 | 2/2014 | Quadri et al. |
| 8,679,174 B2 | 3/2014 | Ottma et al. |
| 8,685,086 B2 | 4/2014 | Navia et al. |
| 8,690,939 B2 | 4/2014 | Miller et al. |
| 8,715,342 B2 | 5/2014 | Zipory et al. |
| 8,728,097 B1 | 5/2014 | Sugimoto et al. |
| 8,728,155 B2 | 5/2014 | Montorfano et al. |
| 8,734,467 B2 | 5/2014 | Miller et al. |
| 8,740,920 B2 | 6/2014 | Goldfarb et al. |
| 8,747,463 B2 | 6/2014 | Fogarty et al. |
| 8,778,021 B2 | 7/2014 | Cartledge |
| 8,784,481 B2 | 7/2014 | Alkhatib et al. |
| 8,790,367 B2 | 7/2014 | Nguyen et al. |
| 8,790,394 B2 | 7/2014 | Miller et al. |
| 8,795,298 B2 | 8/2014 | Hernlund et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,808,366 B2 | 8/2014 | Braido et al. |
| 8,808,368 B2 | 8/2014 | Maisano et al. |
| 8,808,371 B2 | 8/2014 | Cartledge |
| 8,845,717 B2 | 9/2014 | Khairkhahan et al. |
| 8,845,723 B2 | 9/2014 | Spence et al. |
| 8,852,261 B2 | 10/2014 | White |
| 8,852,272 B2 | 10/2014 | Gross et al. |
| 8,858,623 B2 | 10/2014 | Miller et al. |
| 8,864,822 B2 | 10/2014 | Spence et al. |
| 8,870,948 B1 | 10/2014 | Erzberger et al. |
| 8,870,949 B2 | 10/2014 | Rowe |
| 8,888,843 B2 | 11/2014 | Khairkhahan et al. |
| 8,894,702 B2 | 11/2014 | Quadri et al. |
| 8,911,461 B2 | 12/2014 | Traynor et al. |
| 8,911,494 B2 | 12/2014 | Hammer et al. |
| 8,926,695 B2 | 1/2015 | Gross et al. |
| 8,926,696 B2 | 1/2015 | Cabin et al. |
| 8,926,697 B2 | 1/2015 | Gross et al. |
| 8,932,343 B2 | 1/2015 | Alkhatib et al. |
| 8,932,348 B2 | 1/2015 | Solem et al. |
| 8,940,042 B2 | 1/2015 | Miller et al. |
| 8,940,044 B2 | 1/2015 | Hammer et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,595 B2 | 2/2015 | Alkhatib |
| 8,961,602 B2 | 2/2015 | Kovach et al. |
| 8,979,922 B2 | 3/2015 | Jayasinghe et al. |
| 9,005,273 B2 | 4/2015 | Salahieh et al. |
| 9,011,520 B2 | 4/2015 | Miller et al. |
| 9,011,530 B2 | 4/2015 | Reich et al. |
| 9,017,399 B2 | 4/2015 | Gross et al. |
| 9,023,100 B2 | 5/2015 | Quadri et al. |
| 9,034,032 B2 | 5/2015 | McLean et al. |
| 9,072,603 B2 | 7/2015 | Tuval et al. |
| 9,107,749 B2 | 8/2015 | Bobo et al. |
| 9,119,719 B2 | 9/2015 | Zipory et al. |
| 9,125,632 B2 | 9/2015 | Loulmet et al. |
| 9,125,742 B2 | 9/2015 | Yoganathan et al. |
| 9,173,646 B2 | 11/2015 | fabro |
| 9,180,005 B1 | 11/2015 | Lashinski et al. |
| 9,180,007 B2 | 11/2015 | Reich et al. |
| 9,192,472 B2 | 11/2015 | Gross et al. |
| 9,226,825 B2 | 1/2016 | Starksen et al. |
| 9,241,702 B2 | 1/2016 | Maisano et al. |
| 9,265,608 B2 | 2/2016 | Miller et al. |
| 9,326,857 B2 | 5/2016 | Cartledge et al. |
| 9,351,830 B2 | 5/2016 | Gross et al. |
| 9,414,921 B2 | 8/2016 | Miller et al. |
| 9,427,316 B2 | 8/2016 | Schweich et al. |
| 9,474,606 B2 | 10/2016 | Zipory et al. |
| 9,526,613 B2 | 12/2016 | Gross et al. |
| 9,561,104 B2 | 2/2017 | Miller et al. |
| 2001/0021874 A1 | 9/2001 | Carpentier |
| 2001/0044656 A1 | 11/2001 | Williamson |
| 2002/0022862 A1 | 2/2002 | Grafton et al. |
| 2002/0029080 A1 | 3/2002 | Mortier |
| 2002/0042621 A1 | 4/2002 | Liddicoat |
| 2002/0082525 A1 | 6/2002 | Oslund et al. |
| 2002/0087048 A1 | 7/2002 | Brock et al. |
| 2002/0103532 A1 | 8/2002 | Langberg et al. |
| 2002/0133180 A1 | 9/2002 | Ryan et al. |
| 2002/0151916 A1 | 10/2002 | Muramatsu |
| 2002/0151961 A1 | 10/2002 | Lashinski |
| 2002/0151970 A1 | 10/2002 | Garrison |
| 2002/0169358 A1 | 11/2002 | Mortier et al. |
| 2002/0173841 A1 | 11/2002 | Ortiz et al. |
| 2002/0177904 A1 | 11/2002 | Huxel et al. |
| 2002/0188301 A1 | 12/2002 | Dallara et al. |
| 2002/0198586 A1 | 12/2002 | Inoue |
| 2003/0018358 A1 | 1/2003 | Saadat |
| 2003/0050693 A1 | 3/2003 | Quijano et al. |
| 2003/0078465 A1 | 4/2003 | Pai et al. |
| 2003/0078653 A1 | 4/2003 | Vesely |
| 2003/0083742 A1 | 5/2003 | Spence |
| 2003/0100943 A1 | 5/2003 | Bolduc |
| 2003/0105519 A1 | 6/2003 | Fasol et al. |
| 2003/0114901 A1 | 6/2003 | Loeb et al. |
| 2003/0120340 A1 | 6/2003 | Liska et al. |
| 2003/0130731 A1 | 7/2003 | Vidlund |
| 2003/0144657 A1 | 7/2003 | Bowe et al. |
| 2003/0167062 A1 | 9/2003 | Gambale et al. |
| 2003/0171760 A1 | 9/2003 | Gambale |
| 2003/0191528 A1 | 10/2003 | Quijano et al. |
| 2003/0199974 A1 | 10/2003 | Lee et al. |
| 2003/0204195 A1 | 10/2003 | Keane |
| 2003/0229350 A1 | 12/2003 | Kay |
| 2003/0229395 A1 | 12/2003 | Cox |
| 2003/0233142 A1 | 12/2003 | Morales et al. |
| 2004/0010287 A1 | 1/2004 | Bonutti |
| 2004/0019359 A1 | 1/2004 | Worley et al. |
| 2004/0019377 A1 | 1/2004 | Taylor |
| 2004/0024451 A1 | 2/2004 | Johnson et al. |
| 2004/0039442 A1 | 2/2004 | St. Goar et al. |
| 2004/0049207 A1 | 3/2004 | Goldfarb et al. |
| 2004/0059413 A1 | 3/2004 | Argento |
| 2004/0092962 A1 | 5/2004 | Thornton et al. |
| 2004/0122448 A1 | 6/2004 | Levine |
| 2004/0122514 A1 | 6/2004 | Fogarty et al. |
| 2004/0127982 A1 | 7/2004 | Machold et al. |
| 2004/0127983 A1 | 7/2004 | Mortier et al. |

(56) References Cited

U.S. PATENT DOCUMENTS

| | | |
|---|---|---|
| 2004/0133220 A1 | 7/2004 | Lashinski et al. |
| 2004/0133274 A1 | 7/2004 | Webler |
| 2004/0133374 A1 | 7/2004 | Kattan |
| 2004/0138744 A1 | 7/2004 | Lashinski et al. |
| 2004/0138745 A1 | 7/2004 | Macoviak et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0153146 A1 | 8/2004 | Lashinski et al. |
| 2004/0172046 A1 | 9/2004 | Hlavka |
| 2004/0176788 A1 | 9/2004 | Opolski |
| 2004/0181287 A1 | 9/2004 | Gellman |
| 2004/0186566 A1 | 9/2004 | Hindrichs |
| 2004/0193191 A1 | 9/2004 | Starksen et al. |
| 2004/0236419 A1 | 11/2004 | Milo |
| 2004/0243227 A1 | 12/2004 | Starsken et al. |
| 2004/0249453 A1 | 12/2004 | Cartledge |
| 2004/0260317 A1 | 12/2004 | Bloom et al. |
| 2004/0260393 A1 | 12/2004 | Randert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0010787 A1 | 1/2005 | Tarbouriech |
| 2005/0016560 A1 | 1/2005 | Voughlohn |
| 2005/0055038 A1 | 3/2005 | Kelleher et al. |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070999 A1 | 3/2005 | Spence |
| 2005/0075727 A1 | 4/2005 | Wheatley |
| 2005/0085903 A1 | 4/2005 | Lau |
| 2005/0090827 A1 | 4/2005 | Gedebou |
| 2005/0096740 A1 | 5/2005 | Langberg et al. |
| 2005/0107812 A1 | 5/2005 | Starksen et al. |
| 2005/0107871 A1 | 5/2005 | Realyvasquez et al. |
| 2005/0119734 A1 | 6/2005 | Spence |
| 2005/0125002 A1 | 6/2005 | Baran et al. |
| 2005/0125011 A1 | 6/2005 | Spence et al. |
| 2005/0131533 A1 | 6/2005 | Alfieri |
| 2005/0137686 A1 | 6/2005 | Salahieh et al. |
| 2005/0137688 A1 | 6/2005 | Salahieh et al. |
| 2005/0137695 A1 | 6/2005 | Salahieh |
| 2005/0159728 A1 | 7/2005 | Armour et al. |
| 2005/0171601 A1 | 8/2005 | Cosgrove et al. |
| 2005/0177180 A1 | 8/2005 | Kaganov |
| 2005/0177228 A1 | 8/2005 | Solem et al. |
| 2005/0187613 A1 | 8/2005 | Bolduc et al. |
| 2005/0192596 A1 | 9/2005 | Jugenheimer et al. |
| 2005/0197696 A1 | 9/2005 | Gomez Duran |
| 2005/0203549 A1 | 9/2005 | Realyvasquez |
| 2005/0203606 A1 | 9/2005 | VanCamp |
| 2005/0216036 A1* | 9/2005 | Nakao ................ A61B 17/068 606/142 |
| 2005/0216039 A1 | 9/2005 | Lederman |
| 2005/0216079 A1 | 9/2005 | MaCoviak |
| 2005/0222665 A1 | 10/2005 | Aranyi |
| 2005/0222678 A1 | 10/2005 | Lashinski et al. |
| 2005/0256532 A1 | 11/2005 | Nayak et al. |
| 2005/0267478 A1 | 12/2005 | Corradi et al. |
| 2005/0273138 A1 | 12/2005 | To et al. |
| 2005/0288776 A1 | 12/2005 | Shaoulian et al. |
| 2005/0288778 A1 | 12/2005 | Shaoulian |
| 2005/0288781 A1 | 12/2005 | Moaddeb et al. |
| 2006/0004442 A1 | 1/2006 | Spenser et al. |
| 2006/0004443 A1 | 1/2006 | Liddicoat |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025855 A1 | 2/2006 | Lashinski et al. |
| 2006/0025858 A1 | 2/2006 | Alameddine |
| 2006/0030885 A1 | 2/2006 | Hyde |
| 2006/0041319 A1 | 2/2006 | Taylor et al. |
| 2006/0052868 A1 | 3/2006 | Mortier |
| 2006/0058871 A1 | 3/2006 | Zakay et al. |
| 2006/0069429 A1 | 3/2006 | Spence et al. |
| 2006/0074486 A1 | 4/2006 | Liddicoat |
| 2006/0085012 A1 | 4/2006 | Dolan |
| 2006/0095009 A1 | 5/2006 | Lampropoulos |
| 2006/0106423 A1 | 5/2006 | Weisel |
| 2006/0116757 A1 | 6/2006 | Lashinski et al. |
| 2006/0122633 A1 | 6/2006 | To |
| 2006/0129166 A1 | 6/2006 | Lavelle |
| 2006/0149280 A1 | 7/2006 | Harvine et al. |
| 2006/0149368 A1 | 7/2006 | Spence |
| 2006/0161265 A1 | 7/2006 | Levine et al. |
| 2006/0184240 A1 | 8/2006 | Jiminez |
| 2006/0184242 A1 | 8/2006 | Lichtenstein |
| 2006/0195134 A1 | 8/2006 | Crittenden |
| 2006/0241622 A1 | 10/2006 | Zergiebel |
| 2006/0241656 A1 | 10/2006 | Starksen et al. |
| 2006/0241748 A1 | 10/2006 | Lee et al. |
| 2006/0247763 A1 | 11/2006 | Slater |
| 2006/0259135 A1 | 11/2006 | Navia |
| 2006/0271175 A1 | 11/2006 | Woolfson |
| 2006/0282161 A1 | 12/2006 | Huyn et al. |
| 2006/0287661 A1 | 12/2006 | Bolduc |
| 2006/0287716 A1 | 12/2006 | Banbury et al. |
| 2007/0001627 A1 | 1/2007 | Lin et al. |
| 2007/0016287 A1 | 1/2007 | Cartledge et al. |
| 2007/0016288 A1 | 1/2007 | Gurskis |
| 2007/0021781 A1 | 1/2007 | Jervis |
| 2007/0027533 A1 | 2/2007 | Douk |
| 2007/0027536 A1 | 2/2007 | Mihaljevic et al. |
| 2007/0038221 A1 | 2/2007 | Fine |
| 2007/0039425 A1 | 2/2007 | Wang |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0080188 A1 | 4/2007 | Spence et al. |
| 2007/0083168 A1 | 4/2007 | Whiting et al. |
| 2007/0100427 A1 | 5/2007 | Perouse |
| 2007/0106328 A1 | 5/2007 | Wardle et al. |
| 2007/0112359 A1* | 5/2007 | Kimura ................ A61B 17/122 606/142 |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0119871 A1* | 5/2007 | Garcia ................ A61B 17/865 222/325 |
| 2007/0142907 A1 | 6/2007 | Moaddeb |
| 2007/0162111 A1 | 7/2007 | Fukamachi et al. |
| 2007/0198082 A1 | 8/2007 | Kapadia et al. |
| 2007/0213582 A1 | 9/2007 | Zollinger et al. |
| 2007/0219558 A1 | 9/2007 | Deutsch |
| 2007/0233239 A1 | 10/2007 | Navia et al. |
| 2007/0239208 A1 | 10/2007 | Crawford |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255397 A1 | 11/2007 | Ryan et al. |
| 2007/0255400 A1 | 11/2007 | Parravicini et al. |
| 2007/0270755 A1 | 11/2007 | Von Oepen et al. |
| 2007/0270943 A1 | 11/2007 | Solem et al. |
| 2007/0276437 A1 | 11/2007 | Call |
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2007/0299424 A1 | 12/2007 | Cumming et al. |
| 2008/0004697 A1 | 1/2008 | Lichtenstein et al. |
| 2008/0027483 A1 | 1/2008 | Cartledge |
| 2008/0027555 A1 | 1/2008 | Hawkins |
| 2008/0035160 A1 | 2/2008 | Wodson et al. |
| 2008/0039935 A1 | 2/2008 | Buch |

(56) References Cited

U.S. PATENT DOCUMENTS

| | | |
|---|---|---|
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065204 A1 | 3/2008 | Mackoviak |
| 2008/0071366 A1 | 3/2008 | Tuval |
| 2008/0086138 A1 | 4/2008 | Stone et al. |
| 2008/0086203 A1 | 4/2008 | Roberts |
| 2008/0091257 A1 | 4/2008 | Andreas et al. |
| 2008/0097523 A1 | 4/2008 | Bolduc et al. |
| 2008/0103572 A1 | 5/2008 | Gerber |
| 2008/0125861 A1 | 5/2008 | Webler et al. |
| 2008/0140116 A1 | 6/2008 | Bonutti |
| 2008/0167714 A1 | 7/2008 | St. Goar |
| 2008/0177382 A1 | 7/2008 | Hyde et al. |
| 2008/0195126 A1 | 8/2008 | Solem |
| 2008/0195200 A1 | 8/2008 | Vidlund |
| 2008/0208265 A1 | 8/2008 | Frazier et al. |
| 2008/0221672 A1 | 9/2008 | Lamphere |
| 2008/0243245 A1 | 10/2008 | Thambar |
| 2008/0262480 A1 | 10/2008 | Stahler et al. |
| 2008/0262609 A1 | 10/2008 | Gross et al. |
| 2008/0275300 A1 | 11/2008 | Rothe |
| 2008/0275469 A1 | 11/2008 | Fanton |
| 2008/0275551 A1 | 11/2008 | Alfieri |
| 2008/0281411 A1 | 11/2008 | Berreklouw |
| 2008/0288044 A1 | 11/2008 | Osborne |
| 2008/0288062 A1 | 11/2008 | Andrieu et al. |
| 2008/0300537 A1 | 12/2008 | Bowman |
| 2008/0300629 A1 | 12/2008 | Surti |
| 2009/0028670 A1 | 1/2009 | Garcia et al. |
| 2009/0043153 A1 | 2/2009 | Zollinger et al. |
| 2009/0043381 A1 | 2/2009 | Macoviak |
| 2009/0054969 A1 | 2/2009 | Salahieh |
| 2009/0062866 A1 | 3/2009 | Jackson |
| 2009/0076586 A1 | 3/2009 | Hauser |
| 2009/0076600 A1 | 3/2009 | Quinn |
| 2009/0088837 A1 | 4/2009 | Gillinov |
| 2009/0093877 A1 | 4/2009 | Keidar et al. |
| 2009/0099650 A1 | 4/2009 | Bolduc |
| 2009/0105816 A1 | 4/2009 | Olsen et al. |
| 2009/0125102 A1 | 5/2009 | Cartledge |
| 2009/0149872 A1 | 6/2009 | Gross et al. |
| 2009/0177274 A1 | 6/2009 | Scorsin |
| 2009/0171439 A1 | 7/2009 | Nissl |
| 2009/0177266 A1 | 7/2009 | Powell et al. |
| 2009/0177277 A1 | 7/2009 | Milo |
| 2009/0222083 A1 | 9/2009 | Nguyen et al. |
| 2009/0248148 A1 | 10/2009 | Shaolian |
| 2009/0254103 A1 | 10/2009 | Deustch |
| 2009/0259307 A1 | 10/2009 | Gross et al. |
| 2009/0264994 A1 | 10/2009 | Saadat |
| 2009/0264995 A1 | 10/2009 | Subramanian |
| 2009/0287231 A1 | 11/2009 | Brooks et al. |
| 2009/0287304 A1 | 11/2009 | Dahlgren |
| 2009/0299409 A1 | 12/2009 | Coe |
| 2009/0326648 A1 | 12/2009 | Machold et al. |
| 2010/0001038 A1 | 1/2010 | Levin |
| 2010/0010538 A1 | 1/2010 | Juravic |
| 2010/0023117 A1 | 1/2010 | Yoganathan |
| 2010/0023118 A1 | 1/2010 | Medlock et al. |
| 2010/0030014 A1 | 2/2010 | Ferrazzi |
| 2010/0030328 A1 | 2/2010 | Seguin |
| 2010/0042147 A1 | 2/2010 | Janovsky et al. |
| 2010/0049313 A1 | 2/2010 | Alon et al. |
| 2010/0063542 A1 | 3/2010 | Van der Burg |
| 2010/0063550 A1 | 3/2010 | Felix |
| 2010/0063586 A1 | 3/2010 | Hasenkam |
| 2010/0065456 A1* | 3/2010 | Junk .................. A61L 2/26 206/363 |
| 2010/0076499 A1 | 3/2010 | McNamara et al. |
| 2010/0094248 A1 | 4/2010 | Nguyen et al. |
| 2010/0114180 A1 | 5/2010 | Rock |
| 2010/0121349 A1 | 5/2010 | Meier |
| 2010/0121435 A1 | 5/2010 | Subramanian et al. |
| 2010/0121437 A1 | 5/2010 | Subramanian et al. |
| 2010/0130992 A1 | 5/2010 | Machold et al. |
| 2010/0152845 A1 | 6/2010 | Bloom |
| 2010/0161041 A1 | 6/2010 | Maisano et al. |
| 2010/0161042 A1 | 6/2010 | Maisano et al. |
| 2010/0161043 A1 | 6/2010 | Maisano et al. |
| 2010/0161047 A1 | 6/2010 | Cabiri |
| 2010/0168845 A1 | 7/2010 | Wright |
| 2010/0174358 A1 | 7/2010 | Rabkin et al. |
| 2010/0179574 A1 | 7/2010 | Longoria |
| 2010/0198347 A1 | 8/2010 | Zakay et al. |
| 2010/0211166 A1 | 8/2010 | Miller et al. |
| 2010/0217184 A1 | 8/2010 | Koblish et al. |
| 2010/0217382 A1 | 8/2010 | Chau |
| 2010/0234935 A1 | 9/2010 | Bashiri et al. |
| 2010/0249915 A1 | 9/2010 | Zhang |
| 2010/0249920 A1 | 9/2010 | Bolling |
| 2010/0262232 A1 | 10/2010 | Annest |
| 2010/0262233 A1 | 10/2010 | He |
| 2010/0280603 A1 | 11/2010 | Maisano et al. |
| 2010/0280604 A1 | 11/2010 | Zipory |
| 2010/0280605 A1 | 11/2010 | Hammer |
| 2010/0286628 A1 | 11/2010 | Gross |
| 2010/0286767 A1 | 11/2010 | Zipory |
| 2010/0305475 A1 | 12/2010 | Hinchliffe et al. |
| 2010/0324598 A1 | 12/2010 | Anderson |
| 2011/0004210 A1 | 1/2011 | Johnson |
| 2011/0004298 A1 | 1/2011 | Lee et al. |
| 2011/0009956 A1 | 1/2011 | Cartledge et al. |
| 2011/0011917 A1 | 1/2011 | Loulmet |
| 2011/0026208 A1 | 2/2011 | Otsuro et al. |
| 2011/0029066 A1 | 2/2011 | Gilad |
| 2011/0035000 A1 | 2/2011 | Nieminen et al. |
| 2011/0066231 A1 | 3/2011 | Cartledge |
| 2011/0067770 A1 | 3/2011 | Pederson et al. |
| 2011/0071626 A1 | 3/2011 | Wright et al. |
| 2011/0082538 A1 | 4/2011 | Dahlgren et al. |
| 2011/0087146 A1 | 4/2011 | Ryan et al. |
| 2011/0093002 A1 | 4/2011 | Rucker et al. |
| 2011/0106245 A1 | 5/2011 | Miller et al. |
| 2011/0106247 A1 | 5/2011 | Miller |
| 2011/0118832 A1 | 5/2011 | Punjabi |
| 2011/0137410 A1 | 6/2011 | Hacohen |
| 2011/0144703 A1 | 6/2011 | Krause |
| 2011/0166649 A1 | 7/2011 | Gross |
| 2011/0184510 A1 | 7/2011 | Maisano et al. |
| 2011/0190879 A1 | 8/2011 | Bobo et al. |
| 2011/0202130 A1 | 8/2011 | Cartledge |
| 2011/0208283 A1 | 8/2011 | Rust |
| 2011/0224785 A1 | 9/2011 | Hacohen |
| 2011/0230941 A1 | 9/2011 | Markus |
| 2011/0230961 A1 | 9/2011 | Langer |
| 2011/0238088 A1 | 9/2011 | Bolduc et al. |
| 2011/0257433 A1 | 10/2011 | Walker |
| 2011/0257633 A1 | 10/2011 | Cartledge |
| 2011/0257728 A1 | 10/2011 | Kuehn |
| 2011/0264208 A1 | 10/2011 | Duffy |
| 2011/0276062 A1 | 11/2011 | Bolduc |
| 2011/0282361 A1 | 11/2011 | Miller et al. |
| 2011/0288435 A1 | 11/2011 | Christy et al. |
| 2011/0288635 A1 | 11/2011 | Miller |
| 2011/0301498 A1 | 12/2011 | Maenhout et al. |
| 2011/0301698 A1 | 12/2011 | Miller et al. |
| 2012/0022557 A1 | 1/2012 | Cabiri |
| 2012/0022639 A1 | 1/2012 | Hacohen et al. |
| 2012/0022640 A1 | 1/2012 | Gross et al. |
| 2012/0022644 A1 | 1/2012 | Reich |
| 2012/0035712 A1 | 2/2012 | Maisano et al. |
| 2012/0078355 A1 | 3/2012 | Zipory |
| 2012/0078359 A1 | 3/2012 | Li et al. |
| 2012/0089022 A1 | 4/2012 | House et al. |
| 2012/0095552 A1 | 4/2012 | Spence |
| 2012/0109155 A1 | 5/2012 | Robinson et al. |
| 2012/0123531 A1 | 5/2012 | Tsukashima et al. |
| 2012/0136436 A1 | 5/2012 | Cabiri |
| 2012/0143323 A1 | 6/2012 | Hasenkam |
| 2012/0150290 A1 | 6/2012 | Gabbay |
| 2012/0158021 A1 | 6/2012 | Morrill |
| 2012/0179086 A1 | 7/2012 | Shank |
| 2012/0191182 A1 | 7/2012 | Hauser et al. |

(56) References Cited

U.S. PATENT DOCUMENTS

| | | |
|---|---|---|
| 2012/0197388 A1 | 8/2012 | Khairkhahan et al. |
| 2012/0226349 A1 | 9/2012 | Tuval et al. |
| 2012/0239142 A1 | 9/2012 | Liu et al. |
| 2012/0245604 A1 | 9/2012 | Tegzes |
| 2012/0271198 A1 | 10/2012 | Whittaker et al. |
| 2012/0283757 A1 | 11/2012 | Miller |
| 2012/0296349 A1 | 11/2012 | Smith et al. |
| 2012/0296417 A1 | 11/2012 | Hill et al. |
| 2012/0296419 A1 | 11/2012 | Richardson |
| 2012/0310330 A1 | 12/2012 | Buchbinder et al. |
| 2012/0323313 A1 | 12/2012 | Seguin |
| 2012/0330410 A1 | 12/2012 | Hammer |
| 2012/0330411 A1 | 12/2012 | Gross |
| 2013/0023758 A1 | 1/2013 | Fabro |
| 2013/0030522 A1 | 1/2013 | Rowe et al. |
| 2013/0035759 A1 | 2/2013 | Gross et al. |
| 2013/0046373 A1 | 2/2013 | Cartledge et al. |
| 2013/0079873 A1 | 3/2013 | Migliazza |
| 2013/0297013 A1 | 3/2013 | Klima et al. |
| 2013/0085529 A1 | 4/2013 | Housman |
| 2013/0090724 A1 | 4/2013 | Subramanian |
| 2013/0096672 A1 | 4/2013 | Reich |
| 2013/0096673 A1 | 4/2013 | Hill |
| 2013/0116776 A1 | 5/2013 | Gross et al. |
| 2013/0116780 A1 | 5/2013 | Miller |
| 2013/0123910 A1 | 5/2013 | Cartledge |
| 2013/0131791 A1 | 5/2013 | Hlavka et al. |
| 2013/0131792 A1 | 5/2013 | Miller |
| 2013/0166017 A1 | 6/2013 | Cartledge et al. |
| 2013/0172992 A1 | 7/2013 | Gross et al. |
| 2013/0190863 A1 | 7/2013 | Call et al. |
| 2013/0190866 A1 | 7/2013 | Zipory |
| 2013/0197632 A1 | 8/2013 | Kovach |
| 2013/0204361 A1 | 8/2013 | Adams |
| 2013/0226289 A1 | 8/2013 | Shaolian |
| 2013/0226290 A1 | 8/2013 | Yellin et al. |
| 2013/0268069 A1 | 10/2013 | Zakai et al. |
| 2013/0289718 A1 | 10/2013 | Tsukashima et al. |
| 2013/0304093 A1 | 11/2013 | Serina et al. |
| 2013/0325118 A1 | 12/2013 | Cartledge |
| 2014/0018914 A1 | 1/2014 | Zipory et al. |
| 2014/0088368 A1 | 3/2014 | Park |
| 2014/0094826 A1 | 4/2014 | Sutherland et al. |
| 2014/0094903 A1 | 4/2014 | Miller et al. |
| 2014/0094906 A1 | 4/2014 | Spence et al. |
| 2014/0135799 A1 | 5/2014 | Henderson |
| 2014/0142619 A1 | 5/2014 | Serina et al. |
| 2014/0142695 A1 | 5/2014 | Gross et al. |
| 2014/0148849 A1 | 5/2014 | Serina et al. |
| 2014/0148898 A1 | 5/2014 | Gross et al. |
| 2014/0155783 A1 | 6/2014 | Starksen et al. |
| 2014/0163670 A1 | 6/2014 | Alon et al. |
| 2014/0163690 A1 | 6/2014 | White |
| 2014/0188108 A1 | 7/2014 | Goodine et al. |
| 2014/0188140 A1 | 7/2014 | Meier et al. |
| 2014/0188215 A1 | 7/2014 | Hlavka et al. |
| 2014/0194976 A1 | 7/2014 | Starksen et al. |
| 2014/0207231 A1 | 7/2014 | Hacohen et al. |
| 2014/0222137 A1 | 8/2014 | Miller et al. |
| 2014/0243859 A1 | 8/2014 | Robinson |
| 2014/0243894 A1 | 8/2014 | Groothuis et al. |
| 2014/0243963 A1 | 8/2014 | Sheps et al. |
| 2014/0257475 A1 | 9/2014 | Gross et al. |
| 2014/0275757 A1 | 9/2014 | Goodwin et al. |
| 2014/0276648 A1 | 9/2014 | Hammer et al. |
| 2014/0296962 A1 | 10/2014 | Cartledge et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon |
| 2014/0324164 A1 | 10/2014 | Gross et al. |
| 2014/0343668 A1 | 11/2014 | Zipory et al. |
| 2014/0379006 A1 | 12/2014 | Sutherland et al. |
| 2015/0012087 A1 | 1/2015 | Miller et al. |
| 2015/0018940 A1 | 1/2015 | Quill et al. |
| 2015/0051697 A1 | 2/2015 | Spence et al. |
| 2015/0081014 A1 | 3/2015 | Gross et al. |
| 2015/0105855 A1 | 4/2015 | Cabiri et al. |
| 2015/0112432 A1 | 4/2015 | Reich et al. |
| 2015/0127097 A1 | 5/2015 | Neumann et al. |
| 2015/0182336 A1 | 7/2015 | Zipory et al. |
| 2015/0230924 A1 | 8/2015 | Miller |
| 2015/0272586 A1 | 10/2015 | Herman et al. |
| 2015/0272734 A1 | 10/2015 | Sheps et al. |
| 2015/0282931 A1 | 10/2015 | Brunnett et al. |
| 2015/0297212 A1 | 10/2015 | Reich et al. |
| 2015/0351906 A1 | 12/2015 | Hammer et al. |
| 2016/0008132 A1 | 1/2016 | Cabin et al. |
| 2016/0058557 A1 | 3/2016 | Reich et al. |
| 2016/0113767 A1 | 4/2016 | Miller et al. |
| 2016/0158008 A1 | 6/2016 | Miller et al. |
| 2016/0242762 A1 | 8/2016 | Gilmore et al. |
| 2016/0262755 A1 | 9/2016 | Zipory et al. |
| 2016/0302917 A1 | 10/2016 | Schewel |
| 2016/0317302 A1 | 11/2016 | Madjarov et al. |
| 2016/0324633 A1 | 11/2016 | Gross et al. |
| 2016/0361168 A1 | 12/2016 | Gross et al. |
| 2016/0361169 A1 | 12/2016 | Gross et al. |
| 2017/0000609 A1 | 1/2017 | Gross et al. |

FOREIGN PATENT DOCUMENTS

| | | |
|---|---|---|
| EP | 0611561 | 8/1994 |
| EP | 06/14342 | 9/1994 |
| EP | 10/06905 | 6/2000 |
| EP | 0954257 | 8/2000 |
| EP | 1258437 | 11/2002 |
| EP | 0871417 | 10/2003 |
| EP | 1266641 | 10/2004 |
| EP | 1034753 | 2/2005 |
| EP | 1258232 | 1/2006 |
| EP | 1990014 | 11/2008 |
| EP | 1562522 | 12/2008 |
| EP | 1420723 | 1/2009 |
| EP | 1903991 | 9/2009 |
| EP | 1418865 | 10/2009 |
| EP | 2119399 | 11/2009 |
| EP | 1531762 | 4/2010 |
| EP | 1450733 | 2/2011 |
| EP | 1861045 | 3/2015 |
| EP | 1465555 | 5/2015 |
| IL | 223448 | 12/2012 |
| WO | 92/05093 | 4/1992 |
| WO | 93/10714 | 6/1993 |
| WO | 1993/015690 | 8/1993 |
| WO | 96/39963 | 12/1996 |
| WO | 96/40344 | 12/1996 |
| WO | 97/01369 | 1/1997 |
| WO | 98/46149 | 10/1998 |
| WO | 1999/030647 | 6/1999 |
| WO | 99/033414 | 7/1999 |
| WO | 99/063907 | 12/1999 |
| WO | 99/063910 | 12/1999 |
| WO | 2000/009048 | 2/2000 |
| WO | 00/22981 | 4/2000 |
| WO | 01/26586 | 4/2001 |
| WO | 01/56457 | 8/2001 |
| WO | 2001/087191 | 11/2001 |
| WO | 02/085250 | 10/2002 |
| WO | 02/085251 | 10/2002 |
| WO | 02/085252 | 10/2002 |
| WO | 03/028558 | 4/2003 |
| WO | 03/047467 | 6/2003 |
| WO | 2003/049647 | 6/2003 |
| WO | 2003/105667 | 12/2003 |
| WO | 2004/012583 | 2/2004 |
| WO | 2004/019816 | 3/2004 |
| WO | 2004/019826 | 3/2004 |
| WO | 04/103434 | 12/2004 |
| WO | 05/021063 | 3/2005 |
| WO | 05/046488 | 5/2005 |
| WO | 2005/062931 | 7/2005 |
| WO | 06/012013 | 2/2006 |
| WO | 06/012038 | 2/2006 |

(56) References Cited

FOREIGN PATENT DOCUMENTS

| WO | 06/086434 | 8/2006 |
|---|---|---|
| WO | 06/097931 | 9/2006 |
| WO | 06/105084 | 10/2006 |
| WO | 06/116558 | 11/2006 |
| WO | 07/011799 | 1/2007 |
| WO | 2007/080595 | 7/2007 |
| WO | 07/121314 | 10/2007 |
| WO | 07/136783 | 11/2007 |
| WO | 07/136981 | 11/2007 |
| WO | 2008/014144 | 1/2008 |
| WO | 2008/031103 | 3/2008 |
| WO | 08/068756 | 6/2008 |
| WO | 2009/160631 | 10/2009 |
| WO | 10/004546 | 1/2010 |
| WO | 2010/000454 | 1/2010 |
| WO | 2010/006905 | 1/2010 |
| WO | 2010/044851 | 4/2010 |
| WO | 2010/065274 | 6/2010 |
| WO | 10/073246 | 7/2010 |
| WO | 2010/085649 | 7/2010 |
| WO | 2010/128502 | 11/2010 |
| WO | 2010/128503 | 11/2010 |
| WO | 2010/150178 | 12/2010 |
| WO | 2011/051942 | 5/2011 |
| WO | 11/067770 | 6/2011 |
| WO | 2011/089401 | 7/2011 |
| WO | 2011/089601 | 7/2011 |
| WO | 2011/111047 | 9/2011 |
| WO | 2011/148374 | 12/2011 |
| WO | 2011/154942 | 12/2011 |
| WO | 2012/011108 | 1/2012 |
| WO | 2012/014201 | 2/2012 |
| WO | 2012/068541 | 5/2012 |
| WO | 2012/106346 | 8/2012 |
| WO | 2012/176195 | 12/2012 |
| WO | 2013/021374 | 2/2013 |
| WO | 2013/021375 | 2/2013 |
| WO | 2013/069019 | 5/2013 |
| WO | 2013/078497 | 6/2013 |
| WO | 2013/088327 | 6/2013 |
| WO | 2014/064694 | 5/2014 |
| WO | 2014/064695 | 5/2014 |
| WO | 2014/064964 | 5/2014 |
| WO | 2014/076696 | 5/2014 |
| WO | 2014/087402 | 6/2014 |
| WO | 2014/108903 | 7/2014 |
| WO | 2014/115149 | 7/2014 |
| WO | 2014/195786 | 12/2014 |
| WO | 2015/059699 | 4/2015 |
| WO | 2015/193728 | 12/2015 |
| WO | 2016/059639 | 4/2016 |
| WO | 2016/087934 | 6/2016 |
| WO | 2016/174669 | 11/2016 |

OTHER PUBLICATIONS

Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).
Swain CP et al., "An endoscopically deliverable tissue-transfixing device for securing biosensors in the gastrointestinal tract," Gastrointestinal Endoscopy 40(6): 730-734 (1994).
Odell JA et al., "Early Results o4yf a Simplified Method of Mitral Valve Annuloplasty," Circulation 92:150-154 (1995).
U.S. Appl. No. 60/873,075, filed Dec. 5, 2006.
An International Preliminary Report on Patentability dated Nov. 9, 2011, which issued during the Prosecution of Applicant's PCT/IL2010/000357.
U.S. Appl. No. 60/902,146, filed Feb. 16, 2007.
An International Preliminary Report on Patentability dated Jun. 5, 2012, which issued during the prosecution of Applicant's PCT/IL2010/001024.
U.S. Appl. No. 61/001,013, filed Oct. 29, 2007.
An International Preliminary Report on Patentability dated Nov. 27, 2012, which issued during the prosecution of Applicant's PCT/IL2011/000404.
U.S. Appl. No. 61/132,295, filed Jun. 16, 2008.
Notice of Allowance dated Apr. 27, 2012, which issued during the prosecution of U.S. Appl. No. 12/341,960.
"Two dimensional real-time ultrasonic imaging of the heart and great vessels", Mayo Clin Proc. vol. 53:271-303, 1978.
An Office Action dated Mar. 29, 2011, which issued during the prosecution of U.S. Appl. No. 12/341,960.
An Office Action dated Aug. 2, 2011, which issued during the prosecution of U.S. Appl. No. 12/435,291.
A Restriction Requirement dated Mar. 30, 2012, which issued during the prosecution of U.S. Appl. No. 12/785,717.
An International Search Report and a Written Opinion both dated Jun. 10, 2010, which issued during the prosecution of Applicant's PCT/IL09/01209.
An Office Action dated Jan. 27, 2012, which issued during the prosecution of U.S. Appl. No. 12/548,991.
An Office Action dated Apr. 6, 2010, which issued during the prosecution of Applicant's U.S. Appl. No. 12/484,512.
An Office Action dated Nov. 5, 2012, which issued during the prosecution of U.S. Appl. No. 12/795,026.
Notice of Allowance dated Feb. 19, 2014, which issued during the prosecution of U.S. Appl. No. 12/795,192.
An International Search Report and a Written Opinion both dated Aug. 17, 2010, which issued during the prosecution of Applicant's PCT/IL10/00357.
An Office Action dated Sep. 16, 2009 which issued during the prosecution of U.S. Appl. No. 11/950,930.
Alfieri et al., "An effective technique to correct anterior mitral leaflet prolapse," J Card 14(6):468-470 (1999).
A Restriction Requirement dated Nov. 19, 2012, which issued during the prosecution of U.S. Appl. No. 12/926,673.
Alfieri et al., "The double orifice technique in mitral valve repair: a simple solution for complex problems," Journal of Thoracic Cardiovascular Surgery 122:674-681 (2001).
A Supplementary European Search Report dated Jan. 20, 2015, which issued during the prosecution European Patent Application No. 12803037.6.
An International Preliminary Report on Patentability dated Jun. 29, 2011, which issued during the prosecution of Applicant's PCT/IL2009/001209.
Alfieri, "The edge-to-edge repair of the mitral valve," [Abstract] 6th Annual NewEra Cardiac Care: Innovation & Technology, Heart Surgery Forum pp. 103. (2000).
Dang NC et al. "Simplified Placement of Multiple Artificial Mitral Valve Chords," The Heart Surgery Forum #2005-1005, 8 (3) (2005).
An International Search Report and a Written Opinion both dated Feb. 10, 2011, which issued during the prosecution of Applicant's PCT/IL10/00890.
Alfieri et al."Novel Suture Device for Beating-Heart Mitral Leaflet Approximation", Ann Thorac Surg. 2002, 74:1488-1493.
A Notice of Allowance dated Jun. 26, 2012, which issued during the prosecution of U.S. Appl. No. 12/608,316.
An International Search Report and a Written Opinion both dated Sep. 12, 2008, which issued during the prosecution of Applicant's PCT/IL07/01503.
An Office Action dated Jan. 23, 2012, which issued during the prosecution of U.S. Appl. No. 12/692,061.
An International Search Report dated May 19, 2011, which issued during the prosecution of Applicant's PCT/IL2011/00064.
A Supplemenatry European Search Report dated Feb. 1, 2011, which issued during the prosecution of European Patent Application No. EP 07849540.
An International Search Report together with Written Opinion both dated Mar. 30, 2011, which issued during the prosecution of Applicant's PCT/IL2010/001024.
An Office Action dated Aug. 6, 2012, which issued during the prosecution of U.S. Appl. No. 12/548,991.
An Office Action dated Jul. 20, 2012, which issued during the prosecution of U.S. Appl. No. 12/843,412.

(56) References Cited

OTHER PUBLICATIONS

Notice of Allowance dated Mar. 25, 2015, which issued during the prosecution of U.S. Appl. No. 13/749,153.
An Office Action dated Aug. 24, 2012, which issued during the prosecution of U.S. Appl. No. 12/563,930.
An Office dated May 10, 2012, which issued during the prosectuion of U.S. Appl. No. 12/795,026.
An Office Action dated Mar. 9, 2012, which issued during the prosecution of U.S. Appl. No. 12/689,635.
A Restriction Requirement dated Sep. 14, 2012, which issued during the prosecution of U.S. Appl. No. 12/795,192.
Notice of Allowance dated Dec. 24, 2014, which issued during the prosecution of U.S. Appl. No. 12/795,026.
An Office Action dated Sep. 28, 2011, which issued during the prosecution of U.S. Appl. No. 12/437,103.
An International Search Report and Written Opinion dated Nov. 8, 2010, which issued during the prosecution of Applicant's PCT/IL2010/000358.
An Office Action dated Dec. 29, 2011, which issued during the prosecution of U.S. Appl. No. 12/563,952.
An International Search Report and a Written Opinion both dated Nov. 23, 2011, which issued during the prosecution of Applicant's PCT/IL2011/000446.
An International Search Report with Written Opinion both dated Feb. 2, 2012, which issued during the prosecution of Applicant's PCT/IL2011/000600.
An International Preliminary Report on Patentability dated Nov. 9, 2011 which issued during the prosecution of Applicant's PCT/IL2010/000358.
An Office Action dated Aug. 4, 2010, which issued during the prosecution of U.S. Appl. No. 12/341,960.
An Office Action dated Nov. 14, 2011, which issued during the prosecution of U.S. Appl. No. 12/608,316.
An Office Action dated Aug. 15, 2013, which issued during the prosecution of U.S. Appl. No. 12/795,192.
An Office Action dated Jan. 17, 2013, which issued during the prosecution of U.S. Appl. No. 12/795,192.
An Office Action dated Feb. 12, 2013, which issued during the prosecution of U.S. Appl. No. 12/926,673.
Notice of Allowance dated Dec. 7, 2011, which issued during the prosecution of U.S. Appl. No. 12/435,291.
A Restriction Requirement dated Oct. 27, 2011, which issued during the prosecution of U.S. Appl. No. 12/563,952.
A Notice of Allowance dated May 24, 2012, which issued during the prosecution of U.S. Appl. No. 12/563,952.
A Restriction Requirement dated Jul. 5, 2012, which issued during the prosecution of U.S. Appl. No. 12/563,930.
A Notice of Allowance dated Apr. 3, 2013, which issued during the prosecution of U.S. Appl. No. 12/563,930.
An Office Action dated Apr. 2, 2013, which issued during the prosecution of U.S. Appl. No. 12/785,717.
An Advisory Acion dated Sep. 6, 2012 which issued during the prosecution of U.S. Appl. No. 12/548,991.
A Restriction Requirement dated Feb. 4, 2013 which issued during the prosectuion of U.S. Appl. No. 13/141,606.
An Office Action dated Feb. 14, 2013 which issued during the prosecution of U.S. Appl. No. 13/167,492.
An International Search Report and a Written Opinion both dated Feb. 22, 2013, which issued during the prosecution of Applicant's PCT/IL201/050451.
An Office Action dated Apr. 1, 2013 which issued during the prosecution of U.S. Appl. No. 13/167,476.
A Restriction Requirement dated Jun. 7, 2013 which issued during the prosecution of U.S. Appl. No. 13/141,606.
An Office Action dated Aug. 23, 2013 which issued during the prosecution of U.S. Appl. No. 13/167,444.
U.S. Appl. No. 61/265,936, filed Dec. 2, 2009.
U.S. Appl. No. 61/283,445, filed Dec. 2, 2009.
U.S. Appl. No. 61/207,908, filed Feb. 17, 2009.
Amplatzer Cardiac Plug brochure (English pages), AGA Medical Corporation (Plymouth, MN) (copyright 2008-2010, downloaded Jan. 11, 2011).
An Office Action dated Dec. 16, 2013, which issued during the prosecution of U.S. Appl. No. 13/666,262.
Notice of Allowance dated Nov. 19, 2013, which issued during the U.S. prosecution of U.S. Appl. No. 12/795,192.
An Office Action dated Oct. 2, 2013, which issued during the prosecution of U.S. Appl. No. 13/167,492.
An Office Action dated Nov. 21, 2013, which issued during the prosecution of U.S. Appl. No. 13/167,476.
An Office Action dated Dec. 18, 2013, which issued during the prosecution of U.S. Appl. No. 13/666,141.
A Restriction Requirement dated Apr. 19, 2010 which issued during the prosecution of U.S. Appl. No. 12/341,960.
An Office Action dated Jun. 13, 2012, which issued during the prosecution of U.S. Appl. No. 12/437,103.
An Office Action dated Nov. 30, 2012, which issued during the prosecution of U.S. Appl. No. 12/689,635.
An Office Action dated Oct. 22, 2013, which issued during the prosecution of U.S. Appl. No. 12/926,673.
A Restriction Requirement dated Oct. 25, 2012 which issued during the prosecution of U.S. Appl. No. 13/167,444.
An Office Action dated Jan. 17, 2013, which issued during the prosecution of U.S. Appl. No. 13/167,444.
A Restriction Requirement dated Nov. 2, 2012, which issued during the prosecution of U.S. Appl. No. 13/167,492.
An International Preliminary Report on Patentability dated Feb. 4, 2014, which issued during the prosecution of Applicant's PCT/IL2011/000446.
A Supplementary European Search Report dated Dec. 4, 2012, which issued during the prosecution of European Patent Application No. EP 09834225.6.
A Supplementary European Search Report dated Mar. 28, 2013, which issued during the prosecution of European Patent Application No. EP 1077 2091.4.
U.S. Appl. No. 61/733,979, filed Dec. 6, 2012.
U.S. Appl. No. 61/717,303, filed Oct. 23, 2012.
U.S. Appl. No. 61/820,979, filed May 8, 2013.
U.S. Appl. No. 61/745,848, filed Dec. 6, 2012.
An Office Action dated May 19, 2011, which issued during the prosecution of U.S. Appl. No. 12/706,868.
An Office Action dated Sep. 1, 2011, which issued during the prosecution of U.S. Appl. No. 12/706,868.
An Office Action dated Dec. 27, 2013, which issued during the prosecution of U.S. Appl. No. 12/785,717.
An Office Action dated May 30, 2012, which issued during the prosecution of U.S. Appl. No. 12/706,868.
An Office Action dated Apr. 7, 2015, which issued during the prosecution of U.S. Appl. No. 13/319,007.
An International Preliminary Report of Patentability dated Jan. 29, 2013, which issued during the prosecution of Applicant's PCT/IL2011/000600.
An International Search Report and a Written Opinion both dated Dec. 6, 2012 which issued during the prosecution of Applicant's PCT/IL2012/000250.
Notice of Allowance dated Nov. 13, 2014, which issued during the prosecution of U.S. Appl. No. 12/795,026.
U.S. Appl. No. 61/557,082, filed Nov. 8, 2011.
A Restriction Requirement dated Jul. 12, 2011, which issued during the prosecution of U.S. Appl. No. 12/437,103.
An Office Action dated Mar. 27, 2013, which issued during the prosecution of U.S. Appl. No. 12/843,412.
An Office Action dated May 6, 2013, which issued during the prosecution of U.S. Appl. No. 12/689,693.
A Restriction Requirement dated May 1, 2012, which issued during the prosecution of U.S. Appl. No. 12/843,412.
Langer et al. Ring plus String: Papillary muscle repositioning as an adjunctive repair technique for ischemic mitral regurgitation, The Journal of Thoracic Cardiovascular surgery vol. 133 No. 1, Jan. 2007.

(56) References Cited

OTHER PUBLICATIONS

Langer et al. Ring+String, Successful Repair technique for ischemic mitral regurgitation with severe leaflet Tethering, The Department of Thoracic Cardiovascular surgery, Hamburg, Germany, Nov. 2008.
U.S. Appl. No. 61/555,570, filed Nov. 4, 2011.
A Notice of Allowance dated Sep. 18, 2012, which issued during the prosecution of U.S. Appl. No. 12/706,868.
An Office Action dated Aug. 13, 2012, which issued during the prosecution of U.S. Appl. No. 13/044,694.
An Office Action dated Dec. 31, 2012, which issued during the prosecution of U.S. Appl. No. 13/044,694.
A Restriction Requirement dated Apr. 1, 2011, which issued during the prosecution of U.S. Appl. No. 12/608,316.
Agarwal et al. International Cardiology Perspective Functional Tricuspid Regurgitation, Circ Cardiovasc Interv 2009;2;2;565-573 (2009).
An Office Action dated Oct. 6, 2010, which issued during the prosecution of Applicant's U.S. Appl. No. 12/484,512.
An Office Action dated Jul. 6, 2012, which issued during the prosecution of U.S. Appl. No. 12/692,061.
An Interview Summary dated Jul. 27, 2011, which issued during the prosecution of U.S. Appl. No. 12/341,960.
A Notice of Allowance dated May 2, 2013, which issued during the prosecution of U.S. Appl. No. 12/843,412.
An Office Action dated Jul. 18, 2013, which issued during the prosecution of U.S. Appl. No. 13/044,694.
Search Report in European Patent Application 10772090.6 dated Jan. 17, 2014.
An Office Action dated Feb. 3, 2014, which issued during the prosecution of U.S. Appl. No. 12/689,693.
Communication regarding amended claims filed dated Dec. 27, 2012, regarding Euopean App No. 11792047.0.
Notice of Allowance dated Mar. 6, 2014, which issued during the prosecution of U.S. Appl. No. 12/437,103.
An Office Action dated Oct. 9, 2013, which issued during the prosecution of U.S. Appl. No. 12/996,954.
AMPLATZER® Septal Occluder. A patient guide to the Non-Surgical Closuer of the Atrial Septal Defect Using the AMPLATZER Septal Occluder System, AGA Medical Corporation, Apr. 2008.
Notice of Allowance dated Sep. 12, 2014, which issued during the prosecution of U.S. Appl. No. 11/950,930.
An Office Action dated Dec. 19, 2013, which issued during the prosecution of U.S. Appl. No. 14/027,934.
An International Preliminary Report on Patentability dated Dec. 18, 2010, which issued during the prosecution of Applicant's PCT/IL09/00593.
An English translation of an Office Action dated Apr. 23, 2014 which issued during the prosecution of Chinese Patent Application No. 201080059948.4.
Notice of Allowance dated Jun. 23, 2014, which issued during the prosecution of U.S. Appl. No. 12/548,991.
Notice of Allowance dated Jun. 11, 2014, which issued during the prosecution of U.S. Appl. No. 12/689,693.
Notice of Allowance dated Jun. 25, 2014, which issued during the prosecution of U.S. Appl. No. 13/666,262.
An International Search Report and Written Opinion both dated Apr. 9, 2014, which issued during the prosecution of Applicant's PCT/IL13/50860.
Notice of Allowance dated Nov. 7, 2014, which issued during the prosecution of U.S. Appl. No. 13/167,492.
An Office Action dated Jun. 11, 2014, which issued during the prosecution of U.S. Appl. No. 14/027,934.
A Restriction Requirement dated Jun. 2, 2014, which issued during the prosecution of U.S. Appl. No. 13/319,030.
Brennan, Jennifer, 510(k) Summary of safety and effectiveness, Jan. 2008.
A communication from the European Patent Office dated Sep. 28, 2011 which issued during the prosecution of European Application No. 09834225.6.
A Restriction Requirement dated Sep. 17, 2012, which issued during the prosecution of U.S. Appl. No. 12/689,693.
An Office Action dated Aug. 22, 2014, which issued during the prosecution of U.S. Appl. No. 14/027,934.
An Office Action dated Aug. 26, 2014 which issued during the prosecution of U.S. Appl. No. 13/167,444.
Communication dated Jul. 25, 2014, issued by the State Intellectual Property Office of the P.R. of China in counterpart Application No. 200980157331.3.
An Office Action dated Oct. 14, 2014, which issued during the prosecution of U.S. Appl. No. 13/319,030.
Supplementary European Search Report dated Oct. 23, 2014 which issued during the prosecution of Applicant's European App No. 10826224.7.
An International Search Report & Written Opinion both dated Mar. 21, 2014, which issued during the prosecution of Applicant's PCT/IL13/50992.
An Office Action dated Sep. 29, 2014, which issued during the prosecution of U.S. Appl. No. 13/504,870.
An Office Action dated Oct. 3, 2014, which issued during the prosecution of U.S. Appl. No. 13/749,153.
An International Search Report & Written Opinion both dated Sep. 8, 2009, which issued during the prosecution of Applicant's PCT/IL09/00593.
An International Preliminary Report on Patentability dated Jun. 10, 2009, which issued during the prosecution of Applicant's PCT/IL07/01503.
Notice of Allowance dated Jan. 22, 2015, which issued during the prosecution of U.S. Appl. No. 13/167,444.
Notice of Allowance dated Dec. 9, 2014, which issued during the prosecution of U.S. Appl. No. 13/167,476.
An English translation of an Office Action dated Dec. 12, 2013 which issued during the prosecution of Chinese Patent Application No. 200980157331.3.
An International Search Report and a Written Opinion both dated Nov. 14, 2011, which issued during the prosecution of Applicant's PCT/IL2011/000404.
Dictionary.com definition of "lock", Jul. 29, 2013.
A Restriction Requirement dated Jan. 6, 2012, which issued during the prosecution of U.S. Appl. No. 12/795,026.
A Restriction Requirement dated Nov. 14, 2011 which issued during the prosecution of U.S. Appl. No. 12/548,991.
An Office Action dated Jan. 13, 2015, which issued during the prosecution of U.S. Appl. No. 13/707,013.
A Notice of Allowance dated May 22, 2013, which issued during the prosecution of U.S. Appl. No. 12/689,635.
An International Preliminary Report on Patentability dated May 1, 2012, which issued during the prosecution of Applicant's PCT/IL2010/000890.
A Notice of Allowance dated Jan. 7, 2014, which issued during the prosecution of U.S. Appl. No. 12/926,673.
Restriction Requirement dated May 5, 2011, which issued during the prosecution of U.S. Appl. No. 12/706,868.
Supplementary European Search Report dated Aug. 4, 2014 which issued during the prosecution of Applicant's European App No. 11 81 1934.6.
An Office Action dated Aug. 5, 2010 which issued during the prosecution of U.S. Appl. No. 11/950,930.
An Office Action dated Feb. 17, 2010 which issued during the prosecution of U.S. Appl. No. 11/950,930.
Restriction Requirement dated Nov. 14, 2011, which issued during the prosecution of U.S. Appl. No. 12/689,635.
Supplementary European Search Report dated Jan. 21, 2014 which issued during the prosecution of Applicant's European App No. 11 78 6226.
An Office Action dated Jun. 4, 2014, which issued during the prosecution of U.S. Appl. No. 12/840,463.
Maisano, The double-orifice technique as a standardized approach to treat mitral . . . , European Journal of Cardio-thoracic Surgery 17 (2000) 201-205.
AMPLATZER® Cribriform Occluder. A patient guide to Percutaneous, Transcatheter, Atrial Septal Defect Closuer, AGA Medical Corporation, Apr. 2008.

(56) References Cited

OTHER PUBLICATIONS

An Office Action dated Jun. 10, 2014, which issued during the prosecution of U.S. Appl. No. 13/167,492.
Supplementary European Search Report dated Sep. 25, 2015, which issued during the prosecution of Applicant's European App No. 09794095.1.
An Office Action dated Apr. 2, 2015, which issued during the prosecution of U.S. Appl. No. 14/027,934.
An Office Action dated Mar. 23, 2015, which issued during the prosecution of U.S. Appl. No. 13/707,013.
Supplementary European Search Report dated Dec. 23, 2014 which issued during the prosecution of Applicant's European App No. 10834311.
An Office Action dated Mar. 24, 2015, which issued during the prosecution of U.S. Appl. No. 12/996,954.
Notice of Allowance dated Dec. 20, 2013, which issued during the prosecution of U.S. Appl. No. 12/437,103.
An International Preliminary Report on Patentability dated Dec. 23, 2014, which issued during the prosecution of Applicant's PCT/IL2012/050451.
An International Preliminary Report on Patentability dated Dec. 23, 2013, which issued during the prosecution of Applicant's PCT/IL2012/000250.
An Office Action dated Oct. 5, 2015, which issued during the prosecution of U.S. Appl. No. 14/246,417.
An Office Action dated Aug. 7, 2015, which issued during the prosecution of U.S. Appl. No. 14/128,756.
An Invitation to pay additional fees dated Jan. 31, 2014, which issued during the prosecution of Applicant's PCT/IL2013/050861.
An Invitation to pay additional fees dated Jan. 31, 2014, which issued during the prosecution of Applicant's PCT/IL2013/050860.
An Office Action dated Sep. 19, 2014, which issued during the prosecution of U.S. Appl. No. 13/044,694.
A communication from the European Patent Office dated Oct. 19, 2012 which issued during the prosecution of European Application No. 11792047.0.
An Office Action dated Oct. 5, 2012, which issued during the prosecution of U.S. Appl. No. 12/996,954.
An Office Action dated Oct. 1, 2015, which issued during the prosecution of U.S. Appl. No. 14/141,228.
Notice of Allowance dated May 6, 2016, which issued during the prosecution of U.S. Appl. No. 14/667,090.
Notice of Allowance dated Apr. 12, 2016, which issued during the prosecution of U.S. Appl. No. 14/667,090.
Ammendment, Terminal Disclaimer and Extension dated Jun. 27, 2012, which issued during the prosecution of U.S. Appl. No. 12/548,991.
An Office Action dated Jun. 18, 2015, which issued during the prosecution of U.S. Appl. No. 14/551,951.
A Notice of Allowance dated Feb. 2, 2015, which issued during the prosecution of U.S. Appl. No. 13/504,870.
An Office Action dated Jan. 5, 2016, which issued during the prosecution of U.S. Appl. No. 14/027,934.
An Office Action dated Mar. 16, 2015, which issued during the prosecution of U.S. Appl. No. 14/084,426.
European Search Report dated Jun. 24, 2016, which issued during the prosecution of European Patent Application No. EP 12847363.
An Office Action dated Mar. 24, 2015, which issued during the prosecution of U.S. Appl. No. 14/486,226.
An Office Action dated Jul. 20, 2016, which issued during the prosecution of U.S. Appl. No. 14/246,417.
Notice of Allowance dated May 22, 2015, which issued during the prosecution of U.S. Appl. No. 13/749,153.
An Office Action dated Jun. 18, 2015, which issued during the prosecution of U.S. Appl. No. 13/319,030.
An Office Action dated Jun. 13, 2014, which issued during the prosecution of U.S. Appl. No. 13/141,606.
An English translation of an Office Action dated Jul. 17, 2015 which issued during the prosecution of Chinese Patent Application No. 201080059948.4.
Notice of Allowance dated Sep. 29, 2014, which issued during the prosecution of U.S. Appl. No. 13/141,606.
An International Search Report and a Written Opinion both dated Oct. 27, 2016, which issued during the prosecution of Applicant's PCT/IL2015/050792.
An International Preliminary Report on Patentability dated Jun. 9, 2015, which issued during the prosecution of Applicant's PCT/IL2013/050992.
An Office Action dated May 3, 2016, which issued during the prosecution of U.S. Appl. No. 13/319,030.
A Notice of Allowance dated Sep. 2, 2016, which issued during the prosecution of U.S. Appl. No. 14/027,934.
An Office Action dated Feb. 3, 2015, which issued during the prosecution of U.S. Appl. No. 14/084,426.
Search Report in European Patent Application 10826224.7 dated Nov. 16, 2015.
An International Preliminary Report on Patentability dated Apr. 28, 2015, which issued during the prosecution of Applicant's PCT/IL2013/050861.
An English Translation of an Office Action dated Nov. 24, 2015, which issued during the prosecution of Israel Patent Application No. 223448. (the relevant part only).
Notice of Allowance dated Nov. 12, 2015, which issued during the prosecution of U.S. Appl. No. 13/319,007.
Notice of Allowance dated Jan. 7, 2016, which issued during the prosecution of U.S. Appl. No. 13/319,007.
Notice of Allowance dated Apr. 20, 2011, which issued during the prosecution of U.S. Appl. No. 12/484,512.
Notice of Allowance dated Mar. 23, 2011, which issued during the prosecution of U.S. Appl. No. 12/484,512.
An Office Action dated May 23, 2016, which issued during the prosecution of U.S. Appl. No. 14/209,171.
European Search Report dated Jul. 8, 2016, which issued during the prosecution Applicant's European App No. 13849843.1.
Notice of Allowance dated Nov. 23, 2016, which issued during the prosecution of U.S. Appl. No. 14/141,228.
Supplementary European Search Report dated Mar. 23, 2015, which issued during the prosecution of Applicant's European App No. 11792047.0.
Supplementary European Search Report dated Apr. 29, 2015, which issued during the prosecution of Applicant's European App No. 14200202.
An International Search Report and a Written Opinion both dated Apr. 15, 2014, which issued during the prosecution of Applicant's PCT/IL2013/050861.
Notice of Allowance dated Nov. 17, 2015, which issued during the prosecution of U.S. Appl. No. 14/486,226.
European Search Report dated Nov. 4, 2015, which issued during the prosecution of European Patent Application No. EP 1077 2091.4.
Notice of Allowance dated Dec. 19, 2016, which issued during the prosecution of U.S. Appl. No. 14/242,151.
European Search Report dated Jul. 15, 2016, which issued during the prosecution of Applicant's European App No. 13849947.0.
An Office Action dated Jun. 17, 2016, which issued during the prosecution of U.S. Appl. No. 14/357,040.
Notice of Allowance dated Dec. 30, 2016, which issued during the prosecution of U.S. Appl. No. 13/319,030.
An Office Action dated Mar. 23, 2015, which issued during the prosecution of European Patent Application No. EP 09834225.6.
Notice of Allowance dated Aug. 3, 2015, which issued during the prosecution of U.S. Appl. No. 13/749,153.
A Notice of Allowance dated Sep. 16, 2016, which issued during the prosecution of U.S. Appl. No. 14/027,934.
A Notice of Allowance dated Jul. 30, 2105, which issued during the prosecution of U.S. Appl. No. 13/319,007.
A Notice of Allowance dated Sep. 3, 2014, which issued during the prosecution of U.S. Appl. No. 12/689,693.
An International Preliminary Report on Patentability dated Apr. 28, 2015, which issued during the prosecution of Applicant's PCT/IL2013/050860.
An Office Action dated Jan. 6, 2016, which issued during the prosecution of U.S. Appl. No. 14/128,756.

(56) References Cited

OTHER PUBLICATIONS

An Office Action dated Apr. 8, 2016, which issued during the prosecution of U.S. Appl. No. 14/141,228.
An Office Action dated Apr. 7, 2016, which issued during the prosecution of U.S. Appl. No. 14/242,151.
An Office Action dated Jan. 4, 2016, which issued during the prosecution of U.S. Appl. No. 14/589,100.
Communication from the European Patent Office dated Jun. 11, 2015, which issued during the prosecution of European Patent Application No. 11811934.
Notice of Allowance dated Aug. 19, 2013, which issued during the prosecution of U.S. Appl. No. 11/908,906.
An Office Action dated Jun. 8, 2012, which issued during the prosecution of U.S. Appl. No. 11/908,906.
An Office Action dated Dec. 21, 2013, which issued during the prosecution of U.S. Appl. No. 11/908,906.
A Restriction Requirement dated Aug. 5, 2011, which issued during the prosecution of U.S. Appl. No. 11/908,906.
An Office Action dated Oct. 23, 2012, which issued during the prosecution of Japanese Patent Application No. 2009-539871.
U.S. Appl. No. 60/662,616, filed Mar. 17, 2005.
U.S. Appl. No. 60/700,542, filed Jul. 18, 2005.
An Office Action dated May 4, 2016, which issued during the prosecution of U.S. Appl. No. 14/589,100.
An Office Action dated Jun. 14, 2016, which issued during the prosecution of U.S. Appl. No. 14/273,155.
An International Search Report and a Written Opinion both dated Jan. 25, 2016, which issued during the prosecution of Applicant's PCT/IL2015/051027.
An Office Action dated Jan. 5, 2016, which issued during the prosecution of U.S. Appl. No. 14/084,426.
An International Preliminary Report on Patentability dated Apr. 26, 2016, which issued during the prosecution of Applicant's PCT/IL2014/050914.
An Office Action dated May 11, 2016, which issued during the prosecution of U.S. Appl. No. 14/128,756.
An English Translation of an Office Action dated Sep. 15, 2016, which issued during the prosecution of Israel Patent Application No. 243837. (the relevant part only).
Notice of Allowance dated Sep. 14, 2015, which issued during the prosecution of U.S. Appl. No. 13/707,013.
Notice of Allowance dated Jul. 24, 2015, which issued during the prosecution of U.S. Appl. No. 13/707,013.
Notice of Allowance dated Jul. 8, 2015, which issued during the prosecution of U.S. Appl. No. 13/707,013.
Ahmadi, Ali, et al. "Percutaneously adjustable pulmonary artery band." *The Annals of thoracic surgery* 60 (1995): S520-S522.
Assad, Renato S. "Adjustable Pulmonary Artery Banding." (2014).
Ahmadi, A., G. Spillner, and Th Johannesson. "Hemodynamic changes following experimental production and correction of acute mitral regurgitation with an adjustable ring prosthesis." *The Thoracic and cardiovascular surgeon*36.06 (1988): 313-319.
Swenson, Orvar. "Internal device for control of urinary incontinence." *Journal of pediatric surgery* 7.5 (1972): 542-545.
Park, Sang C., et al. "A percutaneously adjustable device for banding of the pulmonary trunk." *International journal of cardiology* 9.4 (1985): 477-484.
Elliott, Daniel S., Gerald W. Timm, and David M. Barrett. "An implantable mechanical urinary sphincter: a new nonhydraulic design concept." *Urology*52.6 (1998): 1151-1154.
An Invitation to pay additional fees dated Aug. 18, 2016, which issued during the prosecution of Applicant's PCT/IL2016/050433.
Daebritz, S., et al. "Experience with an adjustable pulmonary artery banding device in two cases: initial success-midterm failure." *The Thoracic and cardiovascular surgeon* 47.01 (1999): 51-52.
Notice of Allowance dated Mar. 1, 2017, which issued during the prosecution of U.S. Appl. No. 14/357,040.
An Office Action dated Sep. 6, 2016, which issued during the prosecution of U.S. Appl. No. 14/141,228.
An International Search Report and a Written Opinion both dated Oct. 17, 2016, which issued during the prosecution of Applicant's PCT/IL2016/050433.
An Office Action dated Oct. 21, 2016, which issued during the prosecution of U.S. Appl. No. 14/567,472.
Notice of Allowance dated Jul. 7, 2015, which issued during the prosecution of U.S. Appl. No. 12/996,954.
Notice of Allowance dated Nov. 18, 2016, which issued during the prosecution of U.S. Appl. No. 13/740,582.
Notice of Allowance dated Oct. 20, 2015, which issued during the prosecution of U.S. Appl. No. 12/996,954.
Amendment and Extension dated Apr. 11, 2012, which issued during the prosecution of U.S. Appl. No. 12/563,952.
Notice of Allowance dated Dec. 8, 2016, which issued during the prosecution of U.S. Appl. No. 14/246,417.
Notice of Allowance dated Dec. 21, 2016, which issued during the prosecution of U.S. Appl. No. 14/246,417.
Notice of Allowance dated Dec. 29, 2016, which issued during the prosecution of U.S. Appl. No. 14/246,417.
Notice of Allowance dated Jan. 3, 2017, which issued during the prosecution of U.S. Appl. No. 14/128,756.
Swenson, O. and Malinin, T.I., 1978. An improved mechanical device for control of urinary incontinence. *Investigative urology*, 15(5), pp. 389-391.
Swenson, O. An experimental implantable urinary sphincter. *Invest Urol*, Sep. 1976;14(2):100-3.
An International Preliminary Report on Patentability dated Sep. 18, 2007, which issued during the prosecution of Applicant's PCT/IL2006/000342.
An International Search Report and a Written Opinion both dated May 30, 2007, which issued during the prosecution of Applicant's PCT/IL2006/000342.
An Advisory Action dated Feb. 4, 2014, which issued during the prosecution of U.S. Appl. No. 13/167,476.
An English Translation of an Office Action dated May 31, 2012, which issued during the prosecution of Israel Patent Application No. 209946. (the relevant part only).
A Restriction Requirement dated Jul. 8, 2015, which issued during the prosecution of U.S. Appl. No. 14/141,228.
Notice of Allowance dated Sep. 22, 2016, which issued during the prosecution of U.S. Appl. No. 13/740,582.
A Restriction Requirement dated Sep. 4, 2015, which issued during the prosecution of U.S. Appl. No. 14/589,100.
Notice of Allowance dated Jan. 29, 2016, which issued during the prosecution of U.S. Appl. No. 14/551,951.
An International Search Report and a Written Opinion both dated May 28, 2014, which issued during the prosecution of Applicant's PCT/IL14/050027.
An Office Action dated Aug. 22, 2016, which issued during the prosecution of U.S. Appl. No. 14/084,426.
An Office Action dated Dec. 20, 2016, which issued during the prosecution of UK Patent Application No. 1611910.9.
Notice of Allowance dated Aug. 7, 2015, which issued during the prosecution of Chinese Patent Application No. 200980157331.3.
An Office Action dated Jan. 20, 2017, which issued during the prosecution of U.S. Appl. No. 14/650,114.
An Office Action dated Feb. 27, 2017, which issued during the prosecution of U.S. Appl. No. 15/249,957.
An Office Action dated Feb. 2, 2017, which issued during the prosecution of U.S. Appl. No. 14/209,171.
An Office Action dated Jan. 25, 2017, which issued during the prosecution of Chinese Patent Application No. 201510681407.X.
An Office Action dated Dec. 13, 2016, which issued during the prosecution of Applicant's European App No. 11786226.8.
An Interview Summary dated Apr. 4 ,2012, which issued during the prosecution of U.S. Appl. No. 12/563,952.
An Office Action dated Mar. 3, 2017, which issued during the prosecution of Applicant's European App No. 11792047.0.
An Office Action dated May 28, 2015, which issued during the prosecution of U.S. Appl. No. 14/128,756.
An International Search Report & Written Opinion both dated May 12, 2015, which issued during the prosecution of Applicant's PCT/IL2014/050914.

(56) References Cited

OTHER PUBLICATIONS

Alfieri et al., "The edge to edge technique," The European Association for Cardio-Thoracic Surgery 14$^{th}$ Annual Meeting Oct. 7-11, Book of Procees. (2000).
An Office Action dated Feb. 10, 2017, which issued during the prosecution of U.S. Appl. No. 14/990,172.
An Office Action dated Mar. 24, 2017, which issued during the prosecution of U.S. Appl. No. 14/273,155.
U.S. Appl. No. 61/894,486, filed Oct. 23, 2013.
An Office Action dated Apr. 6, 2017, which issued during the prosecution of U.S. Appl. No. 14/437,062.
Notice of Allowance dated Apr. 13, 2017, which issued during the prosecution of U.S. Appl. No. 14/650,114.

\* cited by examiner

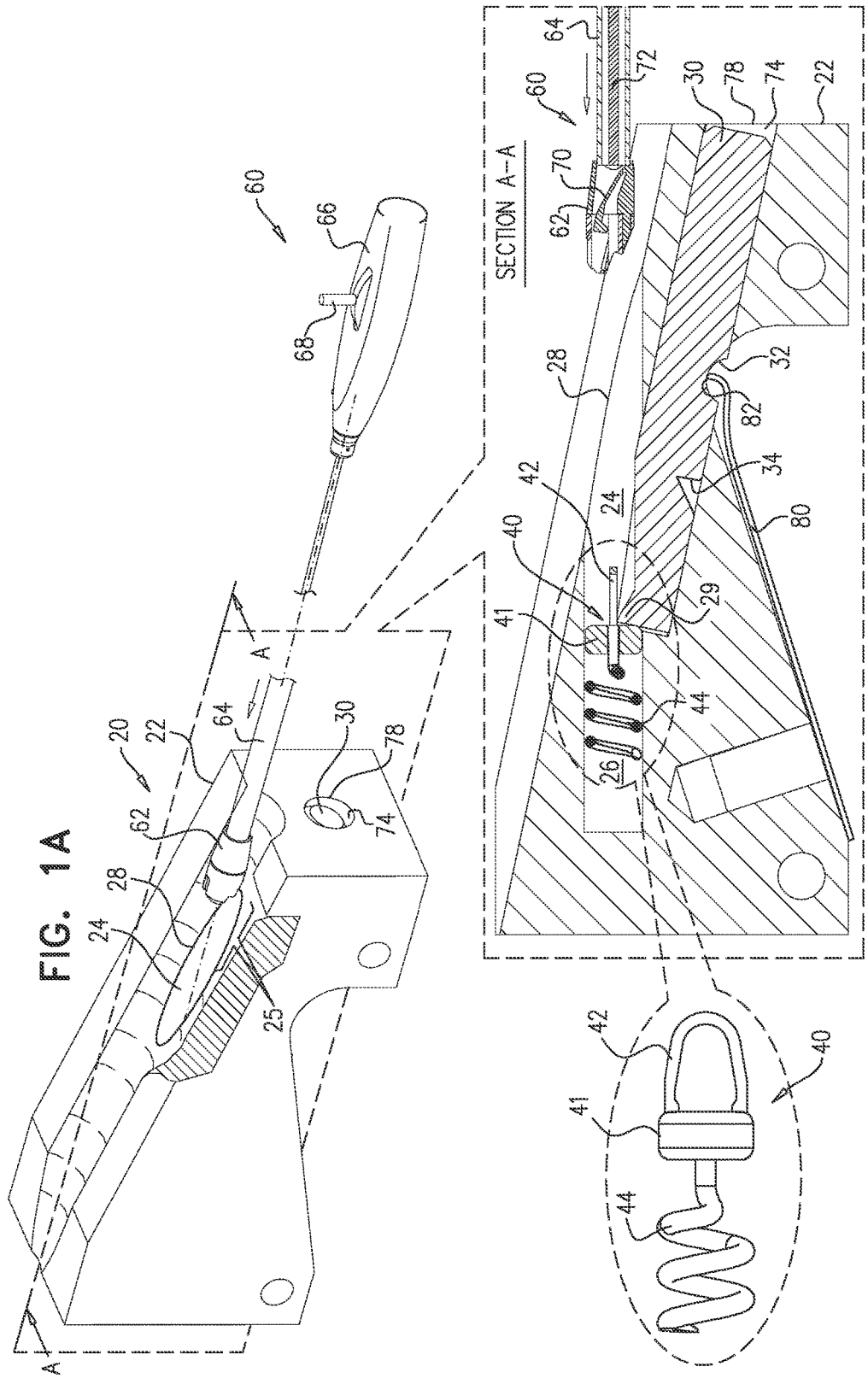

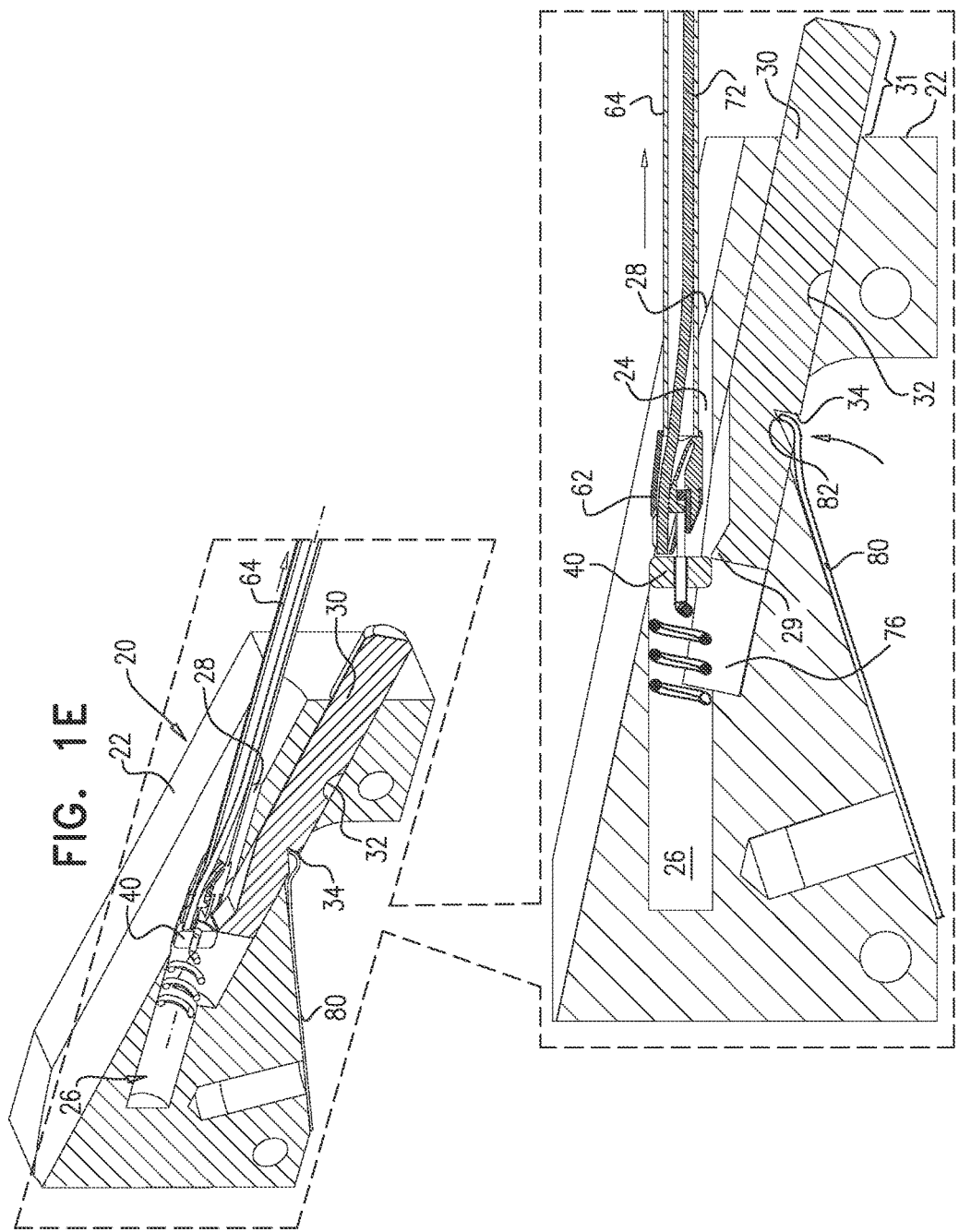

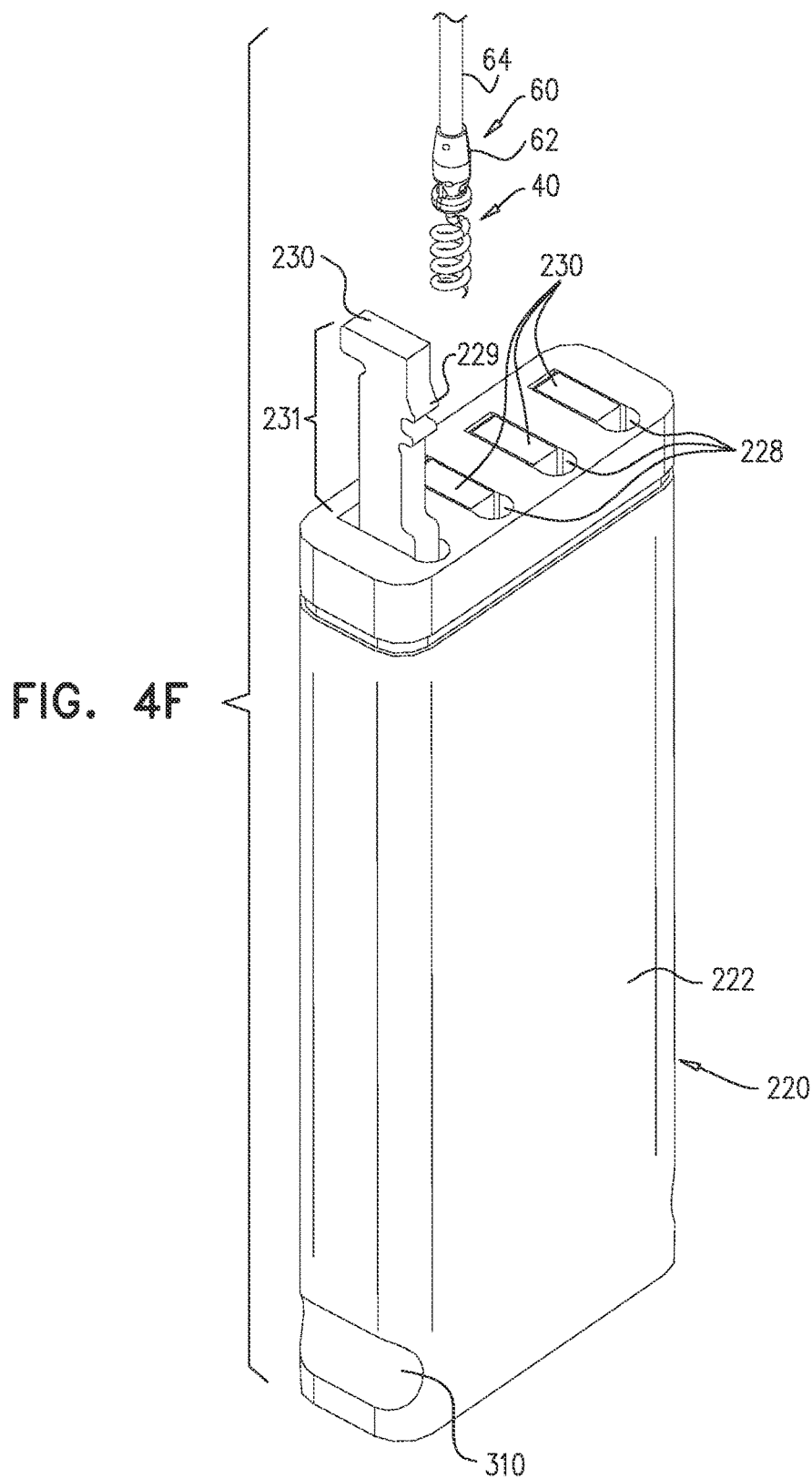

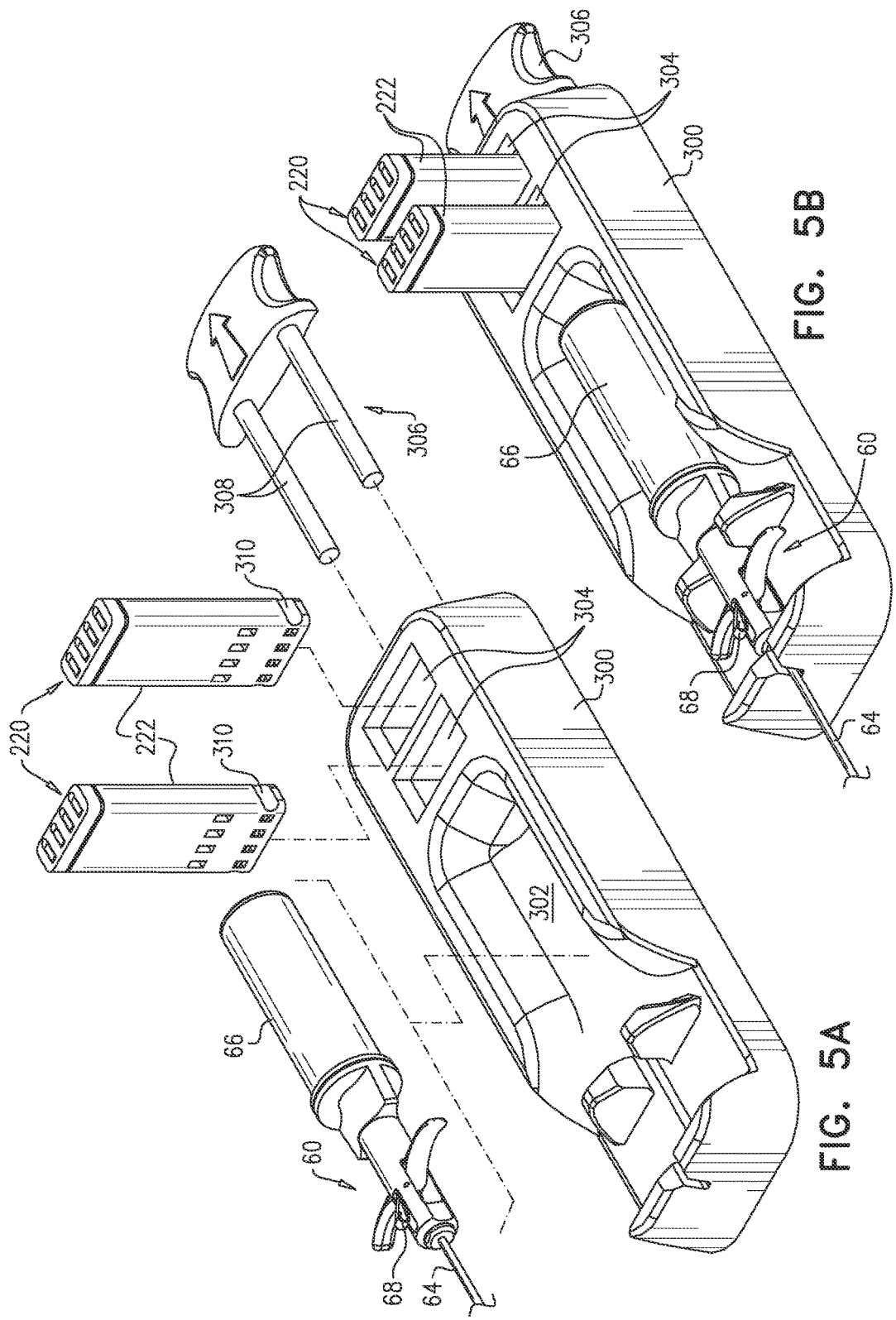

ANCHOR MAGAZINE

CROSS-REFERENCES TO RELATED APPLICATIONS

The present application is a US National Phase of PCT application IL2014/050914 to Zipory et al., which published as WO 2015/059699, and which claims priority from US Provisional Patent Application U.S. 61/894,486 to Zipory et al., entitled "Anchor Magazine", filed Oct. 23, 2013, which is incorporated herein by reference.

The present application is related to PCT Patent Application IL2013/050861 to Herman et al., entitled "Percutaneous tissue anchor techniques", filed on Oct. 23, 2013, which published as WO 2014/064695, and PCT Patent Application IL2013/050860 to Sheps et al., entitled "Controlled steering functionality for implant-delivery tool", filed on Oct. 23, 2013, which published as WO 2014/064694, both of which are incorporated herein by reference.

FIELD OF THE INVENTION

The present invention relates in general to handling of tissue anchors. More specifically, the present invention relates to devices and techniques for handling of a plurality of tissue anchors, and the use thereof at a heart valve of a patient.

BACKGROUND

Tissue anchors are placed intracorporeally so as to anchor implants to a tissue of a subject. Typically, this intracorporeal placement necessitates that the tissue anchors are small, e.g., having a greatest dimension (e.g., a length) of less than 11 mm and/or a maximum width of 3 mm. It is therefore typically advantageous to provide devices and techniques to facilitate handling of the tissue anchors.

SUMMARY OF THE INVENTION

An anchor-handling device is configured to facilitate handling of one or more tissue anchors. The anchor-handling device retains the anchors within an anchor-storage zone of a channel defined by a housing until a tool such as an anchor driver is used to retrieve the anchor. The tool is advanced through the channel, coupled to the anchor, and removed proximally out of the channel with the anchor. The anchor-handling device is configured to release (e.g., dispense) the anchor only when a proximally-directed force applied by the tool to the anchor is greater than a pre-defined threshold force (i.e., is sufficient), so as to prevent inadvertent exit of the anchor.

A retaining member is configured to retain the tissue anchor in the anchor-storage zone, typically by obstructing exit of the tissue anchor. The sufficient proximally-directed force moves the retaining member out of the way of the anchor, e.g., by moving the anchor to push the retaining member out of the way. Typically, an inhibitor inhibits movement of the retaining member, thereby configuring the retaining member to move out of the way of the anchor only in response to the sufficient proximally-directed force.

For some applications, the anchor-handling device is used in combination with a multi-component tubular system for transcatheter delivery of an implant, e.g., to facilitate sequential delivery of a plurality of anchors to the implant via the system.

There is therefore provided, in accordance with an application of the present invention, apparatus for use with an anchor driver, the apparatus including:
a housing, shaped to define a channel having an anchor-storage zone and a proximal opening configured to provide access for the anchor driver to the anchor-storage zone;
a tissue anchor, stored in the anchor-storage zone and slidable through the channel; and
a retaining member:
having a retaining state in which the retaining member is configured to retain the tissue anchor in the anchor-storage zone, and
being configured, by moving in response to a proximally-directed force applied to the tissue anchor, to allow the tissue anchor to leave the anchor-storage zone in response to the proximally-directed force, the proximally-directed force being greater than a pre-determined threshold force.

In an application, the apparatus is configured such that after removal of the tissue anchor from the housing, a distally-directed force required to return the apparatus to the retaining state is more than twice as great as the threshold force.

In an application, the retaining member is configured such that the threshold force is 300-1500 grams force.

In an application, the tissue anchor has a mass, and the retaining member is configured such that the threshold force, measured in grams force, is 1000-150,000 times greater than the mass of the tissue anchor, measured in grams.

In an application, the apparatus further includes an inhibitor, configured to configure the retaining member to (i) retain the tissue anchor in the anchor-storage zone, and (ii) to allow the tissue anchor to leave the anchor-storage zone in response to the proximally-directed force.

In an application, the tissue anchor is dimensioned to fit snugly in the anchor-storage zone.

In an application, the apparatus further includes a multi-component tubular system for transcatheter implantation of an implant into a subject, the implant configured to be anchored to tissue of the subject using the tissue anchor, and the housing being coupled to a component of the multi-component tubular system.

In an application, the component of the multi-component tubular system includes a stand, and the housing is coupled to the stand.

In an application, the multi-component tubular system defines a proximal port through which the anchor is introducible, and the housing is coupled to the component of the multi-component tubular system such that the proximal opening of the housing is disposed between 1 and 40 cm from the port of the multi-component tubular system.

In an application, the multi-component tubular system defines a proximal port through which the anchor is introducible, and the housing is coupled to the component of the multi-component tubular system such that the proximal opening of the housing faces generally the same direction as the port of the multi-component tubular system.

In an application:
the housing is configured to define a plurality of channels, each of the plurality of channels having a respective anchor-storage zone and a respective proximal opening, and
the apparatus includes a plurality of tissue anchors, slidable through a respective channel and configured to be stored in a respective anchor-storage zone.

In an application, the apparatus includes a plurality of retaining members, each retaining member configured to retain a respective tissue anchor in the respective anchor-storage zone, and to allow the respective tissue anchor to leave the respective anchor-storage zone in response to a proximally-directed force applied to the respective tissue anchor.

In an application, in the retaining state, at least a portion of the retaining member obstructs proximal movement of the tissue anchor by being disposed within the channel.

In an application, the apparatus further includes the anchor driver, and in the retaining state, the anchor driver is slidable through the channel and lockable to the tissue anchor while at least the portion of the retaining member obstructs proximal movement of the tissue anchor by being disposed within the channel.

In an application, in the retaining state, the anchor driver is slidable through the channel such that a part of the anchor driver becomes positioned between a part of the tissue anchor and a part of the retaining member, and the anchor driver is lockable to the tissue anchor only while the part of the anchor driver is positioned between the part of the tissue anchor and the part of the retaining member.

In an application:
the tissue anchor includes a core, a tissue-engaging member coupled to a distal side of the core, and a coupling head coupled to a proximal side of the core, and
in the retaining state, at least the portion of the retaining member that obstructs the proximal movement of the tissue anchor obstructs the proximal movement of the tissue anchor by engaging the core.

In an application:
the housing is shaped to define a chamber that is in fluid communication with the channel,
at least part of the retaining member is configured to slide within the chamber in response to the proximally-directed force applied to the tissue anchor.

In an application, a first end of the chamber is in fluid communication with the channel, the housing defines a chamber opening of the chamber at a second end of the chamber, the portion of the retaining member includes a first portion of the retaining member, and the retaining member is configured such that, in response to the proximally-directed force applied to the tissue anchor, a second portion of the retaining member moves out of the chamber opening.

In an application, the retaining member is configured such that, in response to the proximally-directed force applied to the tissue anchor, a second portion of the retaining member moves out of the housing.

In an application, the apparatus is configured such that after removal of the tissue anchor from the housing, a distally-directed force required to return the apparatus to the retaining state is more than twice as great as the threshold force.

In an application, the retaining member includes a pin, configured to slide through the chamber.

In an application:
the housing is shaped to define a cavity that is in fluid communication with the chamber,
at least a portion of the retaining member is resilient,
the retaining member is shaped to define a detent,
in the retaining state, the resilience of at least the portion of the retaining member holds the detent within the cavity, and
the retaining member is configured to deform in response to the proximally-directed force applied to the tissue anchor, such that the detent exits the cavity.

In an application:
the cavity includes a first cavity,
the housing is shaped to define a second cavity that is in fluid communication with the chamber, and
the apparatus is dimensioned such that when the retaining member allows the tissue anchor to leave the anchor-storage zone, further proximal movement of the retaining member causes the detent to move into the second cavity.

In an application, the second cavity is larger in at least one dimension than the first cavity.

In an application, the second cavity is differently shaped to the first cavity.

In an application, the second cavity and the detent are dimensioned such that when the detent is disposed within the second cavity, a distally-directed force required to return the apparatus to the retaining state is more than twice as great as the threshold force.

In an application, at least a portion of the pin is dimensioned to slide snugly through the chamber.

In an application, the apparatus further includes an inhibitor tongue having a pin-contacting portion that is in contact with the pin, and configured to (i) inhibit the pin from sliding through the chamber in response to a sub-threshold force, and (ii) to allow the pin to slide through the chamber in response to the proximally-directed force applied to the tissue anchor.

In an application:
the pin is shaped to define a cavity,
at least a portion of the inhibitor tongue is resilient,
in the retaining state, the resilience of at least the portion of the inhibitor tongue holds the pin-contacting portion within the cavity, and
the inhibitor tongue is configured to deform in response to the proximally-directed force applied to the tissue anchor, such that the pin-contacting portion exits the cavity.

In an application:
the cavity includes a first cavity.
the pin is shaped to define a second cavity,
the apparatus is dimensioned such that when the retaining member allows the tissue anchor to leave the anchor-storage zone, further proximal movement of the retaining member causes the pin-contacting portion to move into the second cavity.

In an application, the second cavity is larger in at least one dimension than the first cavity.

In an application, the second cavity is differently shaped to the first cavity.

In an application, the second cavity and the pin-contacting portion are dimensioned such that when the pin-contacting portion is disposed within the second cavity, a distally-directed force required to return the apparatus to the retaining state is more than twice as great as the threshold force.

In an application, the chamber is in fluid communication with the channel at a distal end of the chamber, and has a proximal-distal longitudinal axis that is disposed at between 5 and 30 degrees from a proximal-distal longitudinal axis of the channel.

In an application, the proximal-distal longitudinal axis of the chamber is disposed at between 5 and 20 degrees from the proximal-distal longitudinal axis of the channel In an application, the proximal-distal longitudinal axis of the chamber is disposed at between 11 and 14 degrees from the proximal-distal longitudinal axis of the channel.

In an application, a central longitudinal axis of the chamber is parallel with a central longitudinal axis of the channel.

In an application, the tissue anchor is dimensioned to fit snugly through the channel.

In an application, the tissue anchor includes a core, a tissue-engaging member coupled to a distal side of the core, and a coupling head, the core is dimensioned to fit snugly through the channel, and the tissue-engaging member is dimensioned so as to not touch the housing when the tissue anchor moves through the channel.

In an application, the apparatus further includes the anchor driver.

In an application, the anchor driver includes:
 at a distal end thereof, an anchor-engaging head introducible through the opening of the housing and actuatable to be reversibly coupled to the tissue anchor;
 at a proximal end thereof, a handle including an adjuster configured to actuate the anchor-engaging head; and
 a flexible shaft:
  disposed between the distal end of the anchor driver and the proximal end of the anchor driver,
  having a length of 50-250 cm, and
  configured to be transcatheterally advanced through vasculature of a subject.

In an application, the opening of the housing is rotationally asymmetrical, a transverse cross-section of the anchor-engaging head is rotationally asymmetrical, and the opening limits a range of rotational orientations of the anchor-engaging head with respect to the opening in which the anchor-engaging head is introducible through the opening.

In an application, the opening of the housing and the transverse cross-section of the anchor-engaging head each have the shape of an ellipse that has had a segment removed.

In an application, the tissue anchor is stored in the anchor-storage zone in a given rotational orientation of the tissue anchor with respect to the opening, the anchor-engaging head is couplable to the tissue anchor in not all rotational orientations of the head with respect to the tissue anchor, and the anchor-engaging head is couplable to the tissue anchor without rotating the anchor-engaging head subsequently to introducing the anchor-engaging head through the opening.

In an application, the opening limits the range of rotational orientations such that the anchor-engaging head is introducible through the opening in only a given rotational orientation of the head with respect to the opening.

In an application, the apparatus further includes a base, and:
 the housing is couplable to the base,
 the base is configured to at least partly immobilize the housing, and
 the base is shaped to define a receptacle for housing and at least partly immobilizing the handle.

In an application, when the housing is coupled to the base, the housing is disposed less than 30 cm from the receptacle.

In an application:
 the receptacle is a handle receptacle,
 the housing is reversibly couplable to the base,
 the base is shaped to further define a housing receptacle, configured to house the housing,
 the base further includes a locking element, movable between a locked state that locks the housing within the receptacle, and an unlocked state that facilitates release of the housing from the receptacle.

In an application, the adjuster is operable while the receptacle houses the handle.

In an application, the apparatus is configured such that while the receptacle houses the handle, a human operator may:
 with a first hand of the operator, grasp a distal portion of the driver and introduce the head into the opening, and
 with a second hand of the operator, reversibly actuate the head by operating the adjuster while grasping the distal portion of the driver with the first hand.

There is further provided, in accordance with an application of the present invention, apparatus for use with an anchor driver, the apparatus including:
 a housing, shaped to define a channel having (a) an anchor-storage zone and (b) a proximal opening configured to provide access for the anchor driver to the anchor-storage zone;
 a tissue anchor, slidable through the channel and configured to be stored in the anchor-storage zone; and
 a retaining member:
  having a retaining state in which the retaining member is configured to retain the tissue anchor in the anchor-storage zone, and
  being disposed within the housing such that sliding of the tissue anchor proximally out of the anchor-storage zone and through the channel causes the retaining member to slide in an at least partly proximal direction.

In an application, the retaining member is disposed within the housing such that sliding of the tissue anchor proximally out of the anchor-storage zone and through the channel causes the retaining member to slide along an axis that is disposed at an angle of less than 30 degrees with respect to a central longitudinal axis of the channel.

There is further provided, in accordance with an application of the present invention, apparatus, including:
 a housing, shaped to define a channel having an anchor-storage zone and a proximal opening;
 an anchor driver including an anchor-engaging head, a handle, and a shaft therebetween, and:
  the shaft is flexible and is configured to be transluminally advanced into a subject, and
  the anchor-engaging head is dimensioned to be advanceable through the proximal opening toward the anchor-storage zone; and
 a tissue anchor:
  stored in the anchor-storage zone,
  including (i) a coupling head configured to be locked to the anchor-engaging head while the tissue anchor is in the anchor-storage zone, and (ii) a tissue-engaging member configured to be driven into tissue of the subject using the anchor driver, and
  configured such that, while stored in the anchor-storage zone, the tissue anchor is movable out of the anchor-storage zone toward the proximal opening only in response to a proximally-directed force being applied to the tissue anchor, the proximally-directed force being greater than a pre-determined threshold force.

In an application, the tissue anchor is configured to be movable out of the anchor-storage zone only in response to the proximally-directed force, by being dimensioned with respect to at least one dimension of the housing such that the tissue anchor is movable out of the anchor-storage zone only in response to the proximally-directed force.

There is further provided, in accordance with an application of the present invention, apparatus, including:
 an anchor-handling device including a housing, shaped to define a channel having an anchor-storage zone and a proximal opening;
 an anchor driver including an anchor-engaging head, a handle, and a shaft therebetween, and:
  the shaft is flexible and is configured to be transluminally advanced into a subject, and the anchor-engaging head is dimensioned to be advanceable through the proximal opening toward the anchor-storage zone; and a tissue anchor:
stored in the anchor-storage zone,
including (i) a coupling head configured to be locked to the anchor-engaging head while the tissue anchor is in the anchor-storage zone, and (ii) a tissue-engaging member configured to be driven into tissue of the subject using the anchor driver, and
configured such that, while stored in the anchor-storage zone, the tissue anchor is movable out of the anchor-storage zone toward the proximal opening in response to a proximally-directed force being applied to the tissue anchor by the anchor driver,
and the anchor-handling device is configured to provide an indication of the movement of the tissue anchor out of the anchor-storage zone toward the proximal opening in response to the proximally-directed force.

In an application, the anchor-handling device is configured to provide the indication by the housing being at least in part transparent, such that the movement of the tissue anchor is viewable from outside the housing.

In an application, the anchor-handling device is configured to provide the indication by including an element that moves with respect to the housing in response to the movement of the tissue anchor.

In an application, the element that moves with respect to the housing moves out of the housing in response to the movement of the tissue anchor.

In an application, the element that moves with respect to the housing moves with respect to the housing at a rate that is relative to a rate at which the anchor moves with respect to the housing.

The present invention will be more fully understood from the following detailed description of applications thereof, taken together with the drawings, in which:

BRIEF DESCRIPTION OF THE DRAWINGS

FIGS. 1A-F are schematic illustrations of an anchor-handling device, configured to facilitate handling of at least one tissue anchor, in accordance with some applications of the invention;

FIGS. 4A-F are schematic illustrations of an anchor-handling device, configured to facilitate handling of at least one tissue anchor, in accordance with some applications of the invention; and FIGS. 5A-C are schematic illustrations of a base to which an anchor-handling device is couplable, and which is configured to at least partly immobilize the anchor-handling device, in accordance with some applications of the invention.

DETAILED DESCRIPTION OF EMBODIMENTS

Figure 1B:
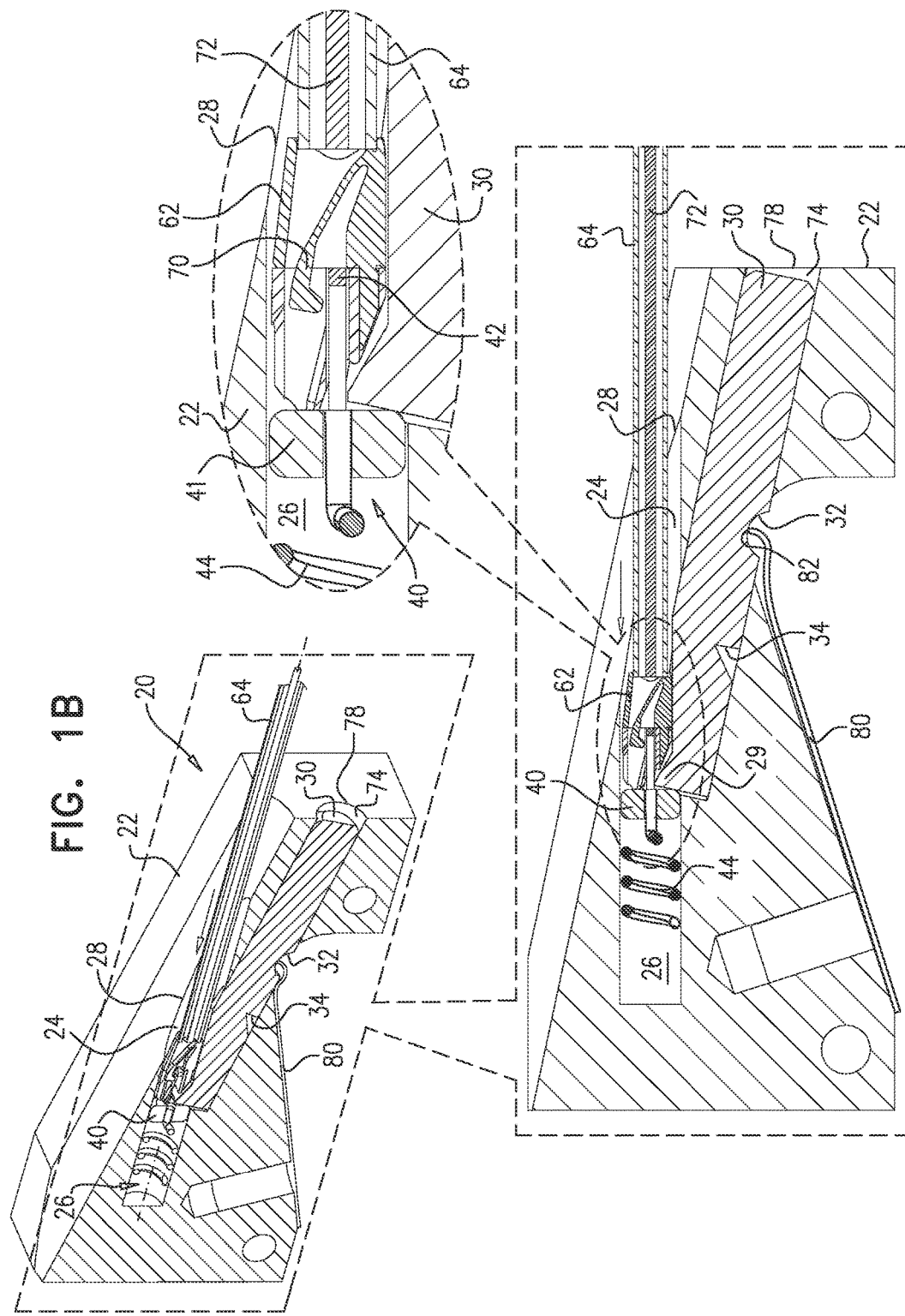

Reference is made to FIGS. 1A-F, which are schematic illustrations of an anchor-handling device 20, configured to facilitate handling of at least one tissue anchor 40, in accordance with some applications of the invention. Device 20 comprises a housing 22 that defines a channel 24, an anchor-storage zone 26 (e.g., at a distal end of the channel) and an opening 28 (e.g., at a proximal end of the channel) that provides access to the channel and the anchor-storage zone. Typically, there is a smooth transition between anchor-storage zone 26 and channel 24. Device 20 further comprises a retaining member, such as a pin 30, which is configured to retain tissue anchor 40 in zone 26, and to stop retaining the tissue anchor in response to a sufficient proximally-directed force applied to the tissue anchor. That is, when a proximally-directed force that is greater than a predetermined threshold force is applied to tissue anchor 40, the retaining member stops retaining (e.g., releases) the tissue anchor.

Typically, the retaining member (e.g., pin 30) has a retaining state in which it retains tissue anchor 40 within zone 26, and is moved out the retaining state when the sufficient proximally-directed force is applied to the tissue anchor. FIG. 1A shows, in accordance with some applications of the invention, pin 30 in a retaining state thereof, in which at least a portion 29 (e.g., an obstructing portion, and/or a distal portion) of the pin is disposed within channel 24 (e.g., proximal to anchor 40), thereby retaining the anchor in zone 26 by obstructing proximal movement of the tissue anchor. Typically, portion 29 obstructs proximal movement of anchor 40 by engaging and/or obstructing core 41 of the anchor (described hereinbelow).

It is to be noted that although pin 30 is shown as being generally cylindrical (i.e., having a generally circular transverse cross-section), the term "pin", as used throughout the present application, including the specification and the claims, may include a pin having a different shape (e.g., having a noncircular transverse cross-section). For example, pin 230 (described hereinbelow with reference to FIGS. 4A-5C) typically has a rectangular cross-section.

FIG. 1A shows an anchor driver 60 being advanced toward opening 28 of channel 24, and FIG. 1B shows the anchor driver having been further advanced into and through channel 24, to anchor 40. As more clearly shown in FIGS. 1A and 1F, opening 28 is typically beveled (i.e., disposed at an angle smaller than 90 degrees to a longitudinal axis of channel 24), such that the opening has a greater area than does a transverse cross section of the channel, thereby facilitating introduction of driver 60 into the channel. It is to be noted that the shape of opening 28 provides a proximal region 25 in which channel 24 is at least half open on a lateral side (i.e., at least half of the circumferential surface of the channel is missing). This shape thereby facilitates placement of a driver head 62 of driver 60 in proximal region 25 of channel 24, e.g., by reducing a requirement for the driver to be aligned with the channel before its introduction into the channel. Driver 60 (e.g., head 62 thereof) can subsequently be advanced further into channel 24, using region 25 as a guide track.

Driver 60 typically comprises an anchor-engaging head 62 at a distal end of the driver, and a shaft 64 proximal to the anchor-engaging head. Shaft 64 is flexible and advanceable (e.g., transcatheterally) through vasculature of a subject, and typically has a length greater than 20 cm, and/or less than 2.5 m, such as greater than 50 cm and/or less than 1.5 m, e.g., between 0.9 m and 1.2 m. For some applications, driver 60 comprises a handle 66 at a proximal end of shaft 64, the handle comprising an adjuster 68 (e.g., a switch or a lever) configured to actuate engaging head 62.

Tissue anchor 40 typically comprises a core 41, a tissue-engaging member 44 coupled to a distal side of the core, and a coupling head 42 coupled to a proximal side of the core.

Engaging head 62 is configured to be reversibly couplable to tissue anchor 40 (e.g., to coupling head 42 thereof), so as to facilitate acquisition of the anchor from device 20, driving of the anchor into tissue of the subject, and subsequent release of the anchor and withdrawal of driver 60 from the subject. For example, actuation of engaging head 62 by adjuster 68 may comprise transitioning the engaging head between (i) an open state in which the engaging head is configured to receive and/or release anchor 40 (FIGS. 1A-B), and (ii) a closed state in which the engaging head, having received the anchor (FIG. 1C), is coupled (e.g., locked) to the anchor.

FIG. 1B shows engaging head 62 having received anchor 40, but not yet coupled (e.g., locked) to the anchor. It is to be noted that in this position part of driver 60 (e.g., head 62) is disposed (e.g., sandwiched) between part of the retaining member (e.g., portion 29) and part of the anchor (e.g., coupling head 42).

Figure 1C:
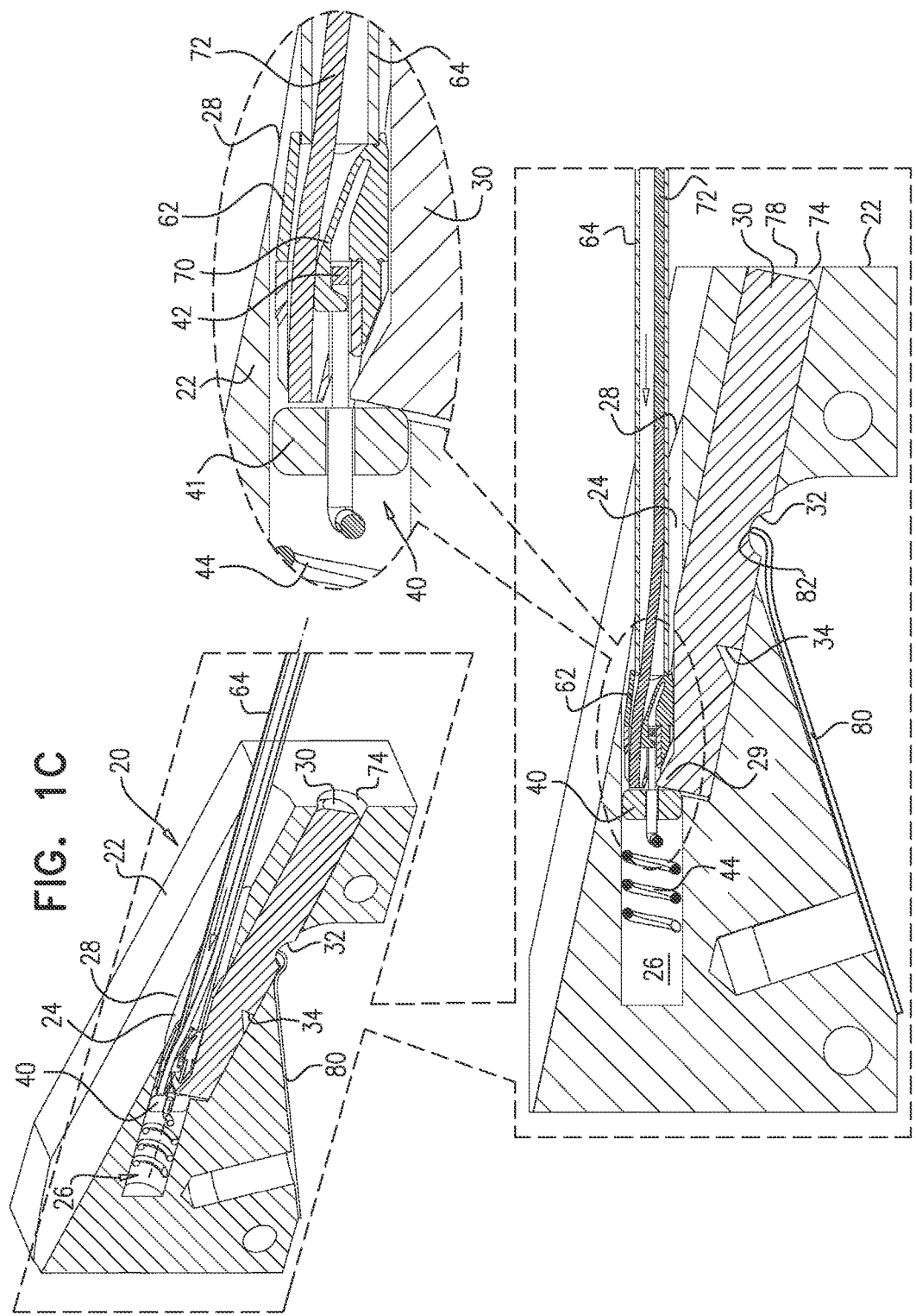

FIG. 1C shows engaging head 62 being coupled (e.g., locked) to anchor 40. For some applications of the invention, engaging head 62 comprises a detent 70 that is transitioned into the closed state when a controller, such as a rod or a wire 72, is moved distally by adjuster 68, and automatically transitions back into the open state when the wire is withdrawn. FIG. 1C shows wire 72 having been moved distally into engaging head 62, and detent 70 having been pushed into the closed state, thereby coupling the engaging head to anchor 40 (e.g., to coupling head 42 thereof).

Figure 1D:
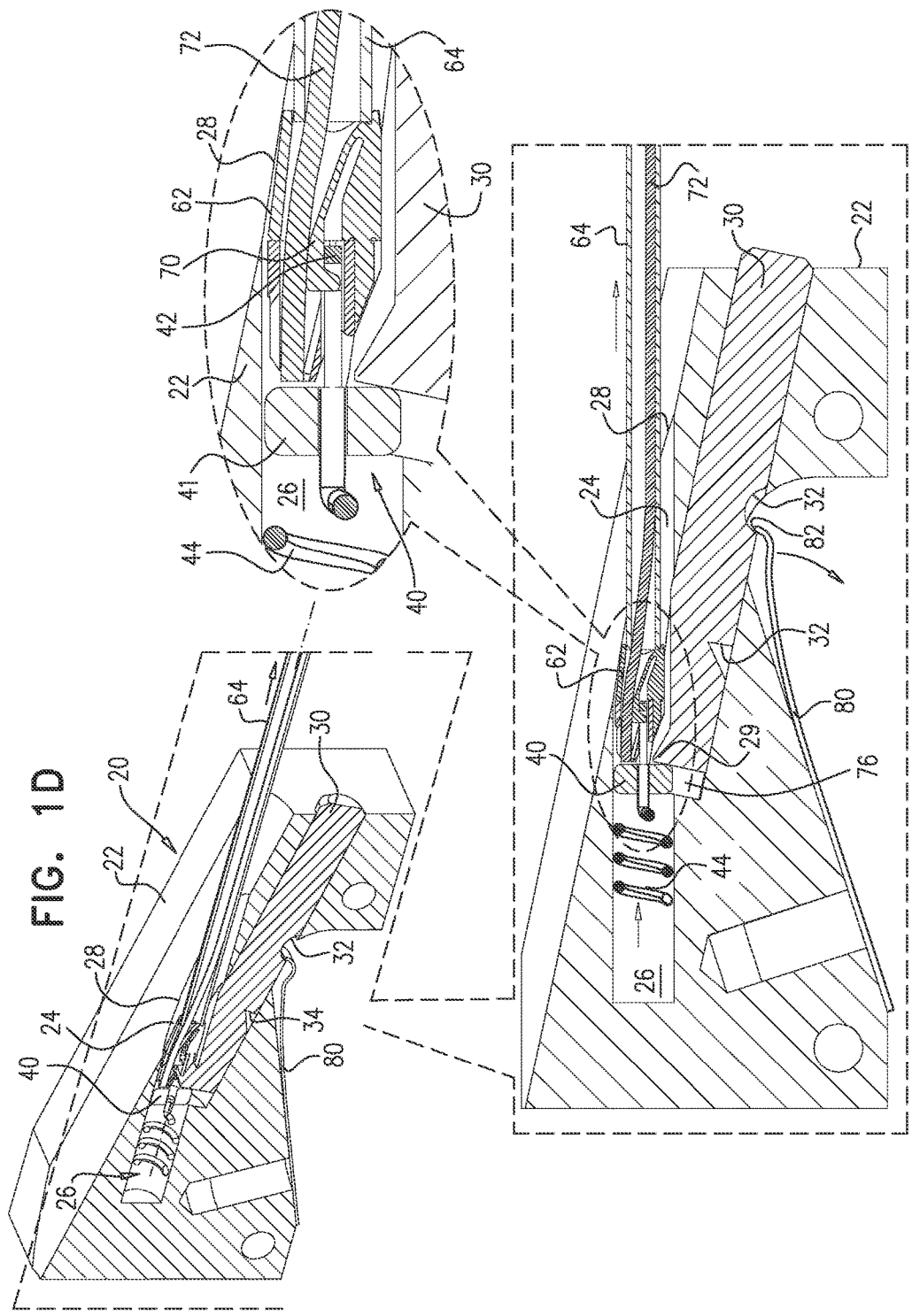

FIGS. 1D-E show anchor 40 being withdrawn proximally from zone 26 of channel 24 by the sufficient proximally-directed force being applied to the anchor by driver 60. As described hereinabove, in response to the sufficient proximally-directed force applied to the tissue anchor (i.e., if the proximally-directed force is greater than the pre-determined threshold force), the retaining member (e.g., pin 30) stops retaining the tissue anchor in zone 26. For example, and as shown in FIGS. 1D-E, the sufficient proximally-directed force overcomes the retention provided by pin 30 and pushes portion 29 of pin 30 out of the channel and into a chamber 74 that is in fluid communication with the channel (at least part of pin 30 thereby sliding within the chamber).

It is hypothesized that this configuring of device 20 to require that the sufficient proximally-directed force be applied to tissue anchor 40 prevents inadvertent movement and/or exit of the tissue anchor (e.g., due to general transport or handling of the device), and/or withdrawal of the anchor by driver 60 when the driver is sub-optimally coupled to the anchor.

For some applications, a first end 76 of chamber 74 is in fluid communication with channel 24, housing 22 defines an opening 78 at a second end of the chamber, and the pushing of portion 29 of pin 30 by the sufficient proximally-directed force pushes a second (e.g., proximal) portion 31 of the pin out of opening 78. This feature and advantages thereof are described in more detail hereinbelow. Typically, chamber 74 has a proximal-distal longitudinal axis that is disposed at between 5 and 30 degrees, e.g., 5-20 degrees (e.g., 5-15 degrees or 10-20 degrees, such as between 11 and 14 degrees) with respect to the longitudinal axis of channel 24. It is hypothesized that, for some applications, this angular disposition of the channel and chamber facilitates the above described movement of pin 30 in response to the sufficient proximally-directed force applied to the tissue anchor.

Figure 1F:
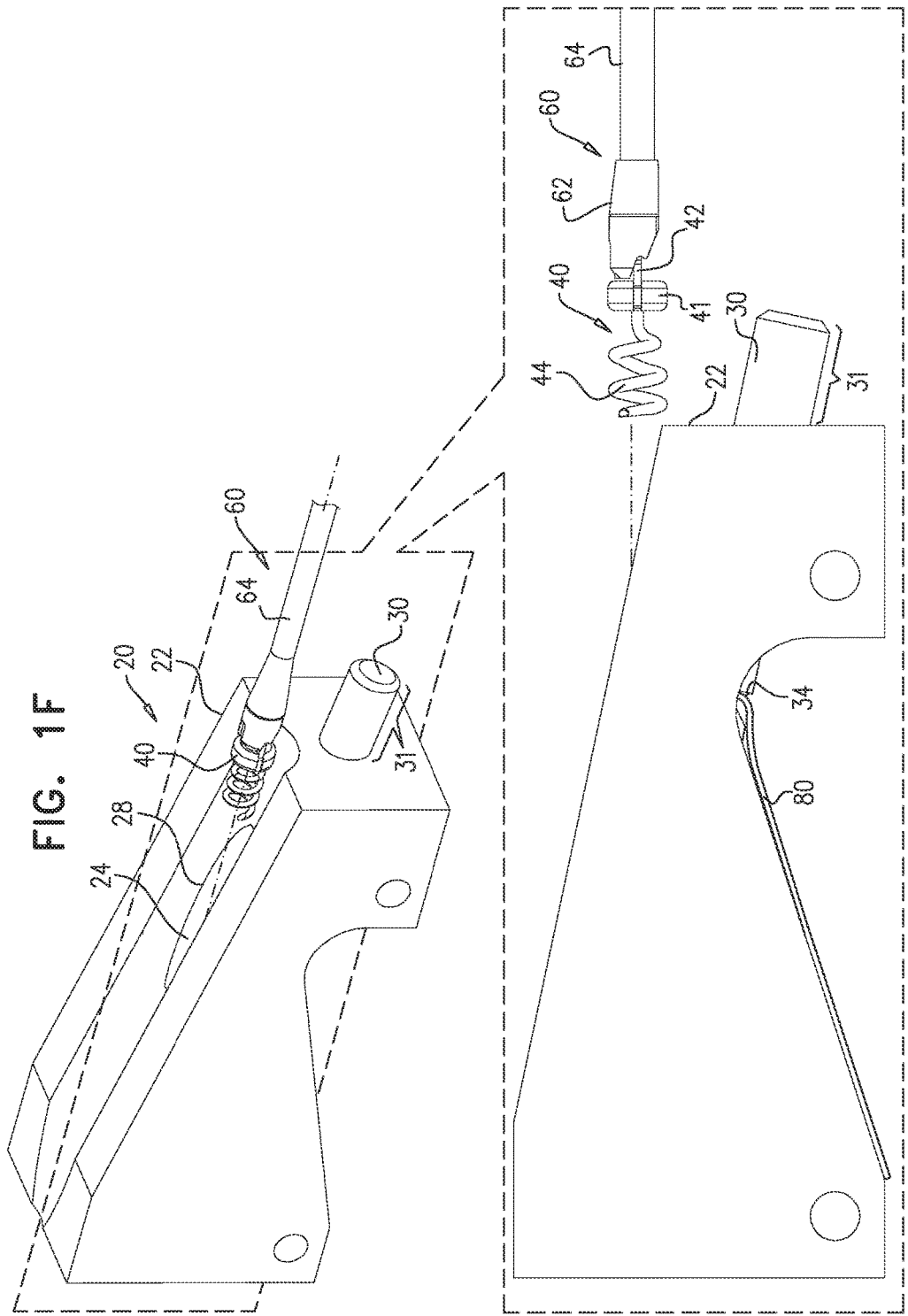

FIG. 1F shows anchor 40 having been fully withdrawn out of channel 24 via opening 28. Once anchor 40 has been fully withdrawn, driver 60 may be used to anchor tissue anchor 40 to tissue of a subject, e.g., by driving tissue-engaging member 44 (FIG. 1A) of the anchor into the tissue. It may be used as a tissue anchor as is known in the art. For example, using driver 60, anchor 40 may be advanced through a transluminal implant-delivery system and used to couple an implant to tissue of a subject, e.g., as described hereinbelow with reference to FIGS. 3A-C.

For some applications, device 20 comprises an inhibitor, configured to configure the retaining member (e.g., pin 30) to (i) retain the tissue anchor in anchor-storage zone 26, and (ii) to stop retaining the tissue anchor in response to the sufficient proximally-directed force. For example, the inhibitor may comprise an inhibitor tongue 80, that has a pin-contacting portion 82 (e.g., a pin-contacting surface) that is in contact with pin 30, and that provides resistance that (i) inhibits sliding of the pin through chamber 74 (e.g., prevents sliding of the pin in response to an insufficient proximally-directed force, i.e., a proximally-directed force that is less than the pre-determined threshold force), and (ii) allows sliding of the pin through the chamber in response to the sufficient proximally-directed force that is greater than the pre-determined threshold force being applied to tissue anchor 40. Pin-contacting portion 82 is typically held in contact with pin 30 by a spring mechanism. For example, and as shown in FIGS. 1A-F, inhibitor tongue 80 may comprise an elastically-deformable (e.g., shape-memory) material, and may be coupled to housing 22 by in a manner in which the inhibitor tongue itself provides the spring mechanism.

For some applications, pin 30 defines a cavity 32 therein (e.g., a recess or a notch in a lateral side of the pin), in which pin-contacting portion 82 is typically disposed while anchor 40 is disposed within anchor-storage zone 26 (e.g., in a state in which the device is provided). For such applications, portion 82 serves as a detent. For such applications, cavity 32 and inhibitor tongue 80 are configured such that when a proximally-directed force equal to or greater than the threshold force is applied to anchor 40, pin 30 is pushed against pin-contacting portion 82, and inhibitor tongue 80 responsively deforms such that the pin-contacting portion moves out of cavity 32, allowing pin 30 to move further proximally (FIG. 1D). Typically, for such applications, once portion 82 has moved out of cavity 32, a proximally-directed force that is smaller than the threshold force is sufficient to move pin 30 further proximally. That is, once the initial resistance provided by the inhibitor is overcome, anchor 40 is further withdrawable using a smaller force than that required to overcome the initial resistance.

(It will be understood by those skilled in the art that it is possible to use other configurations to achieve a behavior similar to that described above. For example, housing 22 may define a cavity, and pin 30 may comprise a flexible protrusion that extends into the cavity of the housing.)

For some applications, the inhibitor (e.g., tongue 80) provides the resistance by applying friction against the retaining member (e.g., pin 30). For example, pin-contacting portion 82 may comprise a high-friction pin-contacting surface.

Figure 2:
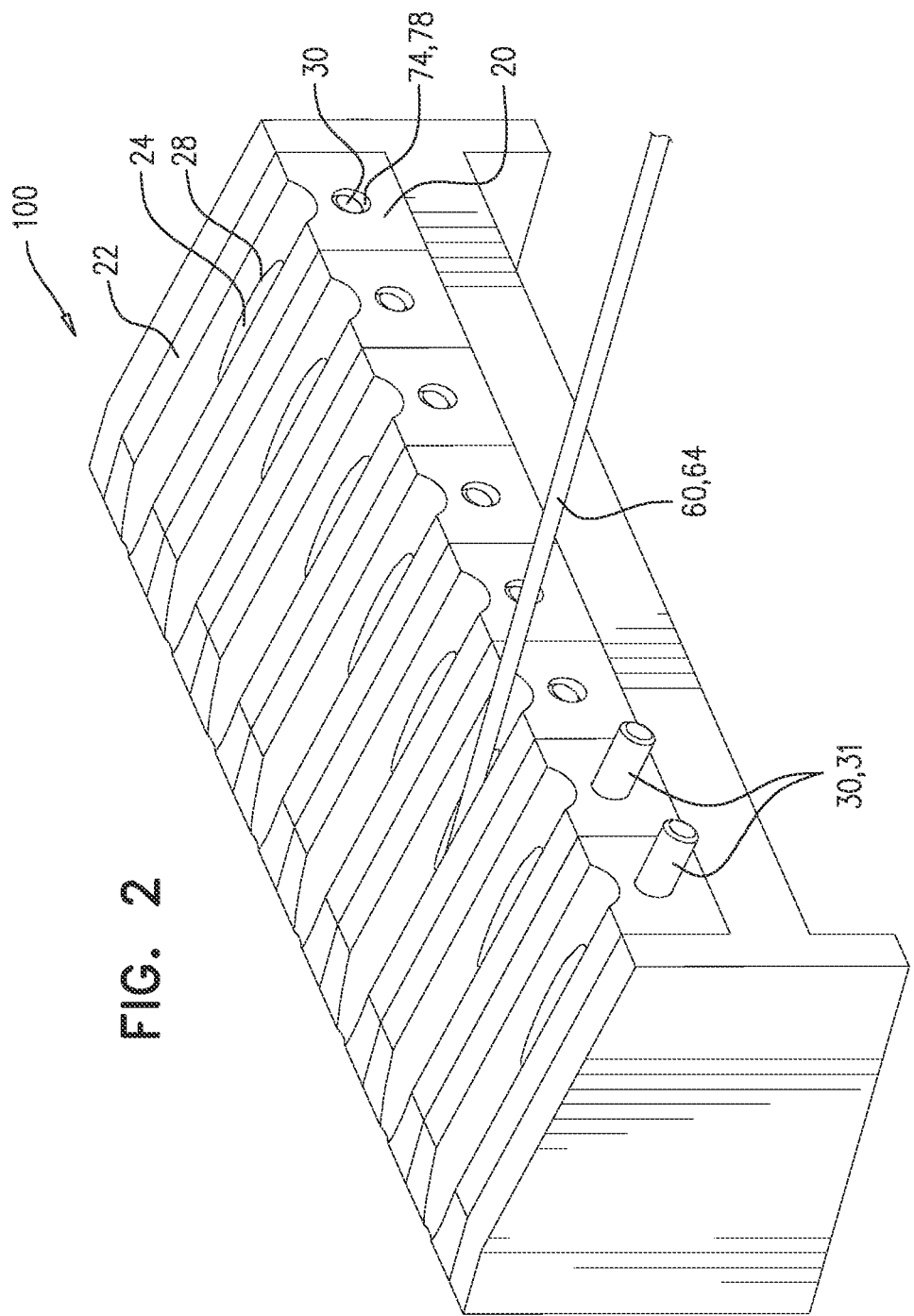
FIG. 2 is a schematic illustration of a multiple-anchor-handling device, in accordance with some applications of the invention.

Reference is made to FIG. 2, which is a schematic illustration of a multiple-anchor-handling device 100, in accordance with some applications of the invention. Device 100 defines a plurality of channels 24, each channel having a respective proximal opening 28 and a respective anchor-storage zone 26 that is configured to store a respective tissue anchor 40 (zone 26 and anchor 40 not visible in FIG. 2). Typically, device 100 further comprises a plurality of retaining members (e.g., pins 30), each retaining member being configured to retain a respective tissue anchor in its respective anchor-storage zone 26, and to stop retaining the respective tissue anchor in response to the sufficient proximally-directed force being applied to its respective tissue anchor. For some applications, device 100 comprises a plurality of devices 20. For example, device 100 may comprise a plurality of housings 22, each housing defining exactly one channel 24 and exactly one retaining member (e.g., pin 30).

As described hereinabove, for some applications, the sufficient proximally-directed force pushes a second (e.g., proximal) portion 31 of pin 30 out of opening 78 of chamber 74. Therefore, when driver 60 is withdrawn proximally, movement of portion 31 toward and/or out of opening 78 indicates that anchor-engaging head 62 has been successfully coupled to tissue anchor 40, and that the tissue anchor is also being withdrawn proximally. Thus, during an initial partial withdrawal of driver 60, movement of portion 31 toward and/or out of opening 78 provides an indication to the operator (e.g., physician) to continue to withdraw driver 60, whereas absence of such movement of portion 31 provides an indication to the operator to reattempt coupling of the driver to tissue anchor 40.

Following removal of anchor 40 from channel 24, portion 31 remains exposed from opening 78. This may be particularly useful for a physician using a multiple-anchor-handling device, such as device 100, e.g., to prevent the physician inadvertently attempting to obtain an anchor from an empty zone 26. That is, portion 31 functions as an empty-housing indicator.

For some applications, pin 30 defines a second cavity 34 therein (e.g., a second notch in a lateral side of the pin), disposed closer to distal portion 29 than is cavity 32. Second cavity 34 is positioned such that when (1) distal portion 29 is no longer obstructing anchor 40, and (2) second portion 31 is exposed out of opening 78, pin-engaging portion 82 of inhibitor tongue 80 moves into the second cavity (e.g., as shown in FIG. 1E). In this state, tongue 80 inhibits pin 30 from moving distally back into housing 22, thereby increasing the reliability of portion 31 functioning as an empty-housing indicator. For some applications, and as shown in FIGS. 1A-F, second cavity 34 is shaped such that once portion 82 has moved into (e.g., engaged) second cavity 34, the moving of portion 31 back into housing 22 requires a distally-directed force that is more than twice as great (in the opposite direction) as the threshold force that was previously required to move portion 31 out of the housing. For example, the moving of portion 31 back into housing 22 may be in effect prevented.

Figure 3A:
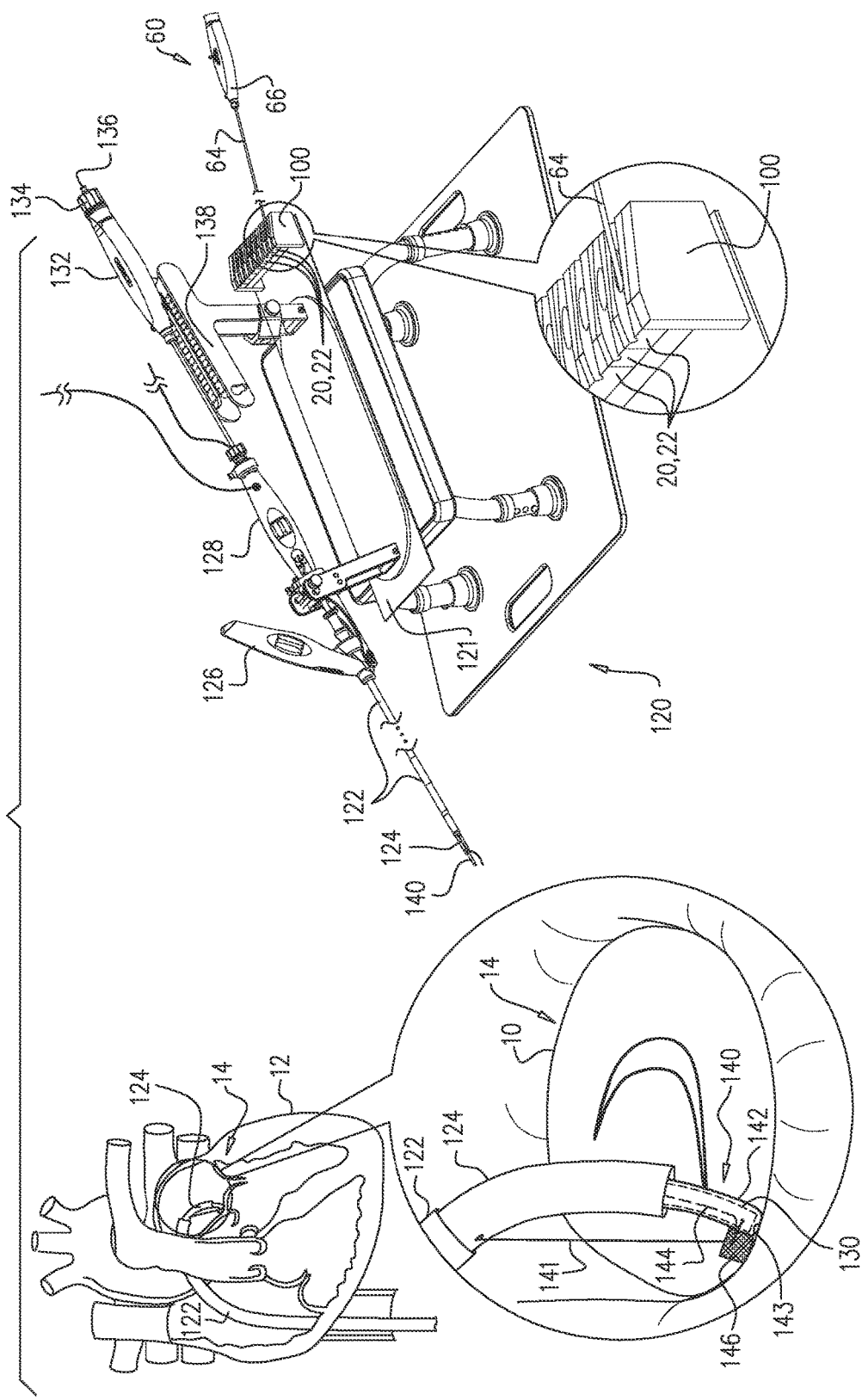
FIGS. 3A-C are schematic illustrations of a system for transcatheter delivery of an implant, and anchoring of the implant using an anchor driver and a plurality of anchors provided in the multiple-anchor-handling device of FIG. 2, in accordance with some applications of the invention.
Figure 3B:
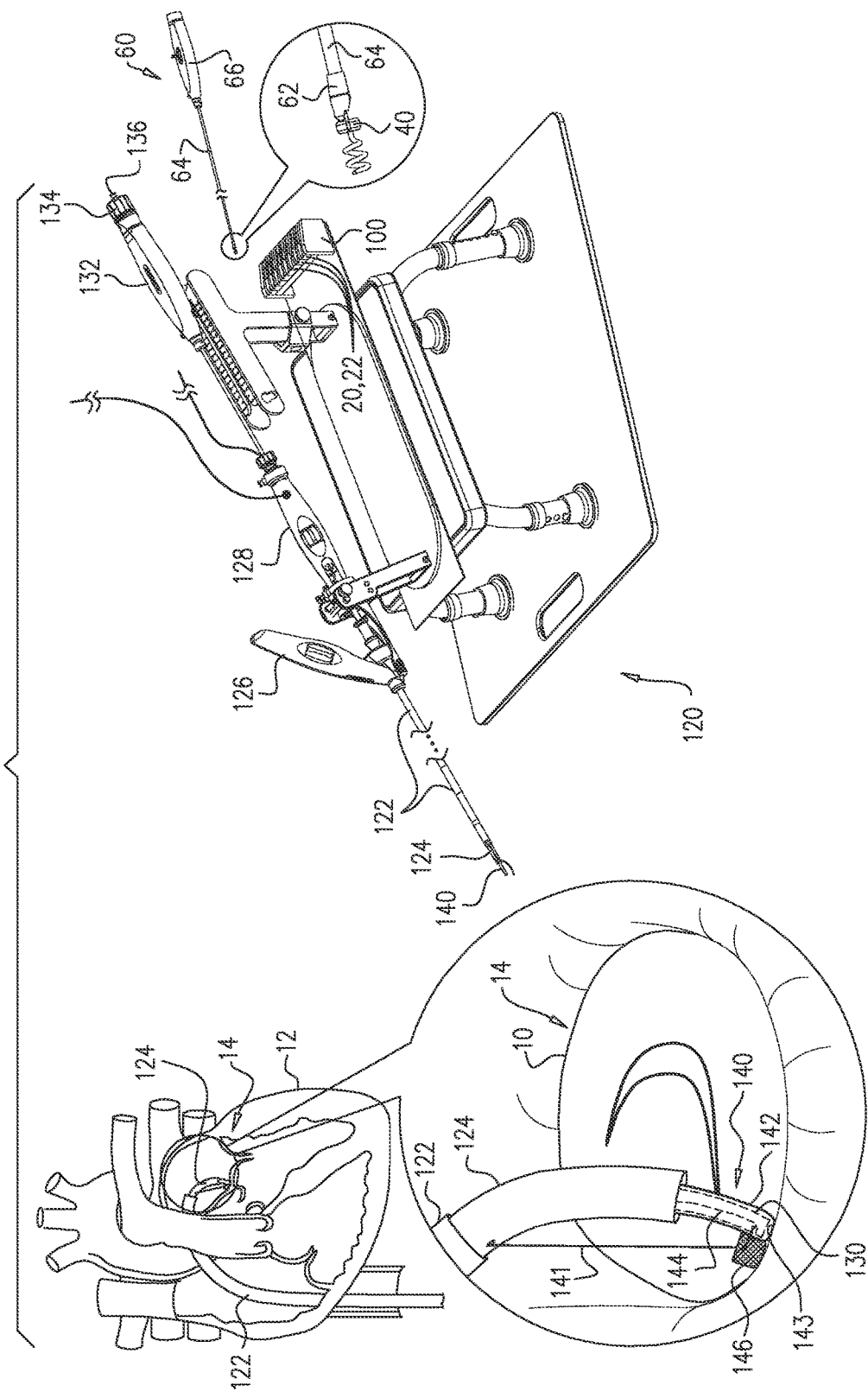
Figure 3C:
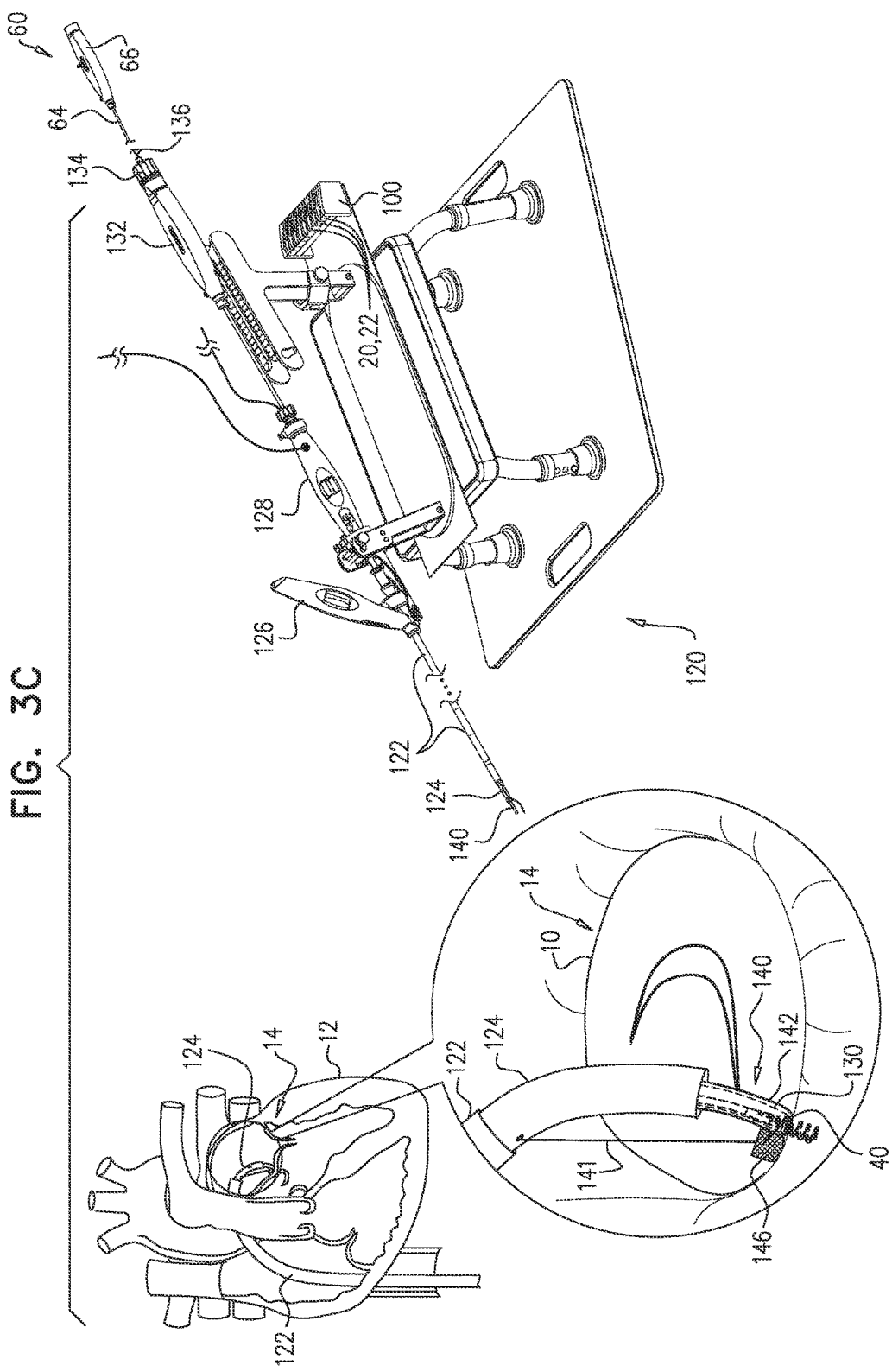

Reference is made to FIGS. 3A-C, which are schematic illustrations of a multi-component tubular system 120 for transcatheter delivery of an implant 140, and anchoring of the implant using anchor driver 60 and a plurality of anchors 40 provided in multiple-anchor-handling device 100, in accordance with some applications of the invention. Implant 140 comprises an annuloplasty structure comprising a sleeve 142, a flexible elongated contracting member 144 that extends along the sleeve, and an adjustment mechanism 146 which facilitates contracting and expanding of the annuloplasty structure. Typically, adjustment mechanism 146 comprises a spool around which successive portions of member 144 are wound in order to contract the annuloplasty structure after implantation.

Implant 140 is configured to be anchored to an annulus 10 of a valve of the heart 12 of a subject, such as a mitral valve 14 of the subject, and to change a dimension of the annulus when contracted or expanded using adjustment mechanism 146.

System 120 comprises one or more steerable catheters, and typically comprises an outer catheter 122 and an inner catheter 124 that is advanceable through the outer catheter. Outer catheter 122 is advanceable and steerable using a first handle 126, and inner catheter 124 is advanceable and steerable using a second handle 128. Typically, second handle 128 is couplable (e.g., lockable) to first handle 126, e.g., after advancement of catheter 124 through catheter 122.

Implant 140 is typically (1) advanceable through inner catheter 124 in a delivery configuration in which adjustment mechanism 146 is disposed on an axis defined by sleeve 142, distally to a distal end 143 of the sleeve, and (2) transitionable into an anchoring configuration in which the adjustment mechanism is disposed laterally to the sleeve (FIG. 3A shows implant 140 in the anchoring configuration thereof). Advancement of implant 140 distally out of catheter 14 is typically controllable using a third handle 132 which is slidably coupled to handle 128, e.g., via a handle-sliding track 138.

A portion of sleeve 142 (e.g., distal end 143) is placed against annulus 10 (FIG. 3A). Typically, system 120 further comprises an implant-decoupling channel 130, disposed within sleeve 142, and slidable progressively proximally out of the sleeve, e.g., using a knob 134 coupled to a proximal end of channel 130. Typically, channel 130 is used to hold the portion of sleeve 142 (e.g., distal end 143) against annulus 10.

FIG. 3A shows anchor driver 60 (e.g., anchor-engaging head 62 thereof) being coupled to a first anchor 40 (not visible in FIG. 3A) which is disposed within a first housing 22 of device 100, as described hereinabove (e.g., with reference to FIGS. 1A-C). Subsequently, as shown in FIG. 3B, anchor driver 60 is withdrawn from the first housing 22 of device 100, while coupled to anchor 40. Anchor 40 is then advanced into system 120 by advancing driver 60 (e.g., anchor-engaging head 62 and shaft 64 thereof) through the system (FIG. 3C). Typically, and as shown in FIG. 3C, the anchor is introduced into system 120 via a port 136 at a proximal end of handle 132, and is slid through channel 130, into sleeve 142, and is screwed through sleeve 142 (e.g., distal end 143 thereof) and into annulus 10.

Driver 60 is subsequently removed from system 120, coupled to a second anchor 40 disposed in a second housing 22 of device 100, and reintroduced into the system. Channel 130 is withdrawn slightly proximally from the sleeve, and a second portion of the sleeve is held against a second site on annulus 10 before the second anchor is driven through sleeve 142, anchoring the second portion of the sleeve to the second site. This process is repeated so as to place and anchor sleeve 142 around at least a portion of annulus 10.

Typically, and as shown in FIGS. 3A-C, device 100 is coupled to system 120 (e.g., the rest of system 120) so as to facilitate access by driver 60 to openings 28 of channels 24 of housings 22. For example, device 100 may be coupled to a stand (e.g., a base-plate) 121 of system 120, and/or may be oriented such that openings 28 face generally the same direction as port 136 of system 120, such that the operator (e.g., a physician) may easily move driver 60 between openings 28 and port 136. Typically, device 100 is positioned such that openings 28 are closer than 1 m and/or greater than 1 cm (e.g., between 1 cm and 1 m, such as between 1 cm and 70 cm, such as between 1 cm and 40 cm) away from port 136 (or another opening through which anchors 40 are introduced into system 120).

Alternatively, device 100 may comprise a standalone unit, not coupled to system 120 or any other system.

Subsequently, implant 140 may be adjusted (e.g., contracted) using an adjustment tool (not shown), advanceable over a guide member 141 to adjustment mechanism 146.

Reference is made to FIGS. 4A-F, which are schematic illustrations of an anchor-handling device 220, configured to facilitate handling of at least one tissue anchor 40, in accordance with some applications of the invention. Device 220 comprises a housing 222 that defines a channel 224 having an anchor-storage zone 226 and an opening 228 that provides access to the channel and the anchor-storage zone. Device 220 further comprises a retaining member, such as a pin 230, which is configured to retain tissue anchor 40 in zone 226, and to stop retaining the tissue anchor in response to a sufficient proximally-directed force applied to the tissue anchor. That is, when a proximally-directed force that is greater than a pre-determined threshold force is applied to tissue anchor 40, the retaining member stops retaining (e.g., releases) the tissue anchor. For some applications FIGS. 4A-F, which show steps in the use of device 220, generally correspond to FIGS. 1A-F, respectively, which show steps in the use of device 20, mutatis mutandis.

Figure 4A:
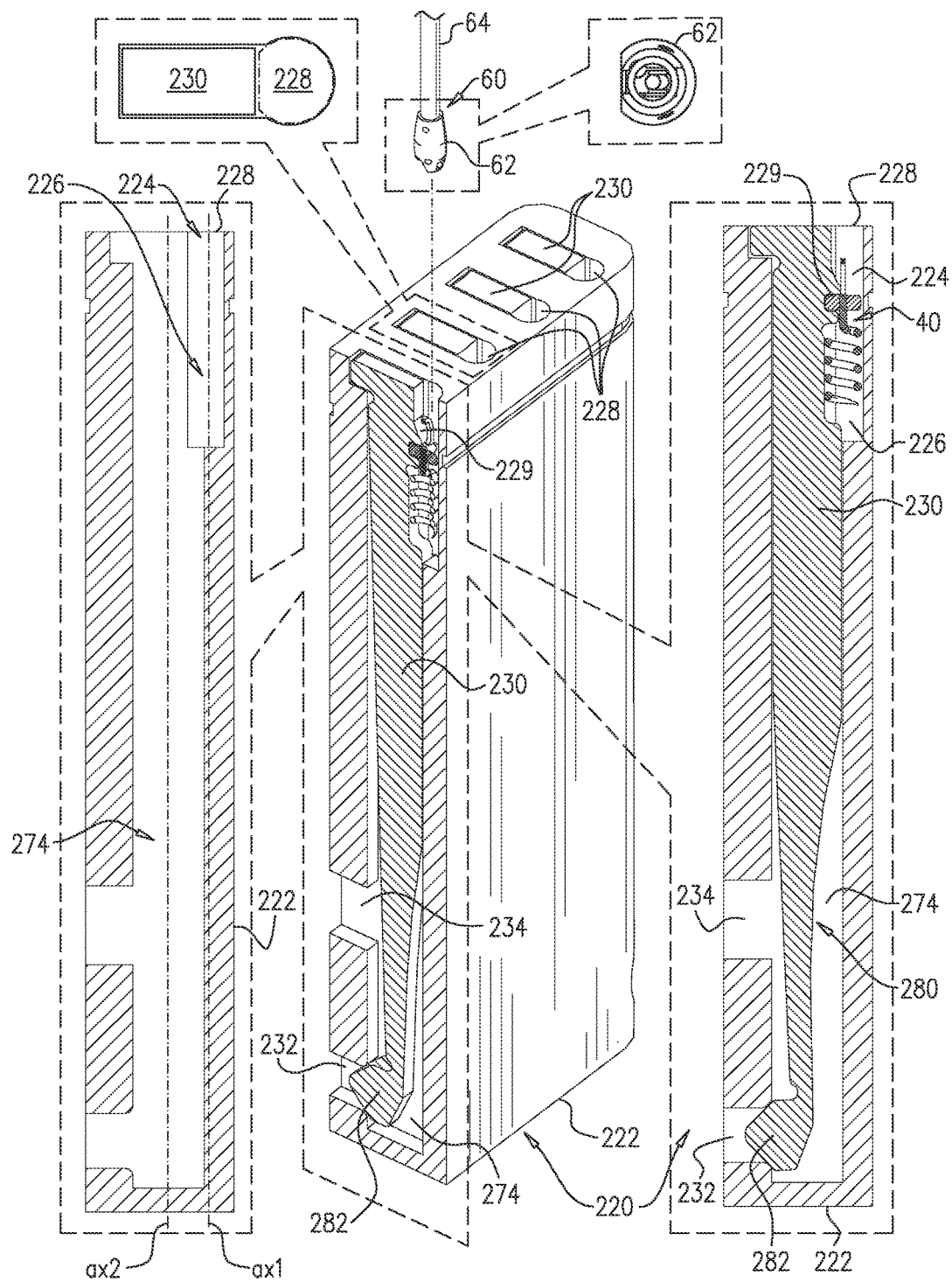

Typically, the retaining member (e.g., pin 230) has a retaining state in which it retains tissue anchor 40 within zone 226, and is moved out the retaining state when the sufficient proximally-directed force is applied to the tissue anchor. FIG. 4A shows, in accordance with some applications of the invention, pin 230 in a retaining state thereof, in which at least a portion 229 (e.g., an obstructing portion) of the pin is disposed within channel 224 (e.g., proximal to anchor 40), thereby retaining the anchor in zone 226 by obstructing proximal movement of the tissue anchor. Typically, portion 229 obstructs proximal movement of anchor 40 by engaging and/or obstructing core 41 of the anchor. Another portion of pin 230 is disposed in a chamber 274, which is defined by housing 222 and is typically in fluid communication with channel 224 (e.g., in the absence of pin 230). Typically, chamber 274 has a central longitudinal axis ax1 that is parallel with a central longitudinal axis ax2 of channel 24.

Similarly to device 20, it is hypothesized that this configuring of device 220 prevents inadvertent movement and/or exit of the tissue anchor (e.g., due to general transport or handling of the device), and/or withdrawal of the anchor by driver 60 when the driver is sub-optimally coupled to the anchor.

Figure 4B:
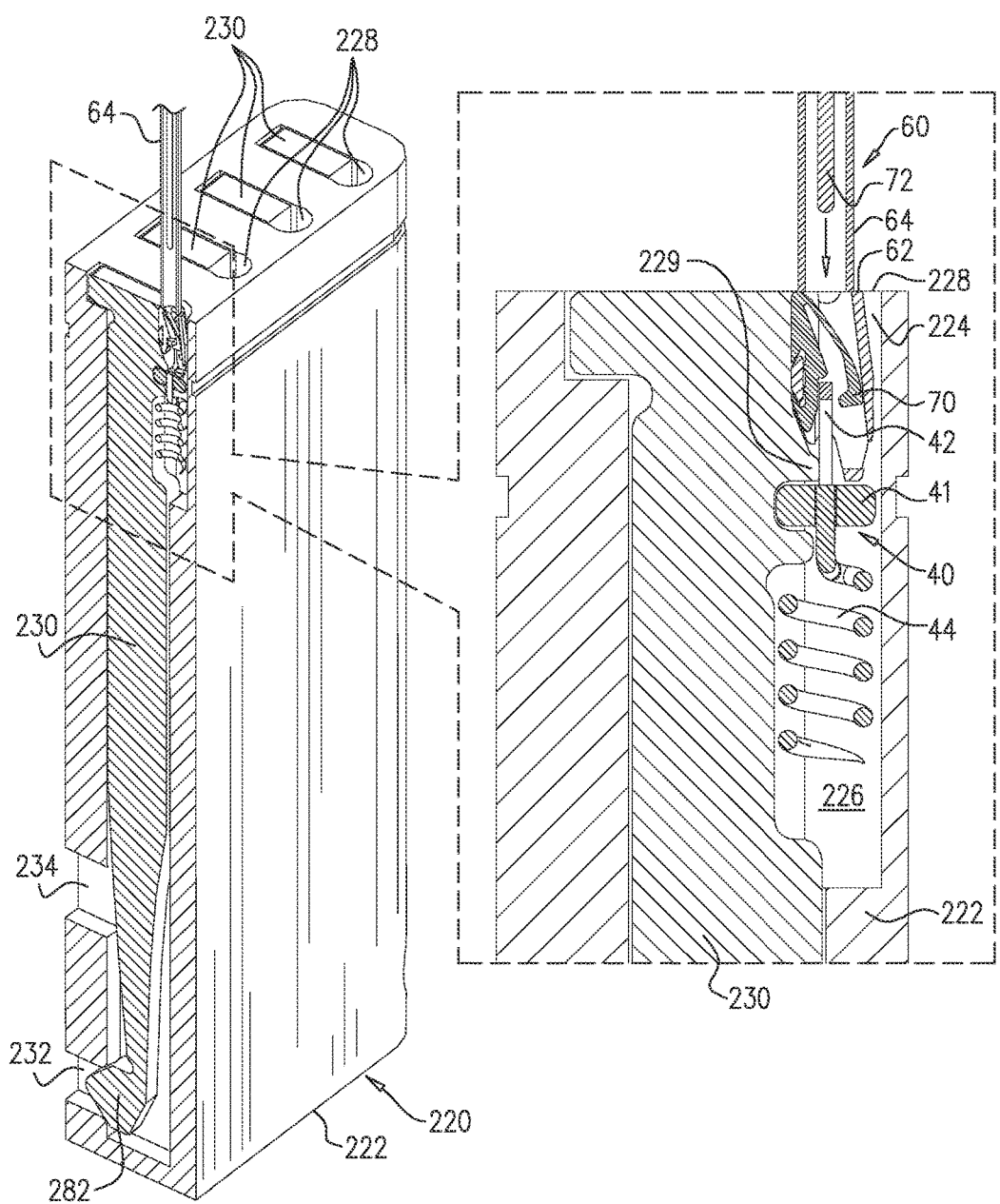

FIG. 4A shows anchor driver 60 (described hereinabove) being advanced toward opening 228 of channel 224, and FIG. 4B shows the anchor driver having been further advanced into and through channel 224, to anchor 40, such that engaging head 62 has received anchor 40, but not yet coupled (e.g., locked) to the anchor. It is to be noted that in this position part of driver 60 (e.g., head 62) is disposed (e.g., sandwiched) between part of the retaining member (e.g., portion 229) and part of the anchor (e.g., coupling head 42).

FIG. 4A shows respective cross-sections of opening 228 and driver head 62, which are typically each rotationally asymmetrical. For some applications, and as shown, the cross-sections each have the shape of an ellipse (e.g., a circle) with a segment (e.g., a circular segment) removed. (For some applications opening 228 (e.g., the shape thereof) is defined partly by housing 222, and partly by pin 230.) Due to this rotational asymmetry, anchor-engaging head 62 is introducible through opening 228 in fewer than all rotational orientations of the head with respect to the opening. For example, head 62 may be introducible through opening 228 only in one or more particular rotational orientations (e.g., one particular orientation of the head) of the head with respect to the opening. This limitation of the rotational orientations in which head 62 may be introduced through opening 228 causes the head to be correctly rotationally oriented for coupling to coupling head 42 of anchor 40, the anchor being stored in zone 226 in a given rotational orientation with respect to the opening. Therefore anchor-engaging head 62 is couplable to anchor 40, without rotating the anchor-engaging head subsequently to introducing the anchor-engaging head through opening 228.

It is to be noted that this orientation-limitation may be applied to device 20, mutatis mutandis, and that the lateral channel opening that provides region 25 of device 20 may be applied to device 220, mutatis mutandis.

Figure 4C:
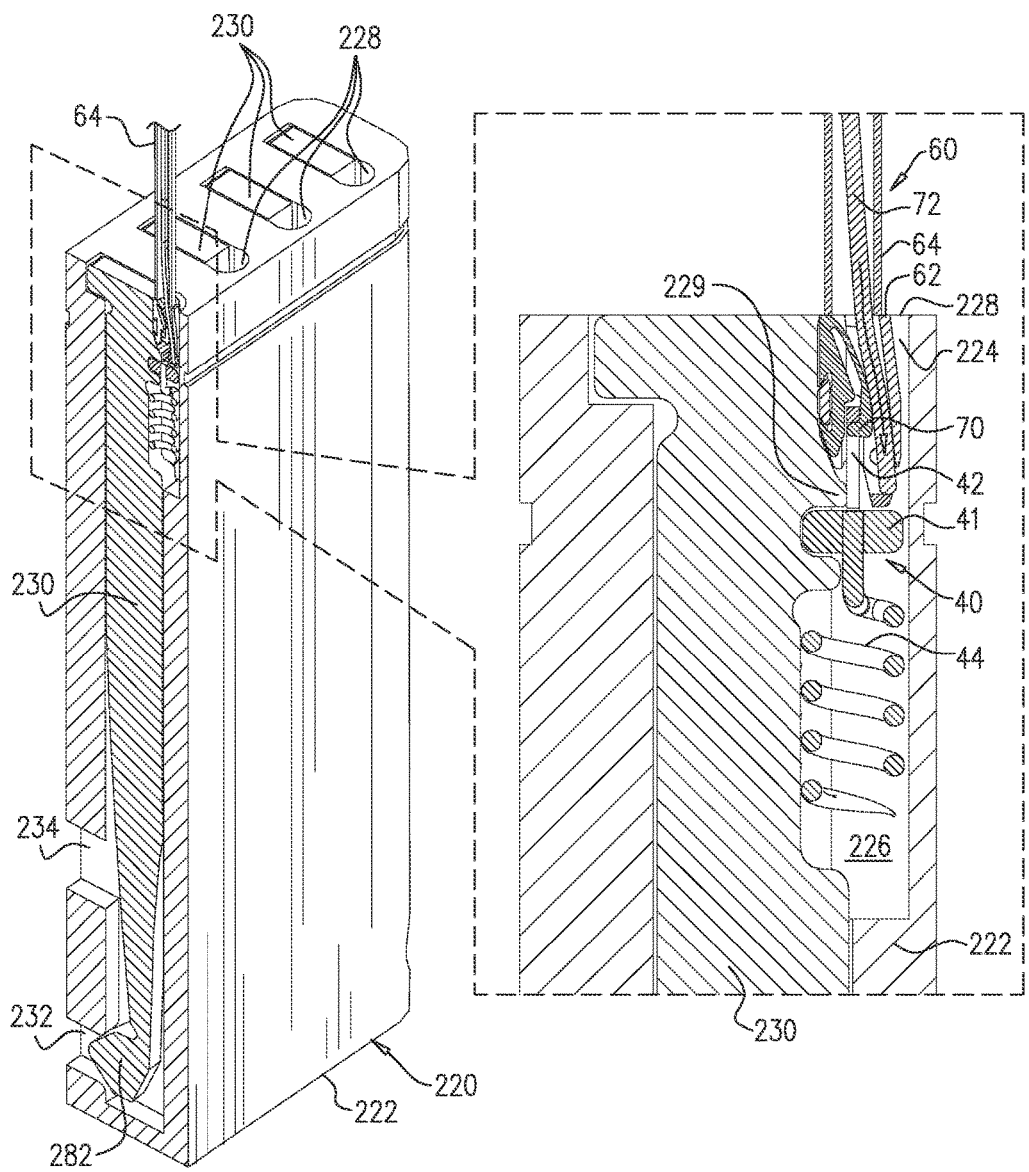

FIG. 4C shows wire 72 having been moved distally into engaging head 62, and detent 70 having been pushed into the closed state, thereby coupling the engaging head to anchor 40 (e.g., to coupling head 42 thereof).

Figure 4D:
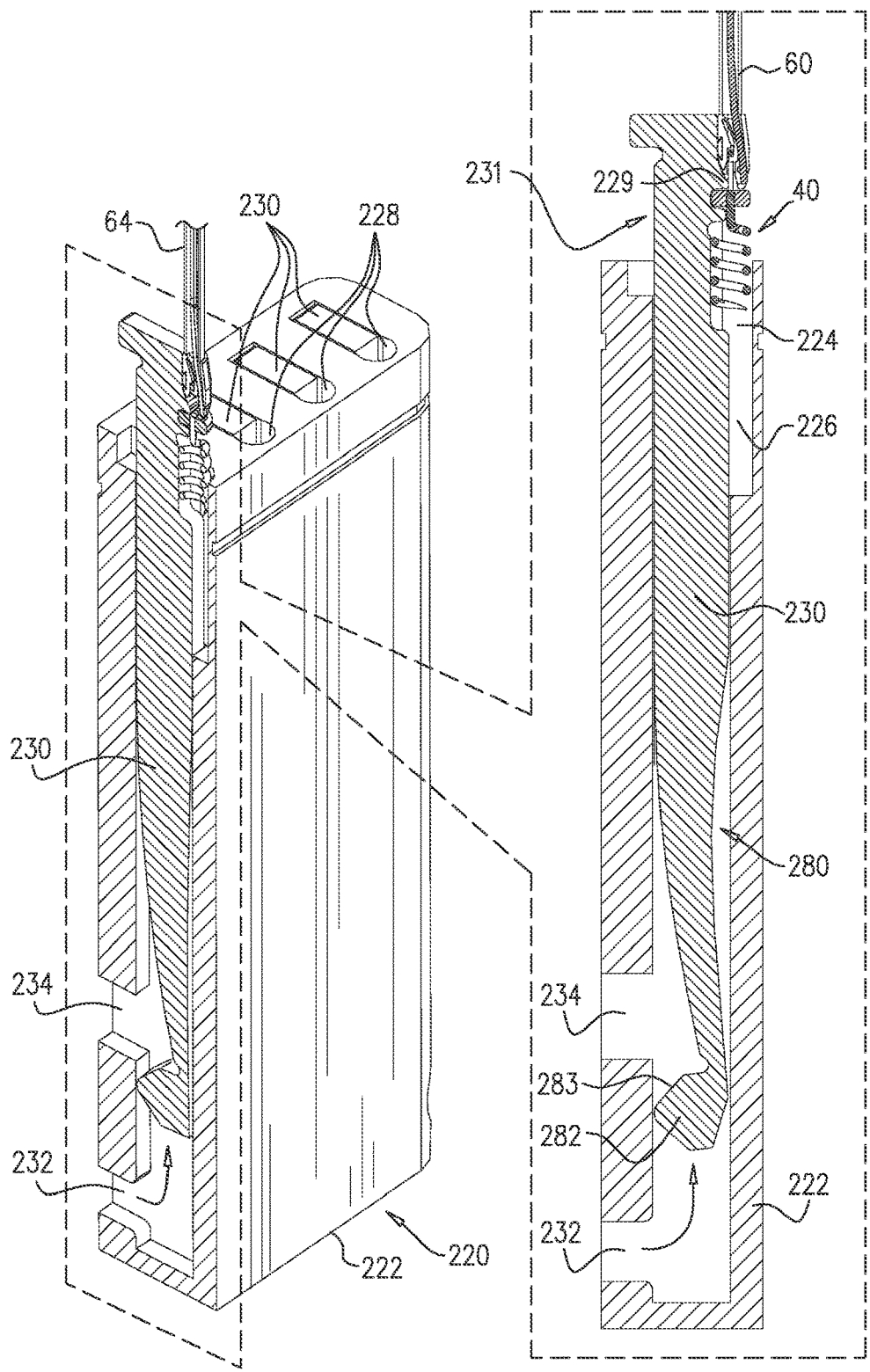
Figure 4E:
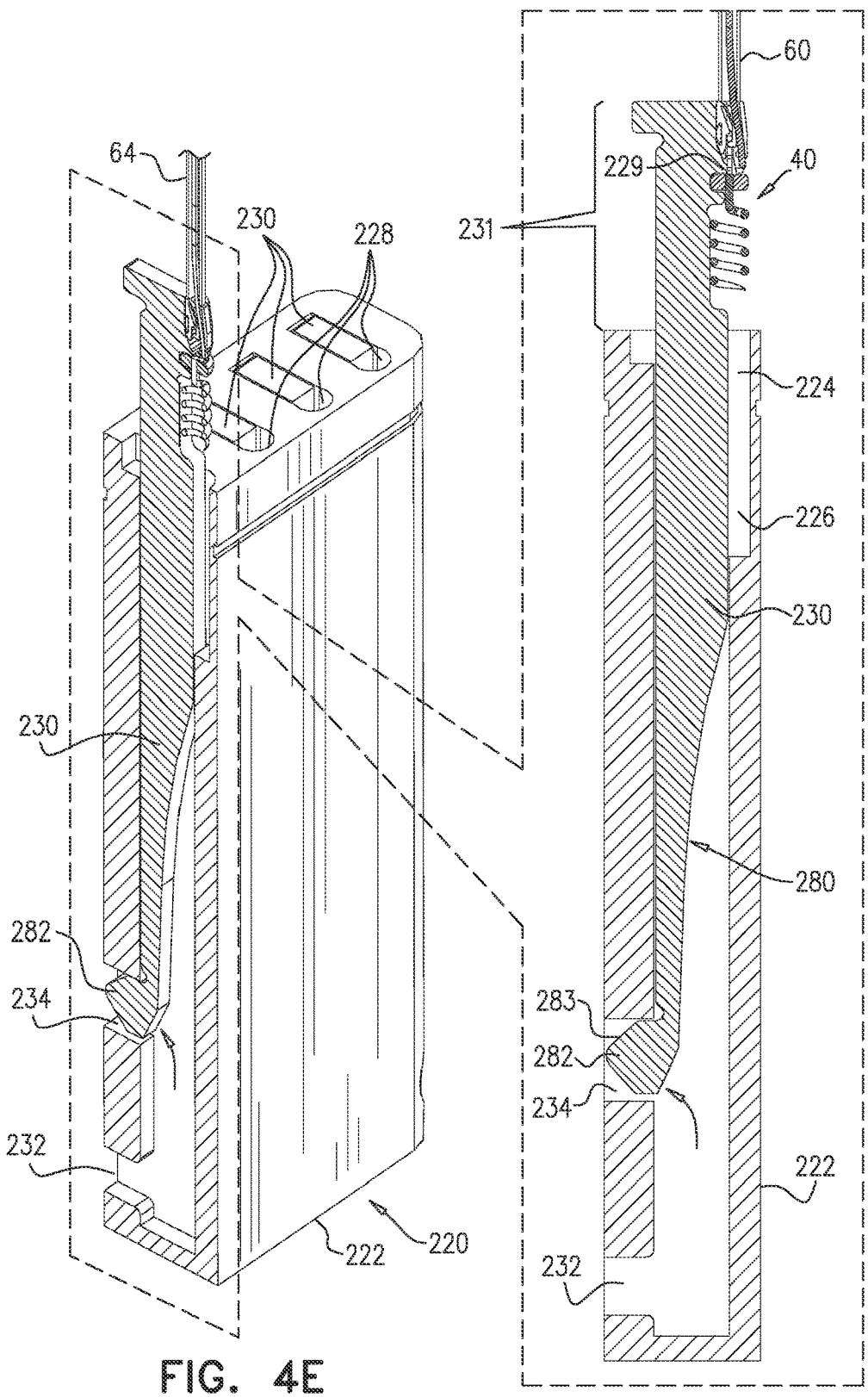

FIGS. 4D-E show anchor 40 being withdrawn proximally from zone 226 by the sufficient proximally-directed force being applied to the anchor by driver 60. As described hereinabove, in response to the sufficient proximally-directed force applied to the tissue anchor (i.e., if the proximally-directed force is greater than the pre-determined threshold force), the retaining member (e.g., pin 230) stops retaining the tissue anchor in zone 226. For example, and as shown in FIGS. 4D-E, the sufficient proximally-directed force overcomes the retention provided by pin 230 such that at least a portion of pin 230 slides within chamber 274, and at least a portion 231 (e.g., a proximal portion) of pin 230 moves out of housing 222.

FIG. 4D shows portion 231 of pin 230 beginning to move out of housing 222, and FIG. 4E shows both portion 231 and anchor 40 disposed outside of the housing, such that pin 230 (e.g., portion 229 thereof) no longer obstructs anchor 40. It is to be noted that for device 220, the portion 229 of pin 230 that obstructs anchor 40 is disposed close to (e.g., within) the portion 231 of pin 230 that becomes exposed from housing 222, whereas for device 20 described hereinabove, the portion 29 of pin 30 that obstructs anchor 40 is disposed at another part (e.g., at the other end) of pin 30 from the portion 31 of pin 30 that becomes exposed from housing. Similarly, portion 229 typically becomes exposed from housing 222 upon withdrawal of anchor 40 from device 20, whereas portion 29 typically remains within housing 22 upon withdrawal of anchor 40 from device 220.

FIG. 4F shows anchor 40 having been fully removed from the housing. For some applications, to facilitate full disengagement of anchor 40 from pin 230, the anchor is moved slightly laterally with respect to pin 30. Once anchor 40 has been fully withdrawn, driver 60 may be used to anchor tissue anchor 40 to tissue of a subject, e.g., as described hereinabove.

Device 220 comprises an inhibitor, configured to configure the retaining member (e.g., pin 30) to (i) retain the tissue anchor in anchor-storage zone 26, and (ii) to stop retaining the tissue anchor in response to the sufficient proximally-directed force. For example, pin 230 may comprise or define a detent 282 that, while anchor 40 is disposed within anchor-storage zone 226, is held by a spring mechanism within a cavity 232 (e.g., a notch) defined in chamber 274, and thereby serves as the inhibitor. For some applications at least a portion 280 of pin 230 is resilient, and thereby provides the spring mechanism. It is to be noted, however, that the scope of the invention includes the use of other spring mechanisms. The inhibitor provides resistance that (i) inhibits sliding of pin 230 through chamber 274, e.g., prevents sliding of the pin in the absence of a sufficient proximally-directed force (e.g., as shown in FIG. 4C), and (ii) stops inhibiting the sliding in response to the sufficient proximally-directed force by detent 282 moving out of cavity 232 (e.g., as shown in FIG. 4D). For example, and as shown, resilient portion 280 deforms (e.g., bends) in response to the sufficient proximally-directed force. This is typically facilitated by detent 282 and a proximal wall of cavity 232 having respective faces that are appropriately angled with respect to each other such that the proximally-directed force is converted into lateral movement of the detent out of the cavity. For example, and as shown, detent 282 may have a beveled edge.

Typically, for such applications, once detent 282 has moved out of cavity 232, a proximally-directed force that is smaller than the threshold force is sufficient to move pin 30 further proximally. That is, once the initial resistance provided by the inhibitor is overcome, anchor 40 is further withdrawable using a smaller force than that required to overcome the initial resistance.

(It will be understood by those skilled in the art that it is possible to use other configurations to achieve a behavior similar to that described above. For example, housing 222 may define a protrusion (e.g., a detent), and pin 30 may comprise a cavity (e.g., a notch) into which the protrusion extends.)

For some applications, the inhibitor provides the resistance by applying friction against the wall of cavity 232. For example, pin 230 may have a high-friction wall-contacting surface.

Device 220 is described hereinabove with reference to only one channel 224, zone 226, and restraining member. Typically however, the device defines a plurality of channels 224, each channel having a respective proximal opening 228 and a respective anchor-storage zone 226 that is configured to store a respective tissue anchor 40 (e.g., as described with reference to device 100, mutatis mutandis). Typically, device 220 further comprises a plurality of retaining members (e.g., pins 230), each retaining member being configured to retain a respective tissue anchor in its respective anchor-storage zone 226, and to stop retaining the respective tissue anchor in response to the sufficient proximally-directed force being applied to its respective tissue anchor.

As described hereinabove, for some applications, the sufficient proximally-directed force pushes portion 231 of pin 30 out of housing 222. Therefore, as driver 60 is withdrawn proximally, movement of portion 231 out of housing 222 indicates that anchor-engaging head 62 has been successfully coupled to tissue anchor 40, and that the tissue anchor is also being withdrawn proximally. Thus, during an initial partial withdrawal of driver 60, movement of portion 231 out of housing 222 provides an indication to the operator (e.g., physician) to continue to withdraw driver 60, whereas absence of such movement of portion 231 provides an indication to the operator to reattempt coupling of the driver to tissue anchor 40.

Following removal of anchor 40 from channel 224, portion 231 remains exposed outside of housing 222. This may be particularly useful for a physician using device 220, e.g., to prevent the physician inadvertently attempting to obtain an anchor from an empty anchor-storage zone 226. That is, portion 231 functions as an empty-housing indicator.

For some applications, a second cavity 234 is defined in chamber 274 (e.g., a second notch in a wall of the chamber), disposed more proximally with respect to housing 222 than is cavity 232. Second cavity 234 is positioned such that when (1) portion 229 is no longer obstructing anchor 40, and (2) portion 231 is exposed out of opening 278, detent 282 (i.e., the inhibitor) moves into the second cavity (e.g., as shown in FIG. 4E). In this state, the detent inhibits pin 230 from moving distally back into housing 222, thereby increasing the reliability of portion 31 functioning as an empty-housing indicator.

For some applications, and as shown in FIGS. 1A-F, second cavity 234 is dimensioned and/or shaped such that once detent 282 has moved into (e.g., engaged) second cavity 234, a distally-directed force required to return portion 231 into housing 222 (e.g., to return device 220 into its retaining state) is more than twice as great (in the opposite direction) as the threshold force that was previously required to move portion 231 out of the housing, and to remove anchor 40 from the housing. For example, and as shown, cavity 234 may be greater in one or more dimensions (e.g., wider and/or deeper) than cavity 232. While detent 282 is disposed in cavity 232, the beveled edge of the detent is partly exposed from cavity 232, whereas while the detent is disposed in cavity 234, the beveled edge is disposed entirely within the cavity. Other geometric configurations may also be used to generate this effect. For example, only a proximal face of detent 282 may be beveled.

For some applications, housing 222 is at least in part transparent, so as to enable viewing of the coupling of driver 60 to anchor 40, and/or withdrawal of the anchor from the housing.

Figure 5C:
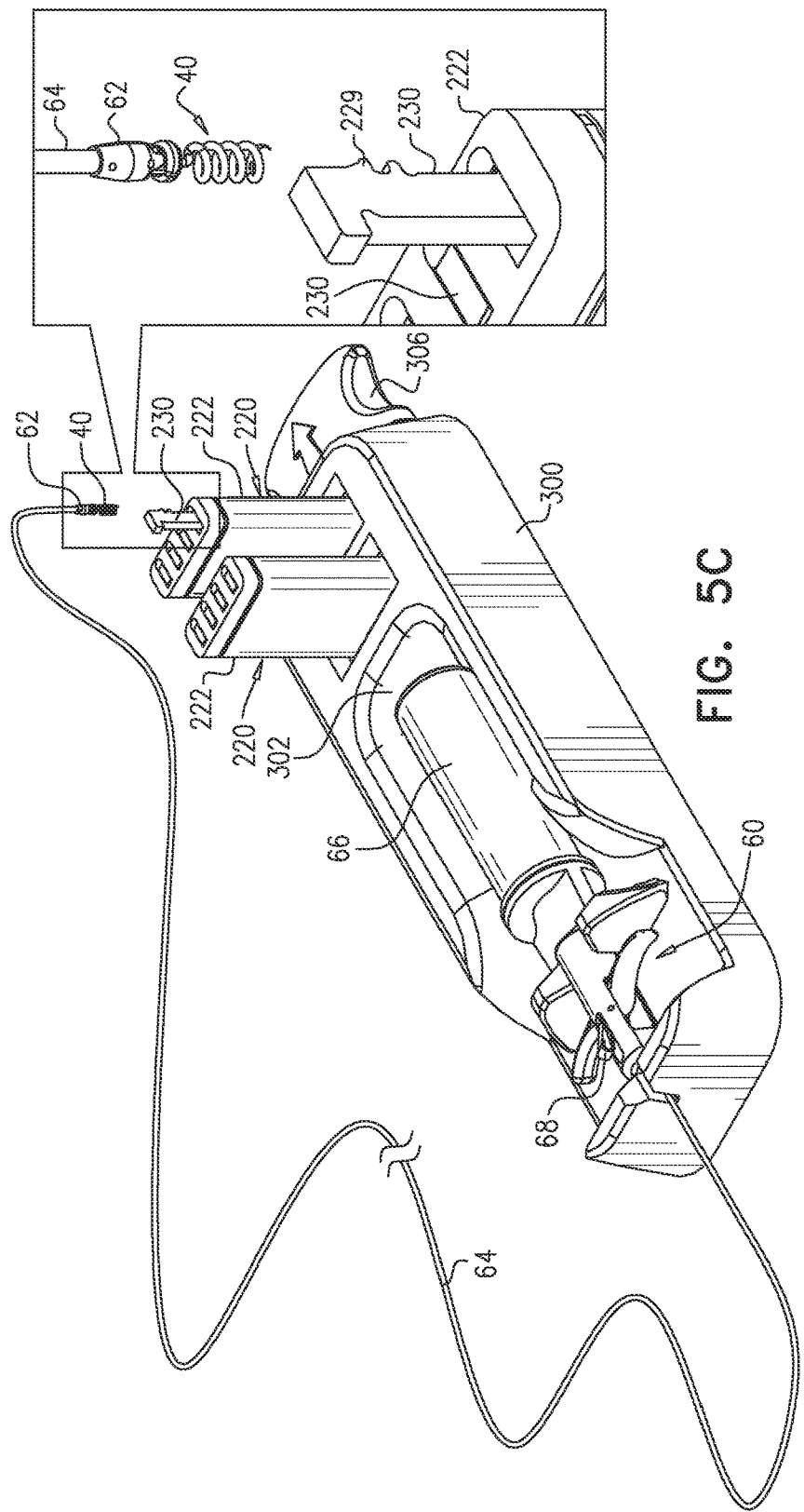

Reference is made to FIGS. 5A-C, which are schematic illustrations of a base 300 to which device 220 (e.g., housing 222 thereof) is couplable, and which is configured to at least partly immobilize the housing, in accordance with some applications of the invention. For some applications, and as shown, more than one device 220 is couplable to base 300. Similarly to devices 20 and 100, for some applications device 220 is used with multi-component tubular system 120 (described hereinabove). For such applications, anchor driver 60 (e.g., anchor-engaging head 62 thereof) is coupled to an anchor 40, and then advanced into system 120 (e.g., via a port 136 at a proximal end of handle 132). As described hereinabove, shaft 64 is flexible, and typically has a length greater than 20 cm, and/or less than 2.5 m, such as greater than 50 cm and/or less than 1.5 m, e.g., between 0.9 m and 1.2 m. Because of this flexibility and length, it may be difficult for an operator (e.g., a physician) to wield and operate handle driver 60 (e.g., to couple head 62 to an anchor while retaining control of shaft 64 and handle 66). Base 300 facilitates such handling by defining a handle receptacle 302 for housing and at least partly immobilizing handle 66.

Typically, base 300 is configured such that when device 220 (e.g., housing 222 thereof) is coupled to the base, the housing is disposed less than 30 cm from receptacle 302 (e.g., less than 20 cm, e.g., less than 10 cm, such as less than 5 cm from the receptacle), and therefore less than 30 cm from handle 66 when the handle is disposed in the receptacle. Because shaft 64 is typically flexible, despite its length typically being greater than (e.g., more than twice as great, e.g., more than 5 times as great, such as 2-10 times as great as) the distance between device 220 and receptacle 302, driver head 62 is insertable into device 220 while handle 66 is disposed in receptacle 302.

For some applications, device 220 is permanently coupled to base 300 (e.g., device 220 and base 330 may be integrated). For some applications device 220 is reversibly couplable to base 300. For example, base 300 may further define at least one housing receptacle 304, configured to house device 220. For such applications, base 300 further comprises a locking element 306, movable between a locked state that locks the housing within the receptacle, and an unlocked state that facilitates release of the housing from the receptacle. For example, and as shown, locking element 306 may comprise one or more bars 308 that are advanceable through a portion of base 300 so as to protrude into (e.g., through) receptacle 304; and housing 222 is shaped to define a respective one or more recesses 310 dimensioned to mate with the bars. Advancing bars 308 into receptacle 304 while housing 222 is disposed in the receptacle thereby locks the housing within the receptacle.

Typically, receptacle 302 is dimensioned such that adjuster 68 is operable while the receptacle houses handle 66. This, along with the proximity of handle 66 to device 220, advantageously facilitates the operator (i) with a first hand, grasping a distal portion of driver 60 and introducing driver head 62 into the opening of housing 222, and (ii) with a second hand, reversibly actuating driver head 62 by operating the adjuster while grasping the distal portion of the driver with the first hand (FIG. 5C; operator's hands not shown). It is hypothesized that this advantageously improves wielding and operation of driver 60 in combination with device 220.

For some applications, base 300 is coupled to system 120, e.g., as described hereinabove for device 100 with respect to FIGS. 3A-C, mutatis mutandis.

For some applications, base 300 does not define a handle receptacle, but instead serves only to hold device 220.

For some applications, device 20, device 100, and/or device 220 is used in combination with one or more techniques described in one or more of the following references, which are all incorporated herein by reference:

U.S. patent application Ser. No. 12/437,103 to Zipory et al., filed May 7, 2009, which published as U.S. 2010/0286767. For example, (1) device 100 of the present application may be used to facilitate the techniques described with reference to FIGS. 2-3 and/or 6A-12 of U.S. 2010/0286767 to Zipory et al., mutatis mutandis; (2) anchor driver 60 of the present application may comprise or correspond to anchor driver 68 and/or anchor deployment manipulator 24 of U.S. 2010/0286767 to Zipory et al., mutatis mutandis; (3) tissue anchor 40 of the present application may comprise or correspond to anchor 38 of U.S. 2010/0286767 to Zipory et al., mutatis mutandis; and/or (4) implant 140 of the present application may comprise or correspond to annuloplasty ring 22 of U.S. 2010/0286767 to Zipory et al., mutatis mutandis.

U.S. patent application Ser. No. 12/689,635 to Zipory et al., filed Jan. 19, 2010, which published as U.S. 2010/0280604. For example, (1) device 100 of the present application may be used to facilitate the techniques described with reference to FIGS. 2-3 and/or 11A-17 of U.S. 2010/0280604 to Zipory et al., mutatis mutandis; (2) anchor driver 60 of the present application may comprise or correspond to anchor driver 68 and/or anchor deployment manipulator 24 of U.S. 2010/0280604 to Zipory et al., mutatis mutandis; (3) tissue anchor 40 of the present application may comprise or correspond to anchor 38 of U.S. 2010/0280604 to Zipory et al., mutatis mutandis; and/or (4) implant 140 of the present application may comprise or correspond to annuloplasty ring 22 of U.S. 2010/0280604 to Zipory et al., mutatis mutandis.

PCT patent application IL2012/050451 to Sheps et al., filed Nov. 8, 2013, which published as WO 2013/069019. For example, (1) device 100 of the present application may be used to facilitate the techniques described with reference to FIGS. 14A-I of WO 2013/069019 to Sheps et al., mutatis mutandis; (2) system 120 of the present application may comprise or correspond to system 10 of WO 2013/069019 to Sheps et al., mutatis mutandis; (3) anchor driver 60 of the present application may comprise or correspond to anchor deployment manipulator 61 and/or anchor driver 36 of WO 2013/069019 to Sheps et al., mutatis mutandis; and/or (4) implant 140 of the present application may comprise or correspond to annuloplasty structure 222 and/or sleeve 26 of WO 2013/069019 to Sheps et al., mutatis mutandis.

PCT patent application IL2013/050860 to Sheps et al., titled "Controlled steering functionality for implant-delivery tool", filed on Oct. 23, 2013, which published as WO 2014/064694. For example, (1) device 100 of the present application may be used to facilitate techniques described with reference to FIGS. 10A-I, 12A-14B, 18A-C, 21-28, 34, and 36 of this PCT application titled "Controlled steering functionality for implant-delivery tool", mutatis mutandis; (2) system 120 of the present application may comprise or correspond to system 10 of this PCT application titled "Controlled steering functionality for implant-delivery tool", mutatis mutandis; anchor driver 60 of the present application may comprise or correspond to anchor deployment manipulator 61, anchor driver 36 and/or anchor driver 2338 of this PCT application titled "Controlled steering functionality for implant-delivery tool", mutatis mutandis; and/or (4) implant 140 of the present application may comprise or correspond to annuloplasty structure 222 and/or sleeve 26 of this PCT application titled "Controlled steering functionality for implant-delivery tool", mutatis mutandis.

PCT patent application IL2013/050861 to Herman et al., titled "Percutaneous tissue anchor techniques", filed on Oct. 23, 2013, which published as WO 2014/064695. For example, (1) device 100 of the present application may be used to facilitate the techniques described with reference to FIGS. 9A-C and/or 13A-D of this PCT application titled "Percutaneous tissue anchor techniques", mutatis mutandis; (2) tissue anchor 40 of the present application may comprise or correspond to tissue anchor 40 of this PCT application titled "Percutaneous tissue anchor techniques", mutatis mutandis; and/or (3) anchor driver 60 of the present application may comprise or correspond to anchor driver 500, anchor driver 236, deployment manipulator 261, or tool 80 of this PCT application titled "Percutaneous tissue anchor techniques", mutatis mutandis.

Reference is again made to FIGS. 1A-5C. Typically, the tissue anchor is dimensioned to fit snugly in the anchor-storage zone of the housing. Typically, the tissue anchor (e.g., core 41 thereof) is dimensioned to slide snugly through the channel of the housing, and for some applications this snug sliding prevents tissue-engaging member 44 of the anchor from touching the housing (e.g., the wall of the channel) when the anchor moves through the channel. Typically, at least a portion of the pin is dimensioned to slide snugly through the chamber.

As described hereinabove, for some applications the obstructing portion of the retaining member of devices 20 and 220 obstructs tissue anchor 40 by engaging core 41 of the anchor. The movement of the retaining member in response to the proximally-directed force applied to the anchor typically moves the obstructing portion such that it does not subsequently engage tissue-engaging member 44 of the anchor. For example, for device 20, portion 29 moves at least partly laterally out of the anchor-storage zone and/or channel 24 (such that element 44 can move past portion 29 without being engaged by it), and for device 220, portion 229 moves longitudinally out of channel 224 (such that element 44 can move past portion 229 without being engaged by it). It is hypothesized that for some applications this advantageously reduces a likelihood of the anchor-handling device (e.g., the obstructing portion of the retaining member) damaging tissue-engaging member 44. It is hypothesized that the use of a retaining member that has an obstructing portion that returns to its original position as soon as core 41 has moved past the obstructing portion, does not have this advantageous feature.

It is to be noted that the technique used to inhibit movement of the retaining member of device 20 may be used to inhibit movement of the retaining member of device 220, mutatis mutandis, and vice versa.

Reference is again made to FIGS. 1A-5C. It is to be noted that, for both device 20 and device 220, proximal withdrawal of anchor 40 typically results in sliding of the retaining member (e.g., the pin) in an at least partly proximal direction. This sliding is typically along an axis that is disposed at and angle of less than 30 degrees with respect to a central longitudinal axis of the channel through which the anchor is withdrawn. For example, for device 20 the angle is typically 8-30 degrees (e.g., 10-20 degrees, such as 11-14 degrees), and for device 220 the angle is typically less than 10 degrees, such as 0 degrees—i.e., parallel with the channel.

Reference is again made to FIGS. 1A-5C. As described hereinabove, the anchor-handling devices allow retrieval of the tissue anchor(s) disposed therein in response to a proximally-directed force that is greater than a threshold force. Typically the threshold force is greater than 300 grams force and/or less than 1500 grams force (e.g., 300-1500 grams force, e.g., 500-1200 grams force, e.g., 500-1000 grams force, such as 600-800 grams force). Tissue anchor 40 typically has a mass of less than 1 g and/or greater than 0.01 g (e.g., 0.01-1 g, e.g., 0.05-0.2 g, e.g., 0.07-0.12 g, such as about 0.1 g). Thus the threshold force (measured in grams force) is typically greater than 300 times (e.g., greater than 1000 times, e.g., greater than 3000 times, e.g., greater than 10,000 times, such as greater than 15,000 times) and/or less than 150,000 times the mass of the tissue anchor (measured in grams). It is to be noted that the threshold force is therefore many times greater than that which would be required simply to prevent the tissue anchor from undesirably exiting the device due to gravity and/or movement of the device (e.g., during transport).

This configuration of the anchor-handling device serves to test coupling of the anchor driver to the tissue anchor before releasing the tissue anchor. Only if the coupling is sufficient to support a proximally-directed force that is greater than the threshold force, will the device release the anchor. This is hypothesized to increase safety and reliability of the use of the anchor and driver, e.g., by reducing a likelihood that the anchor will subsequently become disengaged from the driver at an undesired time (e.g., within the body of a subject). Whereas one might consider testing the anchor-driver coupling subsequently to removal of the anchor from the anchor-handling device, such post-removal testing requires an extra procedural step, and for some applications it increases a likelihood of damaging and/or contamination of the (typically sterile) tissue anchor. Furthermore, whereas the anchor-handling devices described herein facilitate making a second attempt at coupling the driver to the same anchor, post-removal testing typically does not.

Reference is again made to FIGS. 1A-5C. Typically the anchors are provided sterile within the anchor-handling device. As described hereinabove, for some applications, the anchor-handling device is configured such that returning the exposed portion of the retaining member back into the housing requires a distally-directed force that is more than twice as great (in the opposite direction) as the threshold force that was previously required to move the portion out of the housing. For example, the moving of the portion back into the housing may be in effect prevented. As well as facilitating the exposed portion serving as an empty-housing indicator, this characteristic of the anchor-handling device discourages and/or prevents the operator from returning a previously-removed anchor into the device, e.g., thereby ensuring that only sterile anchors are disposed within the device.

For some applications, the anchor-handling devices described herein are configured to be at least in part submerged in saline prior to and/or during use, e.g., to reduce a likelihood of air (e.g., bubbles) being retained by the anchor and/or driver and subsequently introduced into the subject.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A system comprising:
   an anchor driver;
   a housing, shaped to define a channel having an anchor-storage zone and a proximal opening configured to provide access for the anchor driver to the anchor-storage zone;
   a tissue anchor, stored in the anchor-storage zone and slidable through the channel; and
   a retaining member:
      having a retaining state in which the retaining member is configured to retain the tissue anchor in the anchor-storage zone, and
      being configured, by moving in response to a proximally-directed force applied to the tissue anchor, to allow the tissue anchor to leave the anchor-storage zone in response to the proximally-directed force, the proximally-directed force being greater than a pre-determined threshold force;
   wherein the tissue anchor has a mass, and the retaining member is configured such that the threshold force, measured in grams force, is more than 1000 times greater than the mass of the tissue anchor, measured in grams.

2. The system according to claim 1, is configured such that after removal of the tissue anchor from the housing, a distally-directed force required to return the retaining member to the retaining state is more than twice as great as the threshold force.

3. The system according to claim 1, wherein the retaining member is configured such that the threshold force is greater than 300 grams force.

4. The system according to claim 1, wherein, in the retaining state, at least a portion of the retaining member obstructs proximal movement of the tissue anchor by being disposed within the channel.

5. The system according to claim 4, wherein in the retaining state, the anchor driver is slidable through the channel and lockable to the tissue anchor while at least the portion of the retaining member obstructs proximal movement of the tissue anchor by being disposed within the channel.

6. The system according to claim 5, wherein in the retaining state, the anchor driver is slidable through the channel such that a part of the anchor driver becomes positioned between a part of the tissue anchor and a part of the retaining member, and the anchor driver is lockable to the tissue anchor only while the part of the anchor driver is positioned between the part of the tissue anchor and the part of the retaining member.

7. The system according to claim 4, wherein:
the housing is shaped to define a chamber that is in fluid communication with the channel,
at least part of the retaining member is configured to slide within the chamber in response to the proximally-directed force applied to the tissue anchor, and
the retaining member is configured such that, in response to the proximally-directed force applied to the tissue anchor, a second portion of the retaining member moves out of the housing.

8. The system according to claim 7, wherein:
the retaining member comprises a pin, configured to slide through the chamber,
the housing is shaped to define a chamber that is in fluid communication with the channel,
at least part of the retaining member is configured to slide within the chamber in response to the proximally-directed force applied to the tissue anchor,
the housing is shaped to define a cavity that is in fluid communication with the chamber,
at least a portion of the retaining member is resilient,
the retaining member is shaped to define a detent,
in the retaining state, the resilience of at least the portion of the retaining member holds the detent within the cavity, and
the retaining member is configured to deform in response to the proximally-directed force applied to the tissue anchor, such that the detent exits the cavity.

9. The system according to claim 8, wherein:
the cavity comprises a first cavity,
the housing is shaped to define a second cavity that is in fluid communication with the chamber, and
the system is dimensioned such that when the retaining member allows the tissue anchor to leave the anchor-storage zone, further proximal movement of the retaining member causes the detent to move into the second cavity.

10. The system according to claim 9, wherein the second cavity is larger in at least one dimension than the first cavity.

11. The system according to claim 9, wherein the second cavity is differently shaped to the first cavity.

12. The system according to claim 9, wherein the second cavity and the detent are dimensioned such that when the detent is disposed within the second cavity, a distally-directed force required to return the retaining member to the retaining state is more than twice as great as the threshold force.

13. The system according to claim 7, wherein the chamber is in fluid communication with the channel at a distal end of the chamber, and has a proximal-distal longitudinal axis that is disposed at between 5 and 30 degrees from a proximal-distal longitudinal axis of the channel.

14. The system according to claim 4, wherein:
the housing is shaped to define a chamber that is in fluid communication with the channel,
at least part of the retaining member is configured to slide within the chamber in response to the proximally-directed force applied to the tissue anchor, and
a central longitudinal axis of the chamber is parallel with a central longitudinal axis of the channel.

15. The system according to claim 1, wherein the anchor driver comprises:
at a distal end thereof, an anchor-engaging head introducible through the opening of the housing and actuatable to be reversibly coupled to the tissue anchor;
at a proximal end thereof, a handle comprising an adjuster configured to actuate the anchor-engaging head; and
a flexible shaft:
disposed between the distal end of the anchor driver and the proximal end of the anchor driver,
having a length of 50-250 cm, and
configured to be transcatheterally advanced through vasculature of a subject.

16. The system according to claim 15, wherein the opening of the housing is rotationally asymmetrical, a transverse cross-section of the anchor-engaging head is rotationally asymmetrical, and the opening limits a range of rotational orientations of the anchor-engaging head with respect to the opening in which the anchor-engaging head is introducible through the opening.

17. The system according to claim 16, wherein the tissue anchor is stored in the anchor-storage zone in a given rotational orientation of the tissue anchor with respect to the opening, the anchor-engaging head is couplable to the tissue anchor in not all rotational orientations of the head with respect to the tissue anchor, and the anchor-engaging head is couplable to the tissue anchor without rotating the anchor-engaging head subsequently to introducing the anchor-engaging head through the opening.

18. The system according to claim 16, wherein the opening limits the range of rotational orientations such that the anchor-engaging head is introducible through the opening in only a given rotational orientation of the head with respect to the opening.

19. The system according to claim 15, further comprising a base, wherein:
the housing is couplable to the base,
the base is configured to at least partly immobilize the housing, and
the base is shaped to define a receptacle for housing and at least partly immobilizing the handle such that the adjuster remains operable.

20. The system according to claim 19, wherein when the housing is coupled to the base, the housing is disposed less than 30 cm from the receptacle.

21. A system comprising:
an anchor driver;
a housing, shaped to define a channel having an anchor-storage zone and a proximal opening configured to provide access for the anchor driver to the anchor-storage zone;
a tissue anchor, stored in the anchor-storage zone and slidable through the channel; and
a retaining member:
having a retaining state in which the retaining member is configured to retain the tissue anchor in the anchor-storage zone,
being configured, by moving in response to a proximally-directed force applied to the tissue anchor, to allow the tissue anchor to leave the anchor-storage zone in response to the proximally-directed force, the proximally-directed force being greater than a pre-determined threshold force, and being configured such that the threshold force is greater than 300 grams force.

22. The system according to claim 21, wherein the tissue anchor has a mass, and the retaining member is configured such that the threshold force, measured in grams force, is more than 1000 times greater than the mass of the tissue anchor, measured in grams.

23. A system comprising:
an anchor driver;
a housing, shaped to define a channel having an anchor-storage zone and a proximal opening configured to provide access for the anchor driver to the anchor-storage zone;
a tissue anchor, stored in the anchor-storage zone and slidable through the channel; and
a retaining member:
  having a retaining state in which the retaining member is configured to retain the tissue anchor in the anchor-storage zone, and
  being configured, by moving in response to a proximally-directed force applied to the tissue anchor, to allow the tissue anchor to leave the anchor-storage zone in response to the proximally-directed force, the proximally-directed force being greater than a pre-determined threshold force,
wherein:
in the retaining state, at least a portion of the retaining member obstructs proximal movement of the tissue anchor by being disposed within the channel,
the housing is shaped to define a chamber that is in fluid communication with the channel,
at least part of the retaining member is configured to slide within the chamber in response to the proximally-directed force applied to the tissue anchor,
the retaining member is configured such that, in response to the proximally-directed force applied to the tissue anchor, a second portion of the retaining member moves out of the housing,
the housing is shaped to define a cavity that is in fluid communication with the chamber,
at least a portion of the retaining member is resilient,
the retaining member is shaped to define a detent,
in the retaining state, the resilience of at least the portion of the retaining member holds the detent within the cavity, and
the retaining member is configured to deform in response to the proximally-directed force applied to the tissue anchor, such that the detent exits the cavity.

24. The system according to claim 23, wherein the retaining member is configured such that the threshold force is greater than 300 grams force.

25. The system according to claim 23, wherein the tissue anchor has a mass, and the retaining member is configured such that the threshold force, measured in grams force, is more than 1000 times greater than the mass of the tissue anchor, measured in grams.

26. The system according to claim 23, wherein:
the cavity comprises a first cavity,
the housing is shaped to define a second cavity that is in fluid communication with the chamber, and
the system is dimensioned such that when the retaining member allows the tissue anchor to leave the anchor-storage zone, further proximal movement of the retaining member causes the detent to move into the second cavity.

27. The system according to claim 26, wherein the second cavity is larger in at least one dimension than the first cavity.

28. The system according to claim 26, wherein the second cavity is differently shaped to the first cavity.

29. The system according to claim 26, wherein the second cavity and the detent are dimensioned such that when the detent is disposed within the second cavity, a distally-directed force required to return the retaining member to the retaining state is more than twice as great as the threshold force.

30. A system comprising:
an anchor driver;
a housing, shaped to define a channel having an anchor-storage zone and a proximal opening configured to provide access for the anchor driver to the anchor-storage zone;
a tissue anchor, stored in the anchor-storage zone and slidable through the channel; and
a retaining member:
  having a retaining state in which the retaining member is configured to retain the tissue anchor in the anchor-storage zone, and
  being configured, by moving in response to a proximally-directed force applied to the tissue anchor, to allow the tissue anchor to leave the anchor-storage zone in response to the proximally-directed force, the proximally-directed force being greater than a pre-determined threshold force,
wherein:
in the retaining state, at least a portion of the retaining member obstructs proximal movement of the tissue anchor by being disposed within the channel,
the housing is shaped to define a chamber that is in fluid communication with the channel,
at least part of the retaining member is configured to slide within the chamber in response to the proximally-directed force applied to the tissue anchor,
the retaining member is configured such that, in response to the proximally-directed force applied to the tissue anchor, a second portion of the retaining member moves out of the housing, and
the chamber is in fluid communication with the channel at a distal end of the chamber, and has a proximal-distal longitudinal axis that is disposed at between 5 and 30 degrees from a proximal-distal longitudinal axis of the channel.

* * * * *